United States Patent
Gilboa-Geffen et al.

(10) Patent No.: US 10,344,319 B2
(45) Date of Patent: Jul. 9, 2019

(54) ALLERGEN DETECTION

(71) Applicant: DOTS Technology Corp., Natick, MA (US)

(72) Inventors: Adi Gilboa-Geffen, Brookline, MA (US); Renuka Babu Brown, Weston, MA (US)

(73) Assignee: DOTS Technology Corp., Natick, MA (US)

( * ) Notice: Subject to any disclaimer, the term of this patent is extended or adjusted under 35 U.S.C. 154(b) by 6 days.

(21) Appl. No.: 15/030,564

(22) PCT Filed: Oct. 28, 2014

(86) PCT No.: PCT/US2014/062656
§ 371 (c)(1),
(2) Date: Apr. 19, 2016

(87) PCT Pub. No.: WO2015/066027
PCT Pub. Date: May 7, 2015

(65) Prior Publication Data
US 2016/0251703 A1   Sep. 1, 2016

Related U.S. Application Data

(60) Provisional application No. 61/896,399, filed on Oct. 28, 2013, provisional application No. 61/938,528, filed on Feb. 11, 2014, provisional application No. 61/991,068, filed on May 9, 2014, provisional application No. 62/009,958, filed on Jun. 10, 2014,
(Continued)

(51) Int. Cl.
*C12Q 1/68* (2018.01)
*C12Q 1/6818* (2018.01)
*C12Q 1/6811* (2018.01)
*G01N 33/53* (2006.01)
(Continued)

(52) U.S. Cl.
CPC ....... *C12Q 1/6818* (2013.01); *C12N 15/1048* (2013.01); *C12Q 1/6811* (2013.01); *G01N 33/02* (2013.01); *G01N 33/5308* (2013.01); *G01N 2800/24* (2013.01)

(58) Field of Classification Search
None
See application file for complete search history.

(56) References Cited

U.S. PATENT DOCUMENTS

| | | |
|---|---|---|
| 5,538,848 A | 7/1996 | Livak et al. |
| 6,037,130 A | 3/2000 | Tyagi et al. |

(Continued)

FOREIGN PATENT DOCUMENTS

| | | |
|---|---|---|
| WO | 2010018657 A2 | 9/2010 |
| WO | 2012078455 A1 | 6/2012 |

(Continued)

OTHER PUBLICATIONS

Partial Supplementary European Search Report from EP Application No. 14858287, entitled "Allergen Detection," dated May 10, 2017.
(Continued)

*Primary Examiner* — Betty J Forman
(74) *Attorney, Agent, or Firm* — DT Ward, PC; Donna T. Ward; Lingyun Jia

(57) ABSTRACT

The present invention provides allergen detection molecules and devices useful in on-site and rapid detection of allergens, including food allergens.

11 Claims, 42 Drawing Sheets

Specification includes a Sequence Listing.

Related U.S. Application Data provisional application No. 62/026,361, filed on Jul. 18, 2014.

(51) Int. Cl.
  *C12N 15/10* (2006.01)
  *G01N 33/02* (2006.01)

(56) References Cited

U.S. PATENT DOCUMENTS

| | | | |
|---|---|---|---|
| 6,680,377 | B1 | 1/2004 | Stanton et al. |
| 8,071,734 | B2 | 12/2011 | Stanton et al. |
| 2004/0038307 | A1* | 2/2004 | Lee .................... B82Y 5/00 435/7.1 |
| 2008/0180259 | A1 | 7/2008 | Jung et al. |
| 2008/0181821 | A1 | 7/2008 | Jung |
| 2010/0285490 | A1* | 11/2010 | Dees ............... G01N 33/54373 435/7.1 |
| 2011/0065086 | A1 | 3/2011 | Bruno |
| 2012/0040865 | A1 | 2/2012 | Kim |
| 2013/0251638 | A1 | 9/2013 | Wang |
| 2018/0188139 | A1* | 7/2018 | Gilboa-Geffen .......................... G01N 33/5304 |

FOREIGN PATENT DOCUMENTS

| | | | | |
|---|---|---|---|---|
| WO | WO-2012078455 | A1 * | 6/2012 | ............. G01N 33/02 |
| WO | 2013178844 | A1 | 12/2013 | |

OTHER PUBLICATIONS

Pollet et al. "Fast and accurate peanut allergen detection with nanobead enhanced optical fiber SPR biosensor," Talanta 83 (2011) 1436-1441.

Raz et al. "Food Allergens Profiling with an Imaging Surface Plasmon Resonance-Based Biosensor," Anal. Chem. (2010) 82, 8485-8491.

Tran et al. "Selection and Characterization of DNA for Egg White Lysozyme," Molecules (2010) 15, 1127-1140.

Amaya-González, S. et al., "Aptamer-Based Analysis: A Promising Alternative for Food Safety Control" (2013) Sensory 13:16292-16311.

de la Escosura-Muñiz, A. et al., "Immunosensing using nanoparticles" (2010) Materialstoday 13(7-8):24-34.

Hall, B. et al., "Kinetic Optimization of a Protein-Responsive Aptamer Beacon" (2009) Biotechnology and Bioengineering 103(6):1049-1059.

Hamaguchi, N. et al., "Aptamer Beacons for the Direct Detection of Proteins" (2001) Analytical Biochemistry 294:126-131.

Handlogten, M.W., et al., "Design of a Heterobivalent Ligand to Inhibit IgE Clustering on Mast Cells" (2011) Chemistry & Biology 18:1179-1188.

Kostrikis, L.G., et al. "Molecular Beacons Spectral Genotyping of Human Alleles" (1998) Science 279:1228-1229.

Leung, C.-H. et al., "Survey and Summary Luminescent detection of DNA-binding proteins" (2012) Nucleic Acids Research 40(3):941-955.

Low, S.Y., et al. "A DNA Aptamer Recognizes the Asp f 1 Allergen of Aspergillus fumigatus" (2009) Biochem Biophys Res Commun. 386(3):544-548.

Lu, Y. et al., "Nanoparticles/Dip Stick" (2009) Nucleic Acid and Peptide Aptamers: Methods and Protocols 535:223-239.

Mairal, T. et al., "FRET-based dimeric aptamer probe for selective and sensitive Lup an 1 allergen detection" (2014) Biosensors and Bioelectronics 54:207-210.

Medley, C.D., et al. "Gold Nanoparticle-Based Colorimetric Assay for the Direct Detection of Cancerous Cells" (2008) Anal. Chem. 80(4):1067-1072.

Nadal, P. et al., "DNA Aptamers against the Lup an 1 Food Allergen" (2012) PLoS ONE 7(4):e35253.

Nadal, P. et al., "Probing high-affinity 11-mer DNA aptamer against Lup an 1 (β-conglutin)" (2013) Anal. Bioanal. Chem. 405:9343-9349.

Pilolli, R. et al., "Advances in biosensor development based on integrating nanotechnology and applied to food-allergen management" (2013) Trends in Analytical Chemistry 47:12-26.

Pinto, A. et al., "Label-free detection of gliadin food allergen mediated by real-time apta-PCR" (2013) Anal. Bioanal. Chem. 406(2):515-524.

Tan, L. et al., "Molecular beacons for bioanalytical applications" (2005) Analyst 130:1002-1005.

Tran, D.T., "Selection and Characterization of DNA Aptamers for Egg White Lysozyme" (2010) Molecules 15:1127-1140.

Tran, D.T., "Selection of aptamers against Ara h 1 protein for FO-SPR biosensing of peanut allergens in food matrices" (2013) Biosensors and Bioelectronics 43:245-251.

Tuleuova, N. et al., "Micropatterning of Aptamer Beacons to Create Cytokine-Sensing Surfaces" (2010) Cellular and Molecular Bioengineering 3(4):337-344.

Wang, Y. et al., "Ultrasensitive calorimetric detection of protein by aptamer—Au nanoparticles conjugates based on a dot-blot assay" (2008) Chem. Commun. 2520-2522.

Wang, H.-Q., et al., "Fluorescence protection assay: a novel homogeneous assay platform toward development of aptamer sensors for protein detection" (2011) Nucleic Acids Research 39(18):e122.

Xiao, Y. et al., "Fluorescence Detection of Single Nucleotide Polymorphisms via a Single, Self-Complementary, Triple-stem DNA Probe" (2009) Angew Chem Int Ed Engl 48(24):4354-4358.

Yao, C. et al., "Development of a Quartz Crystal Microbalance Biosensor with Aptamers as Bio-recognition Element" (2010) Sensors 10:5859-5871.

Inellectual Property Office of Japan First Office Action dated Mar. 28, 2017 Application No. 2016-552208, entitled Allergen Detection and English Translation included.

Australian Government IP Australia Examination Report No. 1 for standard patent application dated Dec. 9, 2016 Application No. 2014342528, Allergen Detection.

Canadian Intellectual Property Office First Office Action dated Feb. 20, 2017 Application No. 2,928,644, entitled Allergen Detection.

The State Intellectual Property Office of the People's Republic of China First Office Action dated Feb. 13, 2017 Application No. 2014800714086, entitled Allergen Detection and English Translation included.

Food Allergen Handbook, 2012, Neogen Corporation, pp. 1-28. Retrieved from the internet: <https://www.neogen.com/FoodSafety/pdf/AllergenHandbook_12.pdf> on Jan. 7, 2015 (Jan. 7, 2015).

International Search Report and Written Opinion dated Feb. 10, 2015 in Application No. PCT/US2014/062656, entitled: Allergen Detection.

The State Intellectual Property Office of the People's Republic of China Second Office Action dated Oct. 20, 2017 Application No. 2014800714086, entitled Allergen Detection and English Translation included.

Intellectual Property Office of Japan Office Action dated Nov. 7, 2017 Application No. 2016-552208, entitled Allergen Detection and English Translation included.

Extended European Search Report for corresponding European Application No. 14858287.7 dated Aug. 22, 2017 entitled "Allergen Detection".

Canadian Office Action dated Feb. 8, 2018 Canadian Application No. 2928644, entitled Allergen Detection.

The State Intellectual Property Office of the People's Republic of China Third Office Action dated Apr. 24, 2018 Application No. 2014800714086, entitled Allergen Detection and English Translation included.

Canadian Office Action for corresponding Canadian Application No. 2928644 entitled "Allergen Detection" dated Jan. 8, 2019.

Fourth Chinese Office Action for corresponding Chinese Application No. 2014800714086 entitled "Allergen Detection" dated Jan. 21, 2019.

Australian Examination Report 1 for corresponding Australian Application No. 2017272280 entitled "Allergen Detection" dated Jan. 11, 2019.

(56) References Cited

OTHER PUBLICATIONS

Tran, D.T. et al. (2012) "Selection of Aptamers Against Ara H 1 Protein for FO-SPR Biosensing of Peanut Allergens in Food Matrices" Biosens Bioelectron vol. 43, pp. 245-251 DOI: 10.1016/j.bios.2012.12.022.

Hamaguchi, N. et al (2001). "Aptamer beacons for the direct detection of proteins". Analytical Biochemistry, 294(2), 126-131. DOI: 10.1006/abio.2001.5169.

\* cited by examiner

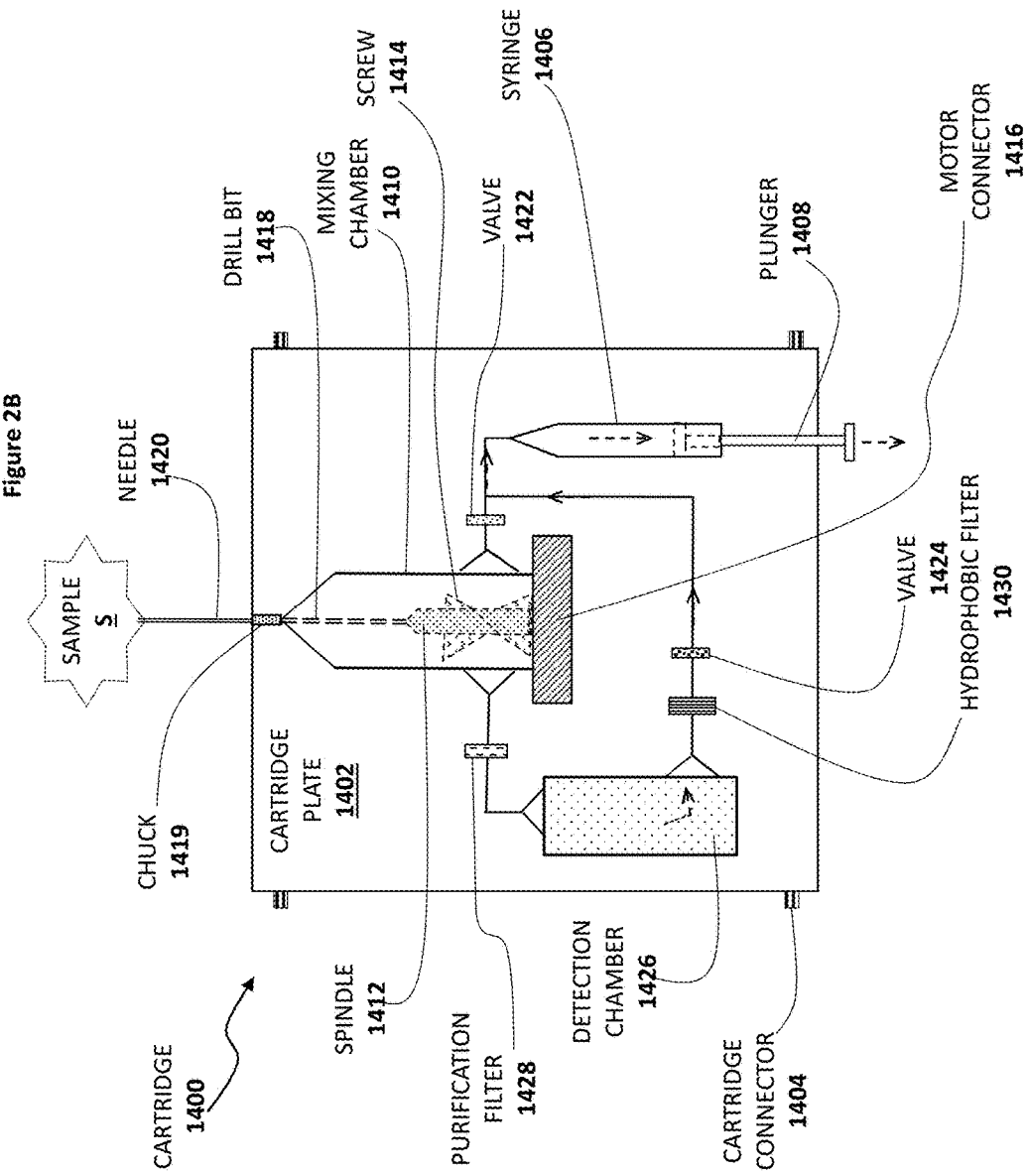

Peanut recovery rate compared to ELISA

Figure 35A MB7 can detect diluted peanut allergen in processed foods
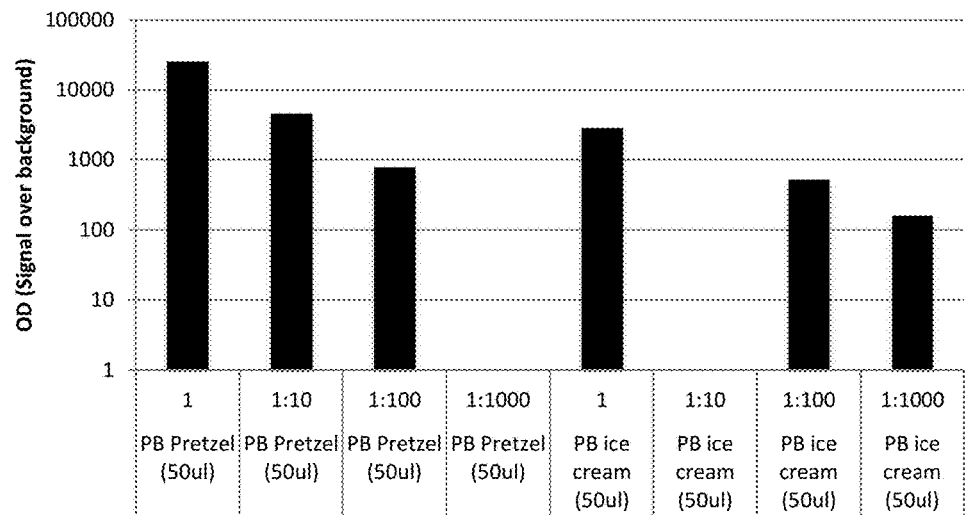
Figure 35B MB9 can detect diluted peanut allergen in processed foods
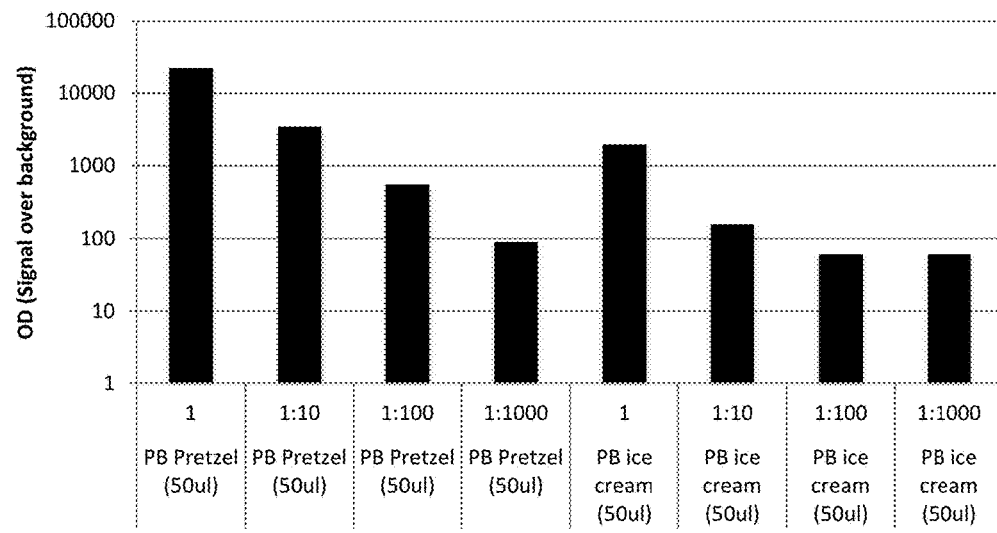

ALLERGEN DETECTION

REFERENCE TO RELATED APPLICATIONS

This application is a 35 U.S.C. § 371 U.S. National Stage Entry of International Application No. PCT/US2014/062656 filed Oct. 28, 2014, which claims the benefit of priority of U.S. Provisional Application Ser. No. 62/026,361, filed on Jul. 18, 2014; U.S. Provisional Application Ser. No. 62/009,958, filed on Jun. 10, 2014; U.S. Provisional Application Ser. No. 61/991,068, filed on May 9, 2014; U.S. Provisional Application Ser. No. 61/938,528, filed on Feb. 11, 2014; and U.S. Provisional Application Ser. No. 61/896,399, filed on Oct. 28, 2013; the contents of each of which are incorporated herein by reference in their entirety.

REFERENCE TO SEQUENCE LISTING

The present application is being filed along with a Sequence Listing in electronic format. The Sequence Listing is provided as a file entitled SEQLST20661000US371.txt, created on Apr. 19, 2016, which is 49,561 bytes in size. The information in the electronic format of the sequence listing is incorporated herein by reference in its entirety.

FIELD OF THE INVENTION

The present invention relates to methods, devices, and molecules for allergen detection.

BACKGROUND OF THE INVENTION

Allergy is a serious medical condition affecting millions of people worldwide, with about 15 million people in the United States, including many children. During an allergic reaction, the immune system mistakenly targets an allergen as a threat and attacks it. The allergic reaction may affect the skin, the digestive system, the gastrointestinal tract, the respiratory system, the circulatory system and the cardiovascular system; in some allergic reactions, multiple organ systems are affected. Allergic reactions range from mild to severe or life-threatening. Severe symptoms may include difficulty in breathing, low blood pressure, chest pain, loss of consciousness, and anaphylaxis. People having allergies currently manage their allergies by avoiding any food that might contain that specific allergen. These restrictions have a major impact on the patients' quality of life and there remains no method for assessing the true allergen content of food. In the United States, food allergy symptoms send someone to the emergency room every three minutes. A rapid method for determining the presence of an allergen would be of great benefit. A portable device that enables the patients to test their food and determine accurately and immediately the allergen content will be beneficial to provide for an informed decision on whether to consume or not.

U.S. Pat. No. 5,824,554 to McKay teaches a dining mat formed of an absorbent material and small spots of chemical reagents applied to isolated zones on the mat, for detection of food allergens. If the food product contains the allergenic substance, the chemical reagent will change its appearance indicating the presence of the allergenic substance in the food product. The detection limit and the detection specificity are limited by the chemical reagent used in the spots. A drawback is that false negatives are highly possible when analyzing solid food products because of the long reaction times between the solid food products and the spot reagent.

US Patent Application Pub. No. 2008/0182339 and U.S. Pat. No. 8,617,903 to Jung et al. teaches a method of detecting an allergen by processing samples with microfluidic chips configured for analysis of one or more allergen indicators, detecting the allergen indicators with one or more detection units, and displaying results with one or more display units. The detecting system comprises a microfluidic chip, a reagent delivery unit, a centrifugation unit, an analysis unit, a detection unit, a display unit, and a recording unit. The device is not sufficiently compact to be portable.

US Patent Application Pub. No. 2010/0210033 to Scott et al. teaches a portable device for detecting food allergens comprising a housing, a sample inlet port, a means for indicating the presence of the potential allergen in the sample, and an allergen detection chip comprising an antibody to the potential allergen, wherein the antibody is labeled with a detectable tag.

U.S. Pat. No. 7,527,765 to Royds teaches a food testing device for identifying the presence of harmful contaminants in a food sample, comprising a disposable sample container, a mechanical liquefier including a blade assembly, a test supply compartment with a reagent having an affinity for the harmful contaminant and capable of detecting the harmful contaminant in the liquefied food sample, and producing a visual cue upon recognition of the harmful contaminant.

Aptamers, as well as devices and methods of using them in the detection of proteins in food, are disclosed in several patents and patent applications (each of which is incorporated herein by reference in its entirety), including: U.S. Pat. No. 8,633,140 to Kim, et al., which teaches a microarray of functionalized polydiacetylene molecular sensors; U.S. Pat. No. 8,618,046 to Brunner, et al., which teaches a method for treating atherosclerosis using aptamer-based anti-CETP-antibody-inducing antigens; and U.S. Pat. No. 8,614,466 to Rasooly, et al., which teaches a method and system employing a physical principle called "electrical percolation," (flow of electricity through a random resistive network) for electrically detecting biomolecular binding in a semiconductor. In one embodiment, capture molecules for binding target molecules can be an aptamer. U.S. Pat. No. 8,563,298 to Lowery, Jr., et al. teaches NMR systems and methods for the collection and detection of analytes. U.S. Pat. No. 8,507,458 to Yokota, et al. teaches a system for delivering nucleic acids for suppressing target gene expression by utilizing endogenous chylomicron, wherein the nucleic acid may be an aptamer. U.S. Pat. No. 8,236,933 to Herzog, et al. teaches transgenic animals having a reduced level of expression of peptide YY (PYY) and methods of using the transgenic animals for screening a library of aptamers and identifying agonists and antagonists of PYY. U.S. Pat. No. 8,232,584 to Lieber, et al. teaches a fluorescence based nanoscale wire biosensor devices and methods for detecting analytes, wherein an aptamer may be indirectly immobilized relative to the nanoscale wire. U.S. Pat. No. 7,977,462 to Hornbeck et al. teaches lateral flow devices for detecting and quantitating novel tyrosine phosphorylation sites identified in carcinoma and/or leukemia. U.S. Pat. No. 7,973,079 to Mata, et al. teaches biosensors for detecting macromolecules and other analytes that can modulate the activity or availability of serum retinol, retinol-binding protein (RBP) and/or transthyretin (TTR). U.S. Pat. No. 7,855,057 to Gordon, et al. teaches methods, reagents and apparati for detecting small quantities of protein isoforms (e.g., due to alternative splicing, or different disease protein isoforms or degradation products) in a sample, including using combinations of capture agents, wherein the capture agent may be an aptamer. U.S. Pat. No. 7,850,964 to Vukicevic, et al. teaches nucleic acid biosensors of bone morphogenetic proteins (BMPs), e.g., BMP-1 procollagen c-proteinase, for diagnosis and treatment of bone and soft tissue defects and disorders.

Anaphylatoxin C5a- (complement factor 5a)-binding aptamers are described in PCT Publications WO 2009/040113, WO 2010/108657 and WO 2013/104540 to Buchner, et al. Buchner, et al. also describe aptamers that bind to CXC chemokine stromal cell-derived factor-1 (SDF-I) in PCT Publication WO 2009/019007.

Molecular beacons (MBs) are hairpin-shaped oligonucleotides that contain both fluorophore and quencher moieties and act like switches. When in a closed state, the fluorophore and quencher are brought together and the fluorescence is quenched ("turned off") by resonance energy transfer. When a conformational change opens the hairpin structure and the fluorophore and quencher are separated, the quencher can no longer quench and fluorescence is restored ("turned on"). MBs are particularly useful in detection devices and diagnostic assays requiring a probe to have high sensitivity and excellent molecular recognition specificity; they are extraordinarily target-specific, ignoring nucleic acid target sequences that differ by as little as a single nucleotide. Other advantages of MBs are: (1) sensitivity can allow for real-time monitoring; (2) low background signal allows for a fluorescence enhancement of more than 200 times; (3) MBs allow "detection without separation," where it is impossible or undesirable to isolate the probe-target hybrids from an excess of the unhybridized probes. The specificity provided by the MB loop-stem structure has been demonstrated to be applicable in a variety of biological environments. The compositions, methods and devices disclosed herein are applicable in solution-based (in vitro) investigations of RNA-DNA interactions, protein-DNA interaction studies, measurements within living systems, and biosensor design. For example, compositions described herein can be used in in vitro investigations such as real-time monitoring of DNA/RNA amplification during PCR; rapid and reliable mutation detection for clinical diagnosis (Xiao, et al., (2009) *Fluorescence Detection of Single Nucleotide Polymorphisms via a Single, Self-Complementary, Triple-stem DNA Probe*. Angew Chem. Int. Ed. Engl. 48(24):4354-4358); spectral genotyping (Kostrikis, et al., Science, 1998, 279: 1228); DNA sticky-end pairing (SEP) analysis; visualization of subcellular localization and cellular transport pathway of RNAs (Tan et al., (2005) *Molecular Beacons for Bioanalytical Applications. Analyst* 130: 1002-1005).

Exemplary molecular beacons are reviewed in Leung, et al., 2011 (Nucleic Acids Research, 2012, 40(3):941-955) and described in U.S. Pat. No. 8,188,255 to Litman et al., which teaches microRNA (miRNA) sequences associated with cancer, and their detection using aptamers and molecular beacons; U.S. Pat. No. 7,282,360 to Meyers et al., which teaches novel protein kinase, serine/threonine protein kinase, serine/threonine phosphatase, prolyl oligopeptidase, trypsin, serine protease, and ubiquitin carboxy-terminal hydrolase family members, referred to herein as "53070, 15985, 26583, 21953, m32404, 14089, and 23436," and generally discloses detection of them using aptamers or molecular beacons; and U.S. Pat. No. 6,730,491 to Kapeller-Libermann et al., which teaches three allegedly novel protein kinase family members, referred to herein as "2504, 15977, and 14760" and generally discloses detection of them using aptamers or molecular beacons.

There remains a need for a portable and reusable device for fast and accurate detecting allergens. There also remains a need for detecting multiple allergens with a single device.

SUMMARY OF THE INVENTION

The present invention provides devices, methods and detection molecules for use in allergen detection in various types of samples.

One aspect of the invention is a method of detecting one or more allergens in a sample comprising the steps of (a) obtaining a sample suspected of containing an allergen, (b) digesting the sample of (a) with one or more buffers, (c) contacting the digested sample with a detection molecule, (d) treating the contacted sample with an excitation means, and (e) visualizing the interaction of the detection molecule and the allergen.

Another aspect of the invention is a device for detecting an allergen in a sample. The device comprises: a body configured to support the following components: (a) a cartridge for collection and processing of the sample; (b) means for providing fluorescence excitation; (c) a light filter for filtering of fluorescence emission; (d) a detection chamber for mixing of the allergen and a detection molecule; (e) a detector for detecting fluorescence emissions, the detector comprising a means for digitizing detected signals; and (f) a display window for receiving the detected signals and indicating detection of the allergen.

BRIEF DESCRIPTION OF THE DRAWINGS

The foregoing and other objects, features and advantages will be apparent from the following description of particular embodiments of the invention, as illustrated in the accompanying drawings. The schematic drawings are not necessarily to scale. Instead, emphasis is being placed upon illustrating certain operating principles.

FIG. 2B is a schematic representation of the same cartridge 1400 of FIG. 2A, which shows direction of flow of fluids within the cartridge upon retraction of the syringe plunger 1408 out of the barrel of the syringe 1406. Fluid is withdrawn from the detection chamber 1426 through the second one-way valve 1424 back to the barrel of the syringe 1406.

FIG. 22A shows K buffer prebake recovery rates and FIG. 22B shows K buffer postbake recovery rates.

FIG. 35A is a histogram showing MB7 detection of diluted peanut allergen in processed foods such as pretzel and ice cream. FIG. 35B is a histogram showing MB9 detection of diluted peanut allergen in processed foods such as pretzel and ice cream.

DETAILED DESCRIPTION OF THE INVENTION

Figure 1:
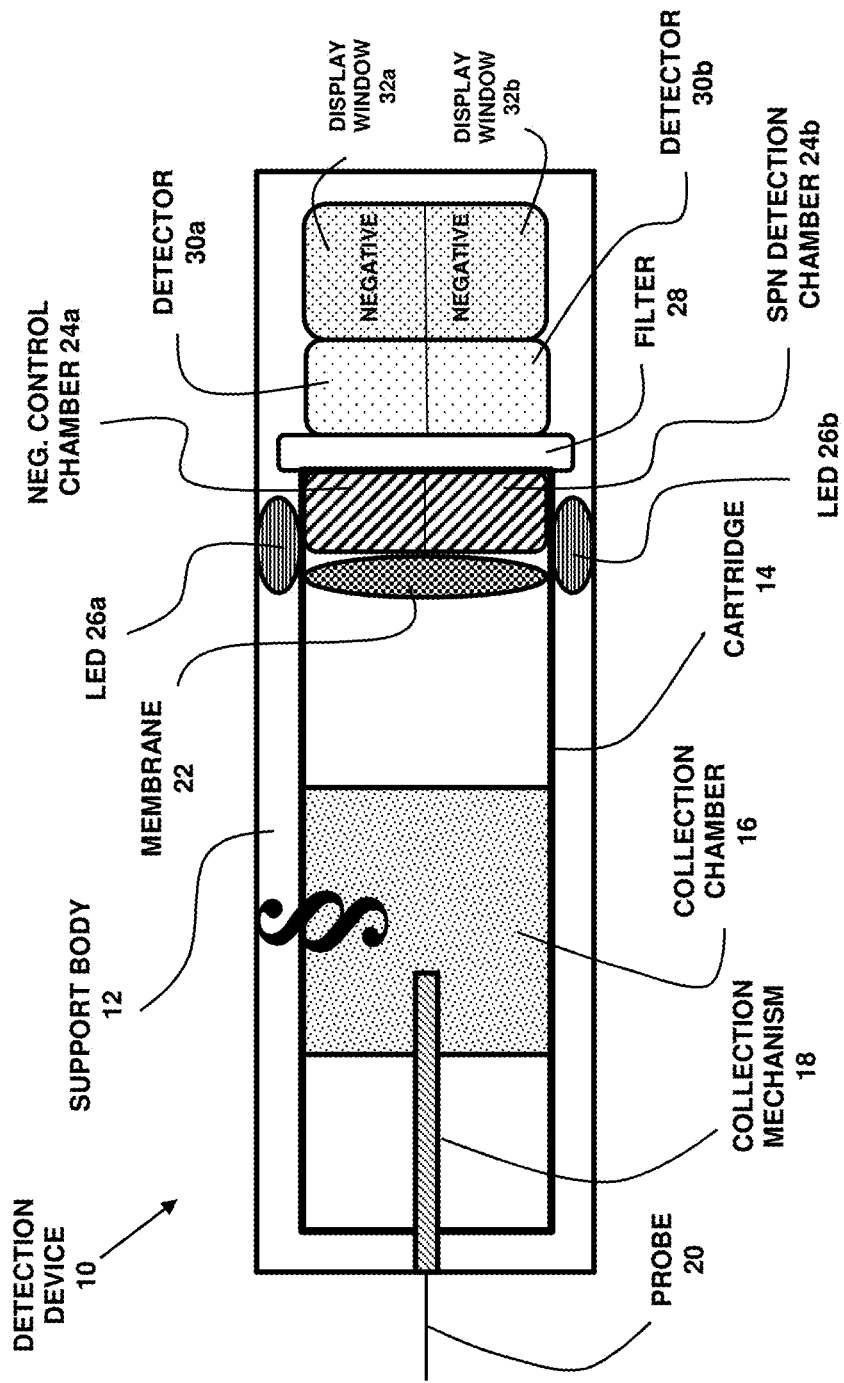
FIG. 1 is a schematic representation of a detection according to one embodiment of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of methods featured in the invention, suitable methods and materials are described below in the detailed description, examples and claims. Where reference numerals are used to describe various features, similar reference numerals are used to describe features with similar functions.

The use of analytical devices to ensure food safety has not yet advanced to the point of fulfilling its promise. In particular, portable devices based on simple, yet accurate, sensitive and rapid detection schemes have not yet been developed for detection of the wide variety of known allergens. One of the more recent reviews of aptamer-based analysis in context of food safety control indicated that while a great variety of commercial analytical tools have been developed for allergen detection, most of them rely on immunoassays. It was further indicated that the selection of aptamers for this group of ingredients is emerging (Amaya-González et al., Sensors 2013, 13, 16292-16311, incorporated herein by reference in entirety).

The methods and devices described herein contemplate the use of nucleic acid-based detector molecules for detection of allergens. In a broad concept, the methods and devices described herein may be used for the detection of any protein content in a sample in a large variety of applications in addition to food safety, such as, for example, medical diagnosis of diseases in civilian and battlefield settings, environmental monitoring/control and military use for the detection of biological weapons. In even broad applications, the methods and devices of the present invention may be used to detect any biomolecules which nucleic acid-based detector molecules bind. As some non-limiting examples, the detection methods and devices may be used on the spot detection of cancer markers, in-field diagnostics (exposure the chemical agents, traumatic head injuries etc.), third-world applications (TB, HIV tests etc.), emergency care (stroke markers, head injury etc.) and many others.

As described below, one particular class of such nucleic acid-based detector molecules are aptamers. The present inventors have recognized that aptamers are particularly well suited to provide core sequences for detector molecules because the iterative approach of the SELEX process (described hereinbelow) can be used to produce aptamers against essentially any molecular target (or portion thereof). Such aptamers have high affinity and binding specificity for their targets. The present inventors have also recognized that production of signaling polynucleotides (described in detail hereinbelow) using an aptamer as the core sequence allows convenient linkage to various reporter molecules. The relatively low production cost of signaling polynucleotides based on aptamer core sequences is also advantageous with respect to the objective of development of simple, yet effective detection assays for biomolecule sensors such as the sensor devices described herein. Lastly, the present inventors have recognized that allergen detection in various matrices of food products can be conveniently performed using aptamer-based detector sequences such as signaling polynucleotides, which are particularly well suited for use in a simple and portable sensor that can be used repetitively with high sensitivity and reproducibility at ambient temperature to ensure food safety.

By way of non-limiting example, a process for in vitro selection of a single stranded DNA aptamer specific for the anaphylactic toxic allergen, ß-conglutin, Lup an 1 has been reported (Nadal, et al., (2012) *DNA Aptamers against the Lup an 1 Food Allergen*. PLoS ONE 7(4): e35253). Briefly, the ß-conglutin subunit from lupin was purified and chemically crosslinked to magnetic beads. Peptide mass fingerprinting was used to ensure the presence of the ß-conglutin on the surface of the beads. A DNA library pool having a population variability of $10^{14}$ was amplified using a phosphorothioated forward primer and the T7 Gene 6 Exonuclease to generate single stranded 93-mer DNA sequences. The library pool was incubated with the protein-conjugated magnetic beads. Each round of SELEX was monitored using PCR, comparing the amount of DNA liberated from the protein-conjugated beads to that obtained from unconjugated beads. Evolution was monitored using enzyme linked oligonucleotide assay (ELONA) and surface plasmon resonance (SPR). After 15 rounds of SELEX, the enriched DNA was cloned, sequenced and consensus motifs identified, the affinity and specificity of these motifs were evaluated, and their secondary structures predicted. The resulting aptamers were evaluated using competitive ELONA for the detection and quantification of the ß-conglutin lupin allergen. Thus, the original 93-mer with $K_D$ 3.6×10$^{-7}$ was selected and truncated to an 11-mer with $K_D$ of 1.7×10$^{-9}$ (Nadal, et al., (2013) *Probing high-affinity* 11-*mer DNA aptamer against Lup an* 1 (β-*conglutin*). Anal. Bioanal. Chem. 405:9343-9349). This truncated 11-mer is guanine-rich and predicted to fold into G-quadruplex structures, composed of stacked guanine tetrads, which are stabilized by Hoogsteen-type hydrogen bonds between the guanines and by interactions with cations located between the tetrads. A sensitive method exploiting fluorescence resonance energy transfer (FRET) was recently reported. for rapid and sensitive detection of Lup an 1, using a high affinity dimeric form of the truncated 11-mer anti-β-conglutin aptamer, with each monomeric aptamer being flanked by donor/acceptor moieties. The dimeric form in the absence of target yields fluorescence emission due to the FRET from the excited fluorophore to the proximal second fluorophore. However, upon addition of β-conglutin, the specific interaction induces a change in the bi-aptameric structure resulting in an increase in fluorescence emission. The method is highly specific and sensitive, with a detection limit of 150 μM, providing an effective tool for the direct detection of the toxic β-conglutin subunit in foodstuffs in just 1 min. at room temperature (Mairal, et al., *FRET-based dimeric aptamer probe for selective and sensitive Lup an* 1 *allergen detection*. Biosensors and Bioelectronics, (2014) 54:207-210).

Allergen families that can be detected using the device described herein include allergens from legumes such as peanuts, tree nuts, eggs, milk, soy, spices, seeds, fish, shellfish, wheat gluten, rice, fruits and vegetables. The allergen may be present in a flour or meal. The device is capable of confirming the presence or absence of these allergens as well as quantifying the amounts of these allergens.

In some of embodiments, aptamers that target to detect 8 major food allergens (i.e. wheat, egg, milk, peanuts, treenuts, fish, shell-fish and soy), may be designed and tested. The eight major food allergens that make up 90% of food allergies. The aptamers with high selectivity, specificity and stability are selected and further labeled as detection molecules.

The devices and methods of the present invention can detect and identify pathogenic microorganisms in a sample. Pathogens that can be detected include bacteria, yeasts, fungi, viruses and virus-like organisms. Pathogens could cause diseases in animals and plants; contaminate food, water, soil or other sources; or be used as biological agents in military fields. The device is capable of detecting and identifying these pathogens.

Another important application includes the use of the methods and devices of the present invention for medical care, for example, to diagnose a disease, to stage a disease progression and to monitor a response to a certain treatment.

Expanded applications outside of the field of food safety include in-field use by military organizations, testing of antibiotics and biological drugs, environmental testing of products such as pesticides and fertilizers, testing of dietary supplements and various food components and additives prepared in bulk such as caffeine and nicotine, as well as testing of clinical samples such as saliva, skin and blood to determine if an individual has been exposed to significant levels of an individual allergen.

Compositions of the Invention

Described herein are compounds, compositions and methods for the design, preparation, use and manufacture of assays, devices and/or kits for the detection of allergens.

As used herein, the term "allergen" means a compound, substance or composition that causes, elicits or triggers and immune reaction in a subject. As such, allergens are typically referred to as antigens.

Any molecule which is capable of, or does, interact with and/or bind to one or more allergens in a way that allows detection of such allergen in a sample is referred to herein as an "allergen detection molecule" or "detection molecule."

Detection Devices and Cartridges

One aspect of the present invention is a detection device which employs a cartridge. In one embodiment, the detection device of the present invention is a handheld product that can specifically detect minute concentrations of allergens in a variety of food samples.

In some embodiments, the detection device is designed for simple, fast (less than 5 min) one-step execution.

In some embodiments, the detection device is designed such that disposable cartridges, unique for specific allergens will be placed in the device for detection of the allergen unique for that cartridge.

With reference to FIG. 1, one embodiment of the detection device 10 is shown. The device has a main support body 12 which may be formed of plastic or other suitable support material. The support body 12 is provided with means for holding a cartridge 14 in place on a working surface of the body 12. One general embodiment of the cartridge is now described and a description of another embodiment of the cartridge 1400 will be provided hereinbelow. The cartridge 14 includes a collection chamber 16 for holding a sample such as a food sample S which is to be tested for the presence of an allergen. In certain embodiments, the cartridge 14 is disposable. In certain embodiments, the collection chamber 16 is provided with a volume of buffer for digestion of the sample. The volume of buffer may range from about 100 μL to about 500 μL. Also included in the device 10 is a sample collection mechanism 18 which may include a combination of a micro-vacuum pump (not shown), a probe 20 and a probe holder (not shown). The cartridge 14 also includes a protein extraction chamber with an extraction membrane 22. The vacuum pump may be used to increase the rate of flow of extracted protein through the extraction membrane 22. Also included in the disposable cartridge are two detection chambers 24a and 24b. Detection chamber 24a holds a negative control and detection chamber 24b holds a signaling polynucleotide for signaling the presence of a molecular target of interest, such as an allergen.

Light emitting diodes (LEDs) 26a and 26b are supported by the body 12 adjacent to the cartridge 14. The LEDs 26a and 26b are essentially identical and provide light of an excitation wavelength appropriate to excite the fluorophore of the signaling polynucleotide. The light paths of the LEDs 26a and 26b are directed into their corresponding detection chambers 24a and 24b.

Also supported by the body 12 outside of the cartridge 14 are a filter 28 for receiving fluorescence emitted from the detection chambers 24a and 24b and transmitting only the wavelength(s) of interest, and corresponding fluorescence detectors 30a and 30b which include processors for converting photomultiplier tube (PMT) signals to useful readouts (i.e. measuring fluorescence output and converting it to digital signals). The data corresponding to the digital signals are then provided in corresponding display windows 32a and 32b which function as user interface screens. In the present example shown in FIG. 1, both display windows display the reading "NEGATIVE" indicating that the control is serving its intended function and analysis of the sample indicates that it does not contain the allergen being tested, to any meaningful level.

In certain embodiments, the length of the device 10 is approximately 10 cm long. The sample obtained from the probe 20 is transported to the collection chamber 16. The probe 20 is used to obtain numerous samples (approx. 5 samples up to 200 mg). When the device is inactive, the collection probe 20 will be hidden from sight inside the device 10 and exposed either by an electronic command or manually.

Other features which may be provided include, but are not limited to: A drill for obtaining a core sample of a food product, for example. The sample collection probe may optionally be provided with a cover.

In some embodiments, the collection chamber has a volume sufficient to contain 100-500 μL of digestion buffer. The food specimens transported to the collection chamber will be homogenized using a small drill. Digestion buffers may be selected from PBS or TRIS with 2% Tween, salt concentrations (0 mmol/L, 200 mmol/L, or 1 mol/L NaCl) and nonfat dry milk (0 to 25%). In order to speed up digestion, it may be desirable to add enzymatic digestion by providing a proteinase such as collagenase.

In some embodiments, one or more protein extraction membranes may be used whereby the digested solution will be transferred to a protein extraction membrane. The solution will flow through the membrane collecting the purified protein. The membrane will contain pores between 0.5 nM to 0.5 μM and will be able to separate proteins that are smaller the 200 KDa. Since timing is important, vacuum may be used to increase the flow rate. A number of suitable protein extraction columns are known and can be adapted for use with certain embodiments of the present device, without undue experimentation. Following digestion, the food specimens flow from the protein extraction membrane to the two detection chambers 24a and 24b. The negative control chamber 24a contains a detection molecule (e.g., an aptamer) labeled with only a quencher molecule and the other chamber 24b containing the signaling polynucleotide (SPN) which is labeled with both a fluorescent marker and a quencher molecule. Once the purified protein enters each detection chamber the corresponding LEDs 26a and 26b will emit light and trigger excitation of the fluorophore.

In some embodiments, a universal protein extraction buffer that retrieve enough allergen protein (e.g., minimum 2 mg/ml total protein) for analysis from any food samples.

In other embodiments, various options for food sampling mechanisms, such as an Archimedes screw, vacuum pumps, and others, that will be efficient in multiple food matrices may be tested. These mechanisms will be tested on various food textures and optimized for a fast and simple one step procedure. In one embodiment, as described in Figures and below, an Archimedes screw mechanism holds the greatest potential. During the sample collection, a drill bit residing inside the needle is will be spun by a motor causing it to act as a screwpump. The "chip-clearing" action of the drill bit serves to capture pieces of the target sample and convey them from the collection needle in to the middle of the mixing chamber. Success will be defined by successfully acquiring 0.5 g samples from 25 20 different food matrices. Some examples of food matrices are listed in Table 7.

The light emitted from the molecules will transfer through a specific filter. The light transferred through the filter will be captured and translated to a digital signal that will activate the user interface. The control chamber will contain reagents that should produce a negative signal and this will be the background.

In some embodiments, each of the display windows 32a and 32b may comprise a screen that will display whether or not the sample tested contains the allergen. In some embodiments, it may be advantageous for the detection device to be operably linked, directly or wirelessly, to one or more databases. Based on the user preference the collected data could be shared with others. In some instances, data may be shared with other users or with those in the healthcare field.

The device 10 is designed to require minimal maintenance. It is expected that the LEDs 26a and 26b and the filter 28 will require replacement on a regular, e.g. annual, basis.

As noted above, another embodiment of a cartridge 1400 for use in the detection device of the present invention is now described with reference to FIGS. 2A and 2B. For the sake of simplicity, this embodiment of the cartridge does not show a pair of detection chambers as shown in FIG. 1. However, the skilled person will be able to modify the cartridge embodiment of FIGS. 2A and 2B to include a pair of detection chambers as shown in FIG. 1, without undue experimentation. Likewise, the cartridge 1400 of FIGS. 2A and 2B may be adapted to include other cartridge features shown in FIG. 1 and the skilled person will recognize that such variations and adaptations are within the scope of the present invention. For example, other embodiments of the device may be designed wherein the detection chamber(s) are located outside the cartridge or on a different cartridge. The function of the cartridge 1400 will be described concurrently with the introduction of its component parts.

Figure 2A:
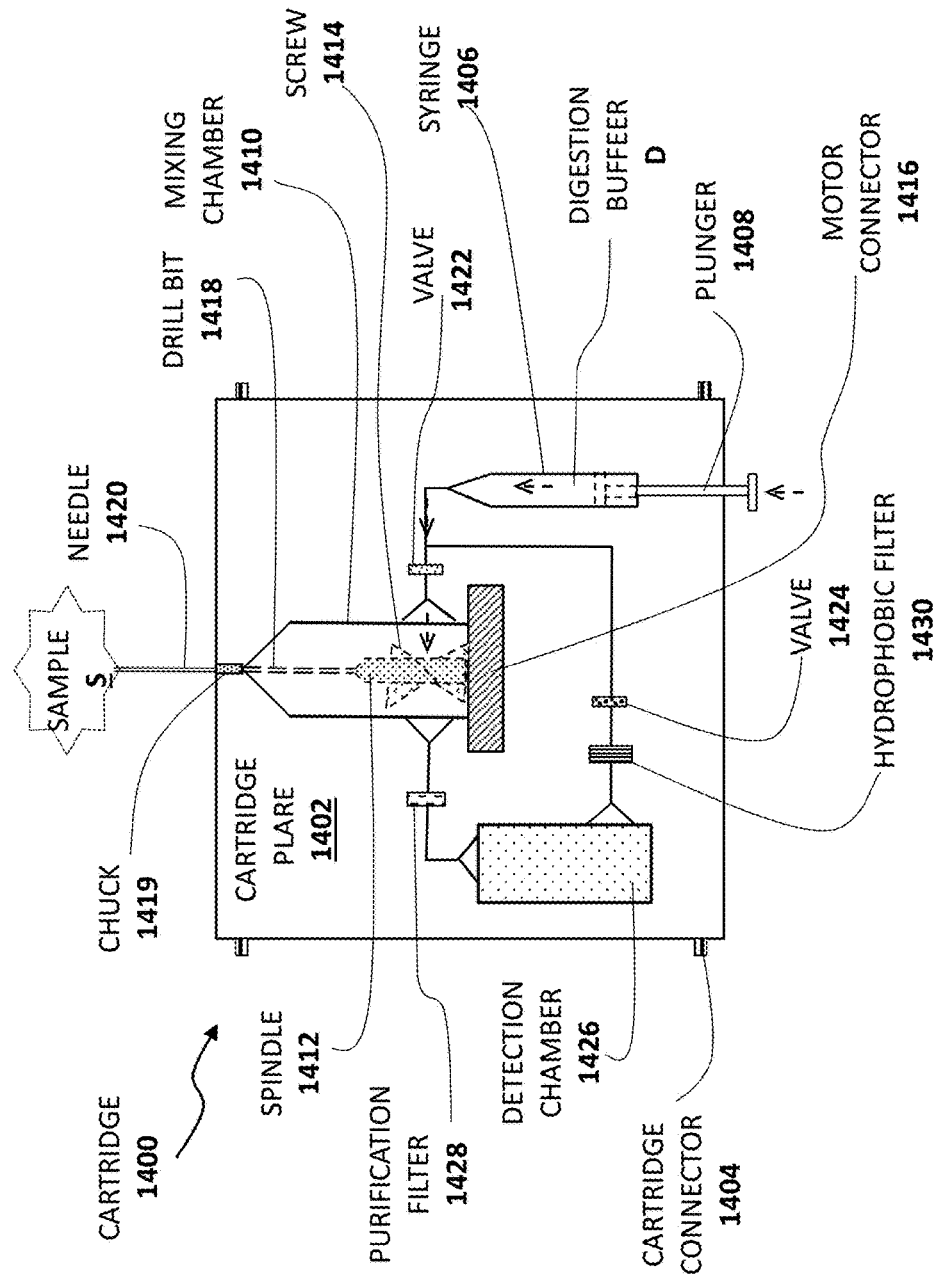
FIG. 2A is a schematic representation of a cartridge 1400 for use in another embodiment of the detection device of the present invention, which shows direction of flow of fluids within the cartridge upon depression of the syringe plunger 1408 into the barrel of the syringe 1406. Fluid (digestion buffer D) is injected through one-way valve 1422 into the mixing chamber 1410.

Turning now to FIGS. 2A and 2B, there is shown a cartridge 1400 for use with certain embodiments of the detection device of the present invention. The main body of the cartridge 1400 is provided by carrier plate 1402 which may be molded from plastic which is selected to be compatible with the buffers and other reagents used with the device. The components supported by the carrier plate 1402 which will be described hereinbelow, are attached to the carrier plate 1402 by known attachment or connector means, such as integrally-molded press-fit button arrangements and the like. Connections between electrical components for communication between processors and actuators, for example, may be made by conventional methods. Advantageously, the carrier plate 1402 contains a plurality of connectors 1404 which are configured to connect with corresponding parts on the main support body of the detection device (not shown). Such connectors 1404 may be formed during the process of manufacturing the carrier plate 1402 by processes such as injection molding.

Also attached to the carrier plate 1402 is a plunger-type syringe 1406. When retracted from the barrel of the syringe 1406, the plunger 1408 extends beyond the edge of the carrier plate 1402. The purpose of the syringe 1406 is to provide a means for injecting a digestion buffer D into the mixing chamber 1410, which, in the present embodiment, is substantially centered on the upper half of the carrier place 1402 in the orientation shown in FIGS. 2A and 2B. In certain embodiments, the syringe 1406 is physically actuated by depressing the plunger 1408 into the syringe barrel. In other embodiments, the syringe 1406 is automatically actuated under control of a processor (not shown). The design of processor-actuator systems for controlling valves and syringes in certain alternative embodiments of the cartridge is within the capabilities of the skilled person.

An Archimedes-type mixer (also known as a screwpump) is provided within the mixing chamber 1410. The mixer includes a spindle 1412 with a screw 1414 in the form of a helical conveyor for conveying helical mixing movement of the contents of the mixing chamber 1410. The spindle 1412 is turned by a motor (not shown) which is connected via a motor connector 1416.

In certain embodiments, the cartridge 1400 is disposable and the motor (not shown) which provides power to the mixing chamber is a modular unit which is removed from the motor connector 1416 prior to the disposal of the cartridge 1400 and attachable to a new cartridge to conserve the motor. In certain embodiments, the detection device may be provided with a motor bracket, clamp or holder to hold the motor in place on the body of the detection device while a used cartridge is removed and a new cartridge is replaced.

Connected to the end of the spindle 1412 is a hollow drill bit 1418 which terminates in a needle 1420. The needle 1420 is of a gauge sufficient to penetrate a sample S. Advantageously the chuck 1419 which secures the needle is adjustable and can therefore accommodate needles of various gauges in order to obtain samples from various materials. Likewise, the chuck 1419 may also accommodate various different sizes of drill bits. The action of the hollow drill bit 1418 conveys a portion of the sample S from the needle 1420, through the interior of the drill bit 1418 and into the interior of the mixing chamber 1410. After the portion of the sample S has been delivered to the mixing chamber 1410.

Digestion buffer D is conveyed to the mixing chamber 1410 by depressing the plunger 1408 of the syringe 1406 (as indicated by the arrows). A first one way valve 1422 is provided in the digestion buffer conduit which extends from the syringe 1406 to the right-hand port of the mixing chamber 1410. This first one-way valve 1422 prevents backflow of digestion buffer and other contents of the mixing chamber 1410 back into the syringe. The digestion buffer D breaks down the sample to release the target biomolecule for which the detection assay of the cartridge 1400 has been designed. After a mixing period which may be programmed by a processor (not shown) the left-hand port of the mixing chamber 1410 is programmed by the processor to open to allow digested sample to be conveyed through a second conduit to the detection chamber 1426 (in certain embodiments, the processor is a modular unit which may be removed prior to disposal of the cartridge 1400 in a manner similar to that described above for embodiments using a modular motor). In other embodiments, the processor is also disposable and is discarded along with the cartridge 1400. In other embodiments, a processor is not included and the movement of fluid within the conduits is induced solely by positive and negative pressure provided by depression and extension of the plunger 1408 in conjunction with the first and second one way valves 1422 and 1424. For example, as shown by the arrows in FIG. 2A, movement of the digestion buffer D from the syringe to the mixing chamber 1410 is effected by depressing the plunger 1408 into the barrel of the syringe 1406 and the one-way valve 1422 prevents back-flow as described above.

Now with reference to FIG. 2B, the arrows indicate the movement of fluids when the plunger 1408 of the syringe 1406 is withdrawn from the syringe barrel. It is seen that fluid is withdrawn from the detection chamber 1426 through the one way valve 1424 and to the barrel of the syringe 1406. Notably, one way valve 1422 prevents fluid from flowing to the syringe 1406 from the mixing chamber 1410.

Also provided in the conduit leading from the mixing chamber 1410 to the detection chamber 1426 is a purification filter 1428 for removal of at least some of the contaminants present in the digested sample. Such contaminants may include, for example, nucleic acids or digested fragments thereof. Such contaminants may have an adverse effect on proper functioning of the assay. In alternative embodiments, a plurality of such purification filters may be provided, each of which is selected to remove specific classes of contaminants which may be present in various different types of samples.

The conduit leading away from the detection chamber 1426 is provided with a hydrophobic filter 1430 which allows gases to escape from the detection chamber but prevents flow of fluid from the detection chamber 1426.

The unique configuration of the cartridge 1400 with its conduits forming a circulating loop with strategically placed filters 1428 and 1430 and one-way valves 1422 and 1424 allows syringe plunger 1408 to be withdrawn and depressed through several cycles to ensure that enough of the sample material is delivered to the detection chamber 1426. Furthermore, only a single precision stepper/control motor is required to provide sample transport. Alternative designs would require one motor to deliver the digestion buffer, and another motor to draw the sample into the detection chamber. The benefit of the design illustrated in FIGS. 2A and 2B is significant because an additional motor would increase the size, weight, cost, and power requirements for the detection device.

In operation of the cartridge 1400 in a detection device of one embodiment of the invention, an analysis is begun by inserting the sample collection needle 1420 into a target sample S. During sample collection, the drill bit 1418 residing inside the needle 1420 is spun by a motor causing it to turn the spindle 1412 and the screw 1414. The "chip-clearing" action of the drill bit 1418 serves to capture pieces of the target sample S and convey them from the collection needle into the middle of the mixing chamber 1410.

Once a piece of the target sample S is collected and delivered to the mixing chamber 1410, the syringe plunger 1408 is depressed. This forces the digestion buffer D through the one-way valve 1422 and into the mixing chamber 1410. It should be noted that the second one-way valve 1424 is oriented to prevent flow backwards into the detection chamber; its function will be reiterated below. Once the digestion buffer D is delivered to the mixing chamber 1410, the mixing motor spins the spindle 1412 according to prescribed time and speed profile to properly homogenize the sample S, freeing the constituent biomolecules of interest. The mixing motor is attached at the motor connector 1416, and it is the same motor that spins the drill bit 1418.

After the sample S is digested and homogenized, it is passed through the purification filter 1428 and into the detection chamber 1426. This may be effected by withdrawing the syringe plunger 1408. During this action, however, one-way valve 1422 serves to block material from exiting the mixing chamber backwards, and one-way valve 1424 opens to provide negative pressure across the purification filter 1428, thereby drawing the sample S into the detection chamber 1426. The hydrophobic filter 1430 allows interfering gas to escape while preventing the sample S from escaping, as noted above. When the sample S is in the detection chamber 1426, the analysis unit can perform interrogation of the sample S and report the measurement to the user.

Alternative embodiments of the cartridge 1400 shown in FIGS. 2A and 2B include a pair of detection chambers as described above for the embodiment of the device shown in FIG. 1.

Alternative embodiments may include a suction mechanism by which the syringe 1406 would be drawn to create a vacuum inside the mixing chamber 1410, thereby "sucking" the sample through the needle.

Alternative embodiments may also include a pumping mechanism by which the sample S is pushed into the chamber via gas (air) or fluid from a syringe-type device.

Alternative embodiments may also include a spring-loaded hook or harpoon-type mechanism for automatic deployment of a barb through the collection needle, followed by retraction of the collection needle back into the mixing chamber carrying a piece of the target sample. This approach is similar to the function of existing medical devices known as "biopsy guns."

Figure 3:
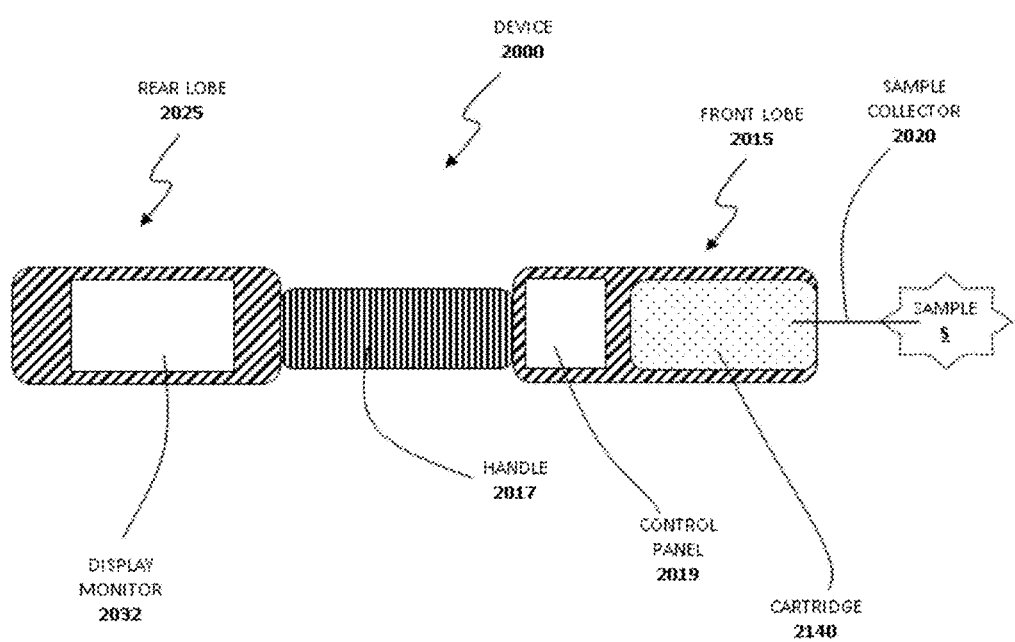
FIG. 3 shows another embodiment of the detection device 2000 which is in the general shape of an hourglass with a gripping handle 2017 disposed between its front and rear lobes (2015 and 2025, respectively).

An additional embodiment of the detection device is now described with reference to FIG. 3. This embodiment of the detection device 2000 is provided with a convenient ergonomic design for handling by a user using a single hand and is configured in an hourglass or barbell shape with a front-facing lobe shown generally at 2015. The front-facing lobe 2015 has a means for connecting to a cartridge 2140. When attached, the cartridge 2140 forms the majority visible portion of the forward facing lobe 2015. The forward facing lobe 2015 can be extended to point the sample collector 2020 toward a sample S for which an analysis is required. The narrow portion of the hourglass shape provides acts as a gripping handle 2017. When gripped in an overhand grip by a user, the thumb remains free to manipulate a control panel 2019 located on the device 2000 in close forward facing proximity to the handle 2017. The rear-facing lobe shown generally at 2025 provides support for the detection chamber which is hidden from view in the interior of the device 2000. The outer surface of the rear-facing lobe 2025 includes a display monitor 2032 which provides the analysis results.

This embodiment of the device 2000 is particularly well suited for analysis tasks involving analyses of many samples in a continuous manner. For example, this embodiment would be desired for use in quality control testing where many lots of a given product are analyzed. The ergonomic design minimizes discomfort to the user when being used for long periods of time. The device 2000 is extended to the sample S, a portion of the sample S is collected by the sample collector 2020, and processed in the mixing chamber of the cartridge 2140. The target molecule is released from the sample matrix and conveyed to the detection chamber and an analysis result is displayed on the display monitor 2032. In certain embodiments, the orientation of the display monitor 2032 can be adjusted for convenient viewing by either right-handed or left-handed users so that a simple elbow flexion movement will be sufficient to move the device 2000 from the sample collecting position to a position suitable for viewing the analysis result.

Allergens

According to the present invention, allergens include those from foods, the environment or from non-human proteins such as domestic pet dander.

Food allergens include, but are not limited to proteins in legumes such as peanuts, peas, lentils and beans, as well as the legume-related plant lupin, tree nuts such as almond, cashew, walnut, Brazil nut, filbert/hazelnut, pecan, pistachio, beechnut, butternut, chestnut, chinquapin nut, coconut, ginkgo nut, lychee nut, macadamia nut, nangai nut and pine nut, egg, fish, shellfish such as crab, crawfish, lobster, shrimp and prawns, mollusks such as clams, oysters, mussels and scallops, milk, soy, wheat, gluten, corn, meat such as beef, pork, mutton and chicken, gelatin, sulphite, seeds such as sesame, sunflower and poppy seeds, and spices such as coriander, garlic and mustard, fruits, vegetables such as celery, and rice. For example, the seeds from plants, such as lupin, sunflower or poppy can be used in foods such as seeded bread or can be ground to make flour to be used in making bread or pastries.

A recent review describes analytical strategies developed using aptamers for the control of pathogens, allergens, adulterants, toxins and other forbidden contaminants to ensure food safety (Amaya-Gonzalez, et al., *Aptamer-Based Analysis: A Promising Alternative for Food Safety Control*, Sensors, 2013, 13:16292-16311; Amaya-Gonzalez, et al., *Aptamer binding to coelic disease-triggering hydrophobic proteins: Towards a sensitive gluten detection system*. Anal. Chem. 2013, submitted). A method of detection of gluten is also described in PCT Publication PCT/ES2013/000133, 28 Jun. 2013, to Amaya-Gonzalez, et al.

Seafood allergens typically belong to a group of muscle proteins, including the parvalbumins in codfish and tropomyosin in crustaceans; other allergens such as arginine kinase and myosin light chain may also play an important part in allergenicity. Tropomyosin is the major allergen responsible for molecular and clinical cross-reactivity between crustaceans and molluscs, and is believed to be the allergen responsible in other inhaled invertebrates such as house dust mites and insects.

Detection Molecules: Aptamers

Detection molecules of the present invention include, but are not limited to any molecule or molecules which are capable of association or binding to one or more allergens.

In some embodiments, the detection molecules of the invention comprise one or more aptamers.

As used herein, an "aptamer" is a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function. In some cases, aptamers may also be peptide aptamers. As used herein, an "aptamer" specifically refers to a nucleic acid aptamer.

Aptamers, often called "chemical antibodies," have characteristics which are similar to those of antibodies. A typical nucleic acid aptamer is approximately 10-15 kDa in size (20-45 nucleotides), binds its target with at least nanomolar affinity, and discriminates against closely related targets.

Aptamers may be either monovalent or multivalent. Aptamers may be monomeric, dimeric, trimeric, tetrameric or higher multimeric. Individual aptamer monomers may be linked to form multimeric aptamer fusion molecules. As a non-limiting example, a linking oligonucleotide (i.e., linker) may be designed to contain sequences complementary to both 5'-arm and 3'-arm regions of random aptamers to form dimeric aptamers. For trimeric or tetrameric aptamers, a small trimeric or tetrameric (i.e., a Holiday junction-like) DNA nanostructure will be engineered to include sequences complementary to the 3'-arm region of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors.

Alternatively, multimeric aptamers can also be formed by mixing biotinylated aptamers with streptavidin.

As used herein, the term "multimeric aptamer" or "multivalent aptamer" refers to an aptamer that comprises multiple monomeric units, wherein each of the monomeric units can be an aptamer on its own. Multivalent aptamers have multivalent binding characteristics. A multimeric aptamer can be a homomultimer or a heteromultimer. The term "homomultimer" refers to a multimeric aptamer that comprises multiple binding units of the same kind, i.e., each unit binds to the same binding site of the same target molecule. The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sties or a multimeric aptamer that binds to different target molecules. A heteromultimer that binds to different target molecules can also be referred to as a multi-specific multimer.

Nucleic acid aptamers comprise a series of linked nucleosides or nucleotides. The term "nucleic acid," in its broadest sense, includes any compound and/or substance that comprise a polymer of nucleotides. These polymers are often referred to as polynucleotides. Exemplary nucleic acid molecules or polynucleotides of the invention include, but are not limited to, either D- or L-nucleic acids, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure, the ribofuranosyl ring or in the ribose-phosphate backbone.

Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid.

In some embodiments, the aptamer comprises at least one chemical modification. In some embodiments, the chemical modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In a preferred embodiment, the high molecular weight, non-immunogenic compound is polyalkylene glycol, and more preferably is polyethylene glycol (PEG). The process of covalent conjugation of PEG to another molecule, normally a drug or therapeutic protein is known as PEGylation. PEGylation is routinely achieved by incubation of a reactive derivative of PEG with the target molecule. The covalent attachment of PEG to a drug or therapeutic protein can mask the agent from the host's immune system, thereby providing reduced immunogenicity and antigenicity, and increase the hydrodynamic size (size in solution) of the agent which prolongs its circulatory time by reducing renal clearance. PEGylation can also provide water solubility to hydrophobic drugs and proteins.

In another preferred embodiment, the 3' cap is an inverted deoxythymidine cap.

In some embodiments, nucleic acid aptamers are provided in which the P(O)O group is replaced by P(O)S ("thioate"), P(S)S ("dithioate"), P(O)NR2 ("amidate"), P(O)R, P(O)OR', CO or CH2 ("formacetal") or 3'-amine (—NH—CH2—CH2-), wherein each R or R' is independently H or substituted or unsubstituted alkyl. Linkage groups can be attached to adjacent nucleotide through an —O—, —N—, or —S— linkage. Not all linkages in the nucleic acid aptamers are required to be identical.

As non-limiting examples, a nucleic acid aptamer can include D-ribose or L-ribose nucleic acid residues and can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, an inverted deoxynucleoside or inverted ribonucleoside, a 2'-deoxy-2'-fluoro-modified nucleoside, a 2'-amino-modified nucleoside, a 2'-alkyl-modified nucleoside, a morpholino nucleoside, a phosphoramidate or a non-natural base comprising nucleoside, or any combination thereof. Alternatively, a nucleic acid aptamer can comprise at least two modified ribonucleosides, at least 3, at least 4, at least 5, at least 6, at least 7, at least 8, at least 9, at least 10, at least 15, at least 20 or more modified ribonucleosides, up to the entire length of the molecule. The modifications need not be the same for each of such a plurality of modified deoxy- or ribonucleosides in a nucleic acid molecule.

Detection molecules which are nucleic acid based may include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, those disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993.

A suitable nucleotide length for an aptamer ranges from about 15 to about 100 nucleotides (nt), and in various other preferred embodiments, 15-30 nt, 20-25 nt, 30-100 nt, 30-60 nt, 25-70 nt, 25-60 nt, 40-60 nt, 25-40 nt, 30-40 nt, any of 22, 23, 24, 25, 26, 27, 28, 29, 30, 31, 32, 33, 34, 35, 36, 37, 38, 39 or 40 nt or 40-70 nt in length. However, the sequence can be designed with sufficient flexibility such that it can accommodate interactions of aptamers with two targets at the distances described herein.

In some embodiments, the nucleic acid aptamer comprises one or more regions of double-stranded character. Such double stranded regions may arise from internal self complementarity or complementarity with a second or further aptamers or oligonucleotide molecule. In some embodiments the double stranded region may be from 4-12, 4-10, 4-8 base pairs in length. In some embodiments the double stranded region may be 5, 6, 7, 8, 9, 10, 11 or 12 base pairs. In some embodiments the double stranded region may form a stem region. Such extended stem regions having double stranded character can serve to stabilize the nucleic acid aptamer. As used herein, the term "double stranded character" means that over any length of two nucleic acid molecules, their sequences form base pairings (standard or non standard) of more than 50 percent of the length.

Aptamers may be further modified to provide protection from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamers. For RNA aptamers, modified nucleotides such as substitutions of the 2'-OH groups of the ribose backbone, e.g., with 2'-deoxy-NTP or 2'-fluoro-NTP, can be incorporated into the RNA molecule using T7 RNA polymerase mutants. The resistance of these modified aptamers to nuclease can be tested by incubating them with either purified nucleases or nuclease from mouse serum, and the integrity of aptamers can be analyzed by gel electrophoresis.

In some embodiments, such modified nucleic acid aptamers may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modifications. For example, all purine nucleotides may have one type of modification (or are unmodified), while all pyrimidine nucleotides have another, different type of modification (or are unmodified). In this way, oligonucleotides, or libraries of oligonucleotides are generated using any combination of modifications as disclosed herein.

Some non-limiting examples of methods of detection include an assay for the direct detection of cancer cells using aptamer-conjugated gold nanoparticles (ACGNPs) selective for cell surface molecules on CCRF-CEM cells (CCL-119 T-cell, human acute lymphoblastic leukemia) and Ramos cells (CRL-1596, B-cell, human Burkitt's lymphoma) (Medley, et al., *Gold Nanoparticle-Based Colorimetric Assay for the Direct Detection of Cancerous Cells*. Anal. Chem. 2008, 80:1067-1072); the use of aptamer-linked gold nanoparticles (AuNPs) that undergo fast disassembly into red dispersed nanoparticles upon binding of target analytes (Lu, et al. Chapter 14: Nanoparticles/Dip Stick, in *Nucleic Acid and Peptide Aptamers: Methods and Protocols*, Günter Mayer (ed.). 535:223-239); and a differential pulse voltammetry (DPV)-based biosensor employing aptamer-AuNP conjugates as the sandwich-amplification element for the ultrasensitive detection of IgE in human serum (over a range 1-10,000 ng/mL with an LOD as low as 0.52 ng/mL) (Wang, et al., *Aptamer-Au NPs conjugates-accumulated methylene blue for the sensitive electrochemical immunoassay of protein*, Talanta, 15 Apr. 2010, 81(1-2):63-67).

However, at least one disadvantage shared by many electrochemical biosensors is the off-line nature of the measurements, requiring long incubation times with analyte solution, rather than real-time detection (Pilloli, et al., *Advances in biosensor development based on integrating nanotechnology and applied to food-allergen management*. Trends in Analytical Chemistry, June 2013, 47:12-26).

Detection Molecules: Antibodies

In some embodiments, the detection molecules of the invention comprise an antibody. As used herein, the term "antibody" is used in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies are primarily amino-acid based molecules but may also comprise one or more modifications such as with sugar moieties.

"Antibody fragments" comprise a portion of an intact antibody, preferably comprising an antigen binding region thereof. Examples of antibody fragments include Fab, Fab', F(ab')2, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')2 fragment that has two antigen-binding sites and is still capable of cross-linking antigen. Detection molecules may comprise one or more of these fragments. For the purposes herein, an "antibody" may comprise a heavy and light variable domain as well as an Fc region.

"Native antibodies" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains that differ extensively in sequence among antibodies and are used in the binding and specificity of each particular antibody for its particular antigen. As used herein, the term "Fv" refers to antibody fragments which contain a complete antigen-recognition and antigen-binding site. This region consists of a dimer of one heavy chain and one light chain variable domain in tight, non-covalent association.

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

"Single-chain Fv" or "scFv," as used herein, refers to a fusion protein of VH and VL antibody domains, wherein these domains are linked together into a single polypeptide chain. In some embodiments, the Fv polypeptide linker enables the scFv to form the desired structure for antigen binding.

The term "diabodies" refers to small antibody fragments with two antigen-binding sites, which fragments comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "monoclonal antibody" as used herein refers to an antibody obtained from a population of substantially homogeneous cells (or clones), i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity.

The term "hypervariable region" when used herein in reference to antibodies refers to regions within the antigen binding domain of an antibody comprising the amino acid residues that are responsible for antigen binding. The amino acids present within the hypervariable regions determine the structure of the complementarity determining region (CDR). As used herein, the "CDR" refers to the region of an antibody that comprises a structure that is complimentary to its target antigen or epitope.

In some embodiments, the compositions of the present invention may be antibody mimetics. The term "antibody mimetic" refers to any molecule which mimics the function or effect of an antibody and which binds specifically and with high affinity to their molecular targets. As such, antibody mimics include nanobodies and the like.

In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure and/or function comprising some differences in their amino acid sequence, composition or structure as compared to a native antibody.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

In one embodiment, detection molecules comprising antibodies, antibody fragments, their variants or derivatives as described above are specifically immunoreactive with allergens. Detection molecules comprising antibodies or fragments of antibodies may also bind to target sites on allergens.

Antibodies of the present invention may be characterized by their target molecule(s), by the antigens used to generate them, by their function (whether as agonists or antagonists) and/or by the cell niche in which they function.

Measures of antibody function may be made relative to a standard under normal physiologic conditions, in vitro or in vivo. Measurements may also be made relative to the presence or absence of the antibodies. Such methods of measuring include standard measurement in tissue or fluids such as serum or blood such as Western blot, enzyme-linked immunosorbent assay (ELISA), activity assays, reporter assays, luciferase assays, polymerase chain reaction (PCR) arrays, gene arrays, real time reverse transcriptase (RT) PCR and the like.

Detection molecule antibodies may bind or interact with any number of locations on or along an allergen protein. Allergen antibody target sites contemplated include any and all possible sites for detecting said allergen.

Detection molecule compounds of the present invention exert their effects via binding (reversibly or irreversibly) to one or more allergen target sites. While not wishing to be bound by theory, target sites which represent a binding site for an antibody, are most often formed by proteins or protein domains or regions. However, target sites may also include biomolecules such as sugars, lipids, nucleic acid molecules or any other form of binding epitope.

Detection molecule antibodies of the present invention, as well as antigens used to generate them, are primarily amino acid-based molecules. These molecules may be "peptides," "polypeptides," or "proteins."

As used herein, the term "peptide" refers to an amino-acid based molecule having from 2 to 50 or more amino acids. Special designators apply to the smaller peptides with "dipeptide" referring to a two amino acid molecule and "tripeptide" referring to a three amino acid molecule. Amino acid based molecules having more than 50 contiguous amino acids are considered polypeptides or proteins.

The terms "amino acid" and "amino acids" refer to all naturally occurring L-alpha-amino acids as well as non-naturally occurring amino acids. Amino acids are identified by either the one-letter or three-letter designations as follows: aspartic acid (Asp: D), isoleucine (Ile: I), threonine (Thr: T), leucine (Leu: L), serine (Ser: S), tyrosine (Tyr: Y), glutamic acid (Glu: E), phenylalanine (Phe: F), proline (Pro: P), histidine (His: H), glycine (Gly: G), lysine (Lys: K), alanine (Ala: A), arginine (Arg: R), cysteine (Cys: C), tryptophan (Trp: W), valine (Val: V), glutamine (Gln: Q) methionine (Met: M), and asparagine (Asn: N), where the amino acid is listed first followed parenthetically by the three and one letter codes, respectively.

Antibodies: Manufacture

Antibodies of the present invention may be polyclonal or monoclonal or recombinant, produced by methods known in the art or as described in this application.

In some embodiments, the antibodies of the present invention may be labeled for purposes of detection with a detectable label known by one of skill in the art. The label can be a radioisotope, fluorescent compound, chemiluminescent compound, enzyme, or enzyme co-factor, or any other labels known in the art. In some aspects, the antibody that binds to a desired antigen is not labeled, but may be detected by binding of a labeled secondary antibody that specifically binds to the primary antibody.

Antibodies of the present invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. Antibodies of the present invention can be from any animal origin including birds and mammals. Preferably, such antibodies are of human, murine (e.g., mouse and rat), donkey, sheep, rabbit, goat, guinea pig, camel, horse, or chicken origin. The antibodies of the present invention can be monospecific or multispecific (e.g., bispecific, trispecific, or of greater multispecificity). Multispecific antibodies can be specific for different epitopes of a peptide of the present invention, or can be specific for both a peptide of the present invention, and a heterologous epitope, such as a heterologous peptide or solid support material. (See, e.g., WO 93/17715; WO 92/08802; WO 91/00360; WO 92/05793; Tutt, A. et al., *Trispecific F(ab)3 derivatives that use cooperative signaling via the TCR/CD3 complex and CD2 to activate and redirect resting cytotoxic T cells*. J Immunol. 1991 Jul. 1; 147(1): 60-9; U.S. Pat. Nos. 4,474,893; 4,714,681; 4,925,648; 5,573,920; 5,601,819; and Kostelny, S. A. et al., *Formation of a bispecific antibody by the use of leucine zippers*. J Immunol. 1992 Mar. 1; 148(5):1547-53). For example, the antibodies may be produced against a peptide containing repeated units of a peptide sequence of the present invention, or they may be produced against a peptide containing two or more peptide sequences of the present invention, or the combination thereof.

As a non-limiting example, a heterobivalent ligand (HBL) system that competitively inhibits allergen binding to mast cell bound IgE antibody, thereby inhibiting mast cell degranulation, has been designed (Handlogten, et al., *Design of a Heterobivalent Ligand to Inhibit IgE Clustering on Mast Cells*, Chemistry & Biology, 2011 Sep. 23, 18(9):1179-1188).

In some embodiments, antibodies can be prepared from any region of an allergen. In the present invention, the peptides for generating antibodies preferably contain a sequence of at least 4, at least 5, at least 6, at least 7, more preferably at least 8, at least 9, at least 10, at least 11, at least 12, at least 13, at least 14, at least 15, and, preferably, between about 5 to about 50 amino acids in length, more preferably between about 10 to about 30 amino acids in length, even more preferably between about 10 to about 20 amino acids in length.

In certain embodiments of the present invention, where larger polypeptides or proteins are used for generating antibodies, these preferably are at least 50, at least 55, at least 60, at least 70, at least 80, at least 90, or more amino acids in length.

Monoclonal antibodies of the present invention can be prepared using well-established methods known by those skilled in the art. In one embodiment, the monoclonal antibodies are prepared using hybridoma technology (Kohler, G. et al., *Continuous cultures of fused cells secreting antibody of predefined specificity*. Nature. 1975 Aug. 7: 256 (5517): 495-7). In a hybridoma method, a mouse, hamster, or other appropriate host animal, is typically immunized with an immunizing agent (e.g., a peptide of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, J. W., *Monoclonal Antibodies: Principles and Practice*. Academic Press. 1986; 59-1031). Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, D. et al., *A human hybrid myeloma for production of human monoclonal antibodies*. J Immunol. 1984 December; 133(6): 3001-5; Brodeur, B. et al., *Monoclonal Antibody Production Techniques and Applications*. Marcel Dekker, Inc., New York. 1987; 33:51-63).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (MA) or enzyme-linked immunosorbent assay (ELISA). Such techniques and assays are known by those skilled in the art. The binding specificity of the monoclonal antibody can, for example, be determined by Scatchard analysis (Munson, P. J. et al., *Ligand: a versatile computerized approach for characterization of ligand-binding systems*. Anal Biochem. 1980 Sep. 1; 107(1):220-39).

After the desired hybridoma cells are identified, the clones may be subcloned by limiting dilution procedures and grown by standard methods. Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In another embodiment, the monoclonal antibodies of the present invention can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In another embodiment, antibodies of the present invention can also be produced by various procedures known by those skilled in the art. For the production of polyclonal antibodies in vivo, host animals, such as rabbits, rats, mice, sheep, or goats, are immunized with either free or carrier-coupled peptides, for example, by intraperitoneal and/or intradermal injection. Injection material is typically an emulsion containing about 100 µg of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and other useful human adjuvants such as BCG (*Bacillus* Calmette-Guerin) and *Corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Detection molecules comprising antibodies, variants and fragments thereof may be selected and produced using high throughput methods of discovery. In one embodiment, Detection molecules comprising synthetic antibodies, variants and fragments thereof are produced through the use of display libraries. The term "display" as used herein, refers to the expression or "display" of proteins or peptides on the surface of a given host. The term "library" as used herein, refers to a collection of unique cDNA sequences. A library may contain from as little as two unique cDNAs to hundreds of billions of unique cDNAs. In a preferred embodiment, Detection molecules comprising synthetic antibodies are produced using antibody display libraries or antibody fragment display libraries. The term "antibody fragment display library" as used herein, refers to a display library wherein each member encodes an antibody fragment containing at least one variable region of an antibody. Such antibody fragments are preferably Fab fragments, but other antibody fragments such as single-chain variable fragments (scFvs) are contemplated as well. In an Fab antibody fragment library, each Fab encoded may be identical except for the amino acid sequence contained within the variable loops of the complementarity determining regions (CDRs) of the Fab fragment. In an alternative or additional embodiment, amino acid sequences within the individual VH and/or VL regions may differ as well.

Display libraries may be expressed in a number of possible hosts including, but not limited to yeast, bacteriophage, bacteria and retroviruses. Additional display technologies that may be used include ribosome-display, microbead-display and protein-DNA linkage techniques. In a preferred embodiment, Fab display libraries are expressed in yeast or in bacteriophages (also referred to herein as "phages" or "phage particles." When expressed, the Fabs decorate the surface of the phage or yeast where they can interact with a given antigen. An antigen comprising an allergen or an antigen from a desired target site may be used to select phage particles or yeast cells expressing antibody fragments with the highest affinity for that antigen. The DNA sequence encoding the CDR of the bound antibody fragment can then be determined through sequencing using the bound particle or cell. In one embodiment, positive selection is used in the development of antibodies. As used herein, the term "positive selection" refers to processes by which antibodies and/or fragments thereof are selected from display libraries based on affinity for antigens containing target sites. In some embodiments, negative selection is utilized in the development of antibodies. As used herein, the term "negative selection" refers to processes by which antigens that lack target sites for antibody production are used to exclude antibodies and/or fragments thereof from a given display library during antibody development. In some embodiments, both positive and negative selection processes are utilized during multiple rounds of selection in the development of antibodies using display libraries.

In yeast display, cDNA encoding different antibody fragments are introduced into yeast cells where they are expressed and the antibody fragments are "displayed" on the cell surface as described by Chao et al. (Chao, G. et al.,

*Isolating and engineering human antibodies using yeast surface display*. Nat Protoc. 2006; 1(2):755-68). In yeast surface display, expressed antibody fragments contain an additional domain comprising the yeast agglutinin protein, Aga2p. This domain allows the antibody fragment fusion protein to attach to the outer surface of the yeast cell through the formation of disulfide bonds with surface-expressed Aga1p. The result is a yeast cell, coated in a particular antibody fragment. Display libraries of cDNA encoding these antibody fragments are utilized initially in which the antibody fragments each have a unique sequence. These fusion proteins are expressed on the cell surface of millions of yeast cells where they can interact with a desired antigenic target peptide, incubated with the cells. Target peptides may be covalently or otherwise modified with a chemical or magnetic group to allow for efficient cell sorting after successful binding with a suitable antibody fragment takes place. Recovery may be by way of magnetic-activated cell sorting (MACS), fluorescence-activated cell sorting (FACS) or other cell sorting methods known in the art. Once a subpopulation of yeast cells is selected, the corresponding plasmids may be analyzed to determine the CDR sequence.

Bacteriophage display methods typically utilize filamentous phage including fd, F1 and M13 virions. Such strains are non-lytic, allowing for continued propagation of the host and increased viral titres. Examples of phage display methods that can be used to make the antibodies of the present invention include those disclosed in Miersch et al. (Miersch, S. et al., *Synthetic antibodies: Concepts, potential and practical considerations*. Methods. 2012 August; 57(4): 486-98), Bradbury et al. (Bradbury, A. R. et al., *Beyond natural antibodies: the power of in vitro display technologies*. Nat Biotechnol. 2011 March; 29(3):245-54), Brinkman et al. (Brinkmann, U. et al., *Phage display of disulfide-stabilized Fv fragments*. J Immunol Methods. 1995 May 11; 182(1):41-50); Ames et al. (Ames, R. S. et al., *Conversion of murine Fabs isolated from a combinatorial phage display library to full length immunoglobulins*. J Immunol Methods. 1995 Aug. 18; 184(2):177-86); Kettleborough et al. (Kettleborough, C. A. et al., *Isolation of tumor cell-specific single-chain Fv from immunized mice using phage-antibody libraries and the re-construction of whole antibodies from these antibody fragments*. Eur J Immunol. 1994 April; 24(4):952-8); Persic et al. (Persic, L. et al., *An integrated vector system for the eukaryotic expression of antibodies or their fragments after selection from phage display libraries*. Gene. 1997 Mar. 10; 187(1):9-18); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5, 969,108, each of which is incorporated herein by reference in its entirety.

Antibody fragment expression on bacteriophages may be carried out by inserting the cDNA encoding the fragment into the gene expressing a viral coat protein. The viral coat of filamentous bacteriophages is made up of five coat proteins, encoded by a single-stranded genome. Coat protein pIII is the preferred protein for antibody fragment expression, typically at the N-terminus. If antibody fragment expression compromises the function of pIII, viral function may be restored through coexpression of a wild type pIII, although such expression will reduce the number of antibody fragments expressed on the viral coat, but may enhance access to the antibody fragment by the target antigen. Expression of viral as well as antibody fragment proteins may alternatively be encoded on multiple plasmids. This method may be used to reduce the overall size of infective plasmids and enhance the transformation efficiency.

As described above, after selection of a host expressing a high affinity antibody or antibody fragment, the coding regions from the antibody or antibody fragment can be isolated and used to generate whole antibodies, including human antibodies, or any other desired antigen binding fragment, and expressed in any desired host, including mammalian cells, insect cells, plant cells, yeast, and bacteria, e.g., as described in detail below.

The DNA sequence encoding a high affinity antibody can be mutated for additional rounds of selection in a process known as affinity maturation. The term "affinity maturation," as used herein, refers to a method whereby antibodies are produced with increasing affinity for a given antigen through successive rounds of mutation and selection of antibody- or antibody fragment-encoding cDNA sequences. In a preferred embodiment, this process is carried out in vitro. To accomplish this, amplification of CDR coding sequences may be carried out using error-prone PCR to produce millions of copies containing mutations including, but not limited to point mutations, regional mutations, insertional mutations and deletional mutations. As used herein, the term "point mutation" refers to a nucleic acid mutation in which one nucleotide within a nucleotide sequence is changed to a different nucleotide. As used herein, the term "regional mutation" refers to a nucleic acid mutation in which two or more consecutive nucleotides are changed to different nucleotides. As used herein, the term "insertional mutation" refers to a nucleic acid mutation in which one or more nucleotides are inserted into a nucleotide sequence. As used herein, the term "deletional mutation" refers to a nucleic acid mutation in which one or more nucleotides are removed from a nucleotide sequence. Insertional or deletional mutations may include the complete replacement of an entire codon or the change of one codon to another by altering one or two nucleotides of the starting codon.

Mutagenesis may be carried out on CDR-encoding cDNA sequences to create millions of mutants with singular mutations in CDR heavy and light chain regions. In another approach, random mutations are introduced only at CDR residues most likely to improve affinity. These newly generated mutagenic libraries can be used to repeat the process to screen for clones that encode antibody fragments with even higher affinity for the target peptide. Continued rounds of mutation and selection promote the synthesis of clones with greater and greater affinity (Chao, G. et al., *Isolating and engineering human antibodies using yeast surface display*. Nat. Protoc. 2006; 1(2):755-68).

Examples of techniques that can be used to produce antibodies and antibody fragments, such as Fabs and scFvs, include those described in U.S. Pat. Nos. 4,946,778 and 5,258,498; Miersch et al. (Miersch, S. et al., *Synthetic antibodies: Concepts, potential and practical considerations*. Methods. 2012 August; 57(4):486-98), Chao et al. (Chao, G. et al., *Isolating and engineering human antibodies using yeast surface display*. Nat Protoc. 2006; 1(2):755-68), Huston et al. (Huston, J. S. et al., *Protein engineering of single-chain Fv analogs and fusion proteins*. Methods Enzymol. 1991; 203:46-88); Shu et al. (Shu, L. et al., *Secretion of a single-gene-encoded immunoglobulin from myeloma cells*. Proc. Natl. Acad. Sci. U.S.A 1993 Sep. 1; 90(17): 7995-9); and Skerra et al. (Skerra, A. et al., *Assembly of a functional immunoglobulin Fv fragment in Escherichia coli*.

Science. 1988 May 20; 240(4855):1038-41), each of which is incorporated herein by reference in its entirety.

For some uses, including the in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (Morrison, S. L., *Transfectomas provide novel chimeric antibodies*. Science. 1985 Sep. 20; 229(4719):1202-7; Gillies, S. D. et al., High-level expression of chimeric antibodies using adapted cDNA variable region cassettes. J Immunol Methods. 1989 Dec. 20; 125 (1-2):191-202; and U.S. Pat. Nos. 5,807,715; 4,816,567; and 4,816,397, which are incorporated herein by reference in their entirety).

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (U.S. Pat. Nos. 5,693,762 and 5,585,089; Riechmann, L. et al., *Reshaping human antibodies for therapy*. Nature. 1988 Mar. 24; 332(6162):323-7, which are incorporated herein by reference in their entireties).

Antibodies can be humanized using a variety of techniques known in the art, including, for example, CDR-grafting (EP 239,400; PCT publication WO 91/09967; U.S. Pat. Nos. 5,225,539; 5,530,101; and 5,585,089); veneering or resurfacing (EP 592,106; EP 519,596; Padlan, E. A., *A possible procedure for reducing the immunogenicity of antibody variable domains while preserving their ligand-binding properties*. Mol Immunol. 1991 April-May; 28(4-5):489-98; Studnicka, G. M. et al., *Human-engineered monoclonal antibodies retain full specific binding activity by preserving non-CDR complementarity-modulating residues*. Protein Eng. 1994 June; 7(6):805-14; Roguska, M. A. et al., *Humanization of murine monoclonal antibodies through variable domain resurfacing*. Proc. Natl. Acad. Sci. U.S.A 1994 Feb. 1; 91(3):969-73); and chain shuffling (U.S. Pat. No. 5,565,332); each of which is incorporated herein by reference in their entirety.

Completely human antibodies are particularly desirable for therapeutic treatment of human patients, so as to avoid or alleviate immune reaction to foreign protein. Human antibodies can be made by a variety of methods known in the art, including the antibody display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Thus, using such a technique, it is possible to produce useful human IgG, IgA, IgM, IgD and IgE antibodies. For an overview of the technology for producing human antibodies, see Lonberg and Huszar (Lonberg, N. et al., *Human antibodies from transgenic mice*. Int. Rev. Immunol. 1995; 13(1):65-93). For a detailed discussion of the technology for producing human antibodies and human monoclonal antibodies and protocols for producing such antibodies, see, e.g., PCT publications WO 98/24893; WO 92/01047; WO 96/34096; WO 96/33735; U.S. Pat. Nos. 5,413,923; 5,625, 126; 5,633,425; 5,569,825; 5,661,016; 5,545,806; 5,814, 318; 5,885,793; 5,916,771; 5,939,598; 6,075,181; and 6,114, 598, each of which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the present invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Variations of Detection Molecules

Detection molecules which are amino acid based may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multimolecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

According to certain embodiments of the present invention, variants of detection molecules are provided.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

The term "polynucleotide variant" refers to molecules which differ in their nucleic sequence from a native or reference sequence. The nucleic acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids (or nucleic acids) which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences (or nucleic acid sequences) of the detection molecules of the invention may comprise naturally occurring amino acids (or nucleic acids). Alternatively, the detection molecules may comprise naturally and non-naturally occurring amino acids or non-naturally occurring nucleic acids).

The term "amino acid sequence variant" refers to molecules with some differences in their amino acid sequences as compared to a native or starting sequence. The term "nucleic acid sequence variant" refers to molecules with some differences in their nucleic acid sequences as compared to a native or starting sequence. The sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least about 70% homology to a native sequence, and preferably, they will be at least about 80%, more preferably at least about 90% homologous to a native sequence.

"Homology" as it applies to amino acid or nucleic acid sequences is defined as the percentage of residues in the candidate sequence that are identical with the residues in the sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid or nucleic acid sequences is meant the corresponding sequence of other species having substantial identity to a second sequence of a second species.

The term "analogs" is meant to include polypeptide or polynucleotide variants which differ by one or more amino acid or nucleic acid alterations, respectively, e.g., substitutions, additions or deletions of residues that still maintain the properties of the parent polypeptide or polynucleotide.

The term "derivative" is used synonymously with the term "variant" and refers to a molecule that has been modified or changed in any way relative to a reference molecule or starting molecule.

The present invention contemplates several types of detection molecules which are amino acid or nucleic acid based including variants and derivatives. These include substitutional, insertional, deletion and covalent variants and derivatives. As such, included within the scope of this invention are detection molecules containing substitutions, insertions and/or additions, deletions and covalent modifications.

For proteins for example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" are those that have at least one amino acid residue or at least one nucleoside (or nucleotide) in a native or starting sequence removed and a different amino acid or nucleoside (or nucleotide) inserted in its place at the same position. The substitutions may be single, where only one amino acid or nucleoside (or nucleotide) in the molecule has been substituted, or they may be multiple, where two or more amino acids or nucleosides (or nucleotides) have been substituted in the same molecule.

As used herein the term "conservative amino acid substitution" in the context of polypeptides refers to the substitution of an amino acid that is normally present in the sequence with a different amino acid of similar size, charge, or polarity.

Examples of conservative substitutions in peptides or proteins include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" are those variants with one or more amino acids or nucleosides (or nucleotides) inserted immediately adjacent to an amino acid or nucleoside (or nucleotide) at a particular position in a native or starting sequence. "Immediately adjacent" to an amino acid or nucleotide means connected to either the alpha-carboxy or alpha-amino functional group of the amino acid; and means directly to the 5' or 3' of the instant nucleoside or nucleotide of the polynucleotide.

"Deletional variants", are those with one or more amino acids or nucleosides (or nucleotides) in the native or starting sequence removed. Ordinarily, deletional variants will have one or more amino acids or nucleosides (or nucleotides) deleted in a particular region of the molecule.

The term "derivatives," as referred to herein, includes modifications of a native or starting protein or polynucleotide with an organic proteinaceous or non-proteinaceous derivatizing agent. Protein derivatives may also include post-translational modifications. Covalent modifications are traditionally introduced by reacting targeted amino acid or nucleoside (or nucleotide) residues of the molecule with an organic derivatizing agent that is capable of reacting with selected atoms or residues, or in the case of proteins by harnessing mechanisms of post-translational modifications that function in selected recombinant host cells. Such modifications are within the ordinary skill in the art and are performed without undue experimentation.

Covalent derivatives specifically include fusion molecules in which proteins are covalently bonded to a non-proteinaceous polymer. The non-proteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol. The proteins may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337, each of which is incorporated herein by reference in entirety.

"Features" are defined as distinct amino acid or nucleoside (or nucleotide) sequence-based components of a molecule. Features of the Detection molecules of the certain embodiments of the present invention include surface manifestations, local conformational shape, folds, loops, half-loops, domains, half-domains, sites, termini or any combination thereof.

As used herein the term "surface manifestation" refers to a component of a protein or polynucleotide appearing on an outermost surface.

As used herein the term "local conformational shape" means a structural manifestation which is located within a definable space of the protein or polynucleotide.

As used herein the term "fold" means the resultant conformation of an amino acid or nucleoside (or nucleotide) sequence upon energy minimization. A fold may occur at the secondary or tertiary level of the folding process. Examples of secondary level folds in proteins include beta sheets and alpha helices. Examples of tertiary folds in proteins include domains and regions formed due to aggregation or separation of energetic forces. Regions formed in this way include hydrophobic and hydrophilic pockets, and the like.

As used herein with respect to polypeptides and polynucleotides the term "turn" means a bend which alters the direction of the backbone of a polypeptide or polynucleotide and may involve one, two, three or more amino acid or nucleoside (or nucleotide) residues.

As used herein the term "loop" refers to a structural feature of a polypeptide or polynucleotide which reverses the direction of the backbone of the sequence and comprises four or more amino acid or nucleoside (or nucleotide) residues. Oliva et al. have identified at least 5 classes of protein loops (J. Mol. Biol. 266 (4): 814-830; 1997).

As used herein when referring to proteins the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein the term "domain" refers to a motif of a polypeptide or polynucleotide having one or more identifiable structural or functional characteristics or properties (e.g., binding capacity, serving as a site for molecular interactions.

As used herein, the terms "site" as it pertains to amino acid or nucleoside (or nucleotide) based embodiments is used synonymous with "amino acid residue" and "nucleic acid residue." A site represents a position within a polypeptide or polynucleotide that may be modified, manipulated, altered, derivatized or varied within the polypeptide or polynucleotide based molecules of the present invention.

As used herein the terms "termini" or "terminus" refers to an extremity of a polypeptide or polynucleotide. Such extremity is not limited only to the first or final site of the polypeptide or polynucleotide but may include additional amino acids or nucleosides (or nucleotides) in the terminal regions. The polypeptide based molecules of the present invention may be characterized as having both an N-terminus (terminated by an amino acid with a free amino group (—NH2)) and a C-terminus (terminated by an amino acid with a free carboxyl group (—COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate. The polynucleotide based molecules of the present invention may be characterized as having both a 5' terminus and a 3' terminus.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention.

For example, a manipulation which involved deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Isotopic Variations

The detection molecules of the present invention may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. The detection molecules may be deuterated in order to change a physical property of the compound, such as stability, or to allow the compounds to be used in diagnostic and experimental applications.

Conjugates and Combinations

It is contemplated by the present invention that the detection molecules, antigens and/or antibodies of certain embodiments of the present invention may be complexed, conjugated or combined with one or more homologous or heterologous molecules. As used herein, "homologous molecule" means a molecule which is similar in at least one of structure or function relative to a starting molecule while a "heterologous molecule" is one that differs in at least one of structure or function relative to a starting molecule. Structural homologs are therefore molecules which are substantially structurally similar. They can be identical. Functional homologs are molecules which are substantially functionally similar. They can be identical.

Detection molecules of the invention may comprise conjugates. Such conjugates of the invention may include a naturally occurring substance or ligand, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Examples of polyamines include: polyethyleneimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Detection molecules of certain embodiments of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

Conjugating moieties may be added to the detection molecule antibodies such that they allow labeling or flagging an allergen. Such tagging/flagging molecules include, but are not limited to ubiquitin, fluorescent molecules, biotin, avidin, streptavidin, horseradish peroxidase (HRP) and digoxigenin.

In some embodiments, detection molecules may be combined with other detection molecules.

In some embodiments, the detection molecule may comprise a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., 18F, 67Ga, 81mKr, 82Rb, 111In, 123I, 133Xe, 201Tl, 125I, 35S, 14C, 3H, or 99mTc (e.g., as pertechnetate (technetate(VII), TcO4)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'-disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), dichlorotriazin-2-yl)aminofluorescein (DTAF), 2',7'-dimethoxy-4',5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with N,N-diethylethanamine(1:1) (IR144);

5-chloro-2-[2-[3-[(5-chloro-3-ethyl-2(3H)-benzothiazol-ylidene)ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-X-rhodanine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In some embodiments, the non-detectable precursor comprises a combination of a fluorophore and a quencher, such as the combination of fluorescein and DABCYL, for example. Guidelines for selection of fluorophore and quencher pairs are described in S.A.E. Marras *Selection of Fluorophore and Quencher Pairs for Fluorescent Nucleic Acid Hybridization Probes* in Didenko, Vladimir V., ed. *Fluorescent energy transfer nucleic acid probes: designs and protocols.* Vol. 335. Springer, 2006, which is incorporated herein by reference in entirety. In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (MA), and Western blot analysis.

Signaling Polynucleotides

In accordance with certain embodiments, there are provided polynucleotide sequences that are detectable when bound at high affinity and specificity to molecular targets. Such polynucleotide sequences may be produced using the SELEX process as described hereinabove.

In certain types of exemplary signaling polynucleotides, the 5' end of the sequence is bound to a fluorescent molecule and the 3' end carries a 5-20 nucleotide long reverse-complement sequence that binds to the 5'-end. This results of folding of the sequence and formation of a stem-loop structure. A quencher molecule is bound to the 3'-end. The skilled person will recognize that alternative arrangements are possible wherein the quencher is bound to the 5'-end and the fluorophore is bound to the 3'-end. Such alternative signaling polynucleotides may be prepared by the skilled person in context of the present description without undue experimentation.

An exemplary signaling polynucleotide designed with a stem-loop structure for binding to lysozyme as a molecular target will be described hereinbelow.

In certain embodiments, the fluorophore molecule at the 5'-end is bound to a T nucleotide residue in order to prevent quenching caused by a G nucleotide residue.

In recognition that higher melting temperatures (Tm) are to be avoided, the Tm or $\Delta G$ of the two strands will need to be lower than the binding affinity of the molecular target in order for the signaling polynucleotide to have a thermodynamic preference for binding to the molecular target. In order to retain preferable molecular target binding, $Mg^{+2}$ or $K^+$ may be added to shift the equilibrium. Addition of up to about 37 mM KCl will shift the equilibrium of a given signaling polynucleotide to favor binding of a molecular target while adding up to about 5 mM $MgCl_2$ will shift the equilibrium towards retention of the double strand structure, thereby lowering the affinity of the signaling polynucleotide for its molecular target.

It is not necessary for the two reverse complementary strands to be on opposite sides in order to create a stem-loop structure. The reverse complementary strand can be attached/annealed to the 5'-end. The sequence must be long enough to physically interfere with the structure. The double strand binding needs to prevent the formation of the secondary structure folding which is needed in order to bind the molecular target.

In certain embodiments, the signaling polynucleotides are dimeric entities with a core sequence linked to a fluorophore and a shorter annealed linker sequence linked to a quencher, or vice versa.

In certain embodiments, the signaling polynucleotide sequences are chemically modified with 2"-O-methyl modifications. Such modifications are expected to not significantly affect the binding affinity and sensitivity with respect to binding of the molecular target, while enhancing stability.

Targets of the Invention: Allergens

The present invention provides detection molecules (themselves monomers or multimers) that bind to an allergen. As stated above, detection molecules may be nucleic acid-based or amino acid-based.

In some embodiments, the target of the detection molecules is the allergen protein or variants thereof. In some embodiments, detection molecules may be designed to bind or associate with proteins or other biomolecules which themselves associated with the allergen.

According to the present invention, and while not wishing to be bound by theory, the detection molecules may completely or partially bind an allergen.

In some embodiments, allergens are food allergens. Examples of allergenic proteins associated with food include, but are not limited to, Brine shrimp (Art fr 5), Crab (Cha f 1), North Sea Shrimp (Cra c 1, Cra c 2, Cra c 4, Cra c 5, Cra c 6, Cra c 8), American lobster (Hom a 1, Hom a 3, Hom a 6), white shrimp (Lit v 1, Lit v 2, Lit v 3, Lit v4), giant freshwater prawn (Mac r 1), shrimp (Met e 1, Pen a 1, Pen i 1), northern shrimp (Pan b 1), spiny lobster (Pan s 1), black tiger shrimp (Pen m 1, Pen m 2, Pen m 3, Pen m 4, Pen m 6), narrow-clawed crayfish (Pon i 4, Pon i 7), blue swimmer crab (Por p 1), domestic cattle (Bos d 4, Bos d 5, Bos d 6, Bos d 7, Bos d 8, Bos d 9, Bos d 10, Bos d 11, Bos d 12), Atlantic herring (Clu h 1), common carp (Cyp c 1), Baltic cod (Gad c 1), Atlantic cod (Gad m 1, Gad m 2, Gad m 3), cod (Gad c 1), chicken (Gal d 1, Gal d 2, Gal d 3, Gal d 4, Gal d 5), Barramunda (Lat c 1), Lepidorhombus whiffiagonis (Lep w 1), chum salmon (Onc k 5), Atlantic salmon (Sal s 1, Sal s 2, Sal s 3) rainbow trout (Onc m 1), Mozambique tilapia (Ore m 4), edible frog (Ran e 1, Ran e 2), pacific pilchard (Sar sa 1), ocean perch (Seb m 1), yellowfin tuna (Thu a 1, Thu a 2, Thu a 3), swordfish (Xip g 1), abalone (Hal m 1), brown garden snail (Hel as 1), Squid (Tod p 1), pineapple (Ana c 1, Ana c 2), asparagus (Aspa o 1), barley (Hor v 12, Hor v 15, Hor v 16, Hor v 17, Hor v 20, Hor v 21), banana (Mus a 1, Mus a 2, Mus a 3, Mus a 4, Mus a 5), banana (Musxpl), rice (Ory s 12), rye (Sec c 20), wheat (Tri a 12, Tri a 14, Tri a 18, Tri a 19, Tri a 25, Tri a 26, Tri a 36, Tri a 37), maize (corn) (Zea m 14, Zea m 25), kiwi fruit (Act c1, Act c 2, Act c 5, Act c 8, Act c 10, Act d 1, Act d 2, Act d 3, Act d 4, Act d 5, Act d 6, Act d 7, Act d 8, Act d 9, Act d 10, Act d 11), cashew (Ana o 1, Ana o 2, Ana o 3), celery (Api g 1, Api g 2, Api g 3, Api g 4, Api g 5, Api g 6), peanut (Ara h 1, Ara h 2, Ara h 3, Ara h 4, Ara h 5, Ara h 6, Ara h 7, Ara h 8, Ara h 9, Ara h 10, Ara h 11, Ara h 12, Ara h 13), brazil nut (Ber e 1, Ber e 2), oriental mustard (Bra j 1), rapeseed (Bra n 1), cabbage (Bra o 3), turnip (Bra r 1, Bra r 2), bell pepper (Cap a 1w, Cap a 2), pecan (Car i 1, Car i 4), chestnut (Cas s 1, Cas s 5, Cas s 8, Cas s 9), lemon (Cit I 3), tangerine (Cit r 3), sweet orange (Cit s 1, Cit s 2, Cit s 3), Hazel (Cor a 1, Cor a 2, Cor a 8, Cor a 9, Cor a 11, Cor a 12, Cor a 13, Cor a 14), muskmelon (Cuc m 1, Cuc m 2, Cuc m 3), carrot (Dau c 1, Dau c 4, Dau c 5), common buckwheat (Fag e 2, Fag e 3), tartarian buckwheat (Fag t 2), strawberry (Fra a 1, Fra a 3, Fra a 4), soybean (Gly m 1, Gly m 2, Gly m 3, Gly m 4, Gly m 5, Gly m 6, Gly m 7, Gly m 8), sunflower (Hel a1, Hel a 2, Hel a 3), black walnut (Jug n 1, Jug n 2), English walnut (Jug r 1, Jug r 2, Jug r 3, Jug r 4), Cultivated lettuce (Lac s 1), Lentil (Len c 1, Len c 2, Len c 3), litchi (Lit c 1), narrow-leaved blue lupin (Lup an 1), apple (Mal d 1, Mal d 2, Mal d 3, Mal d 4), Cassava (Man e 5), mulberry (Mor n 3), avocado (Pers a 1), green bean (Pha v 3), pistachio (Pis v 1, Pis v 2, Pis v 3, Pis v 4, Pis v 5), pea (Pis s 1, Pis s 2), apricot (Pru ar 1, Pru ar 3), sweet cherry (Pru av 1, Pru av 2, Pru av 3, Pru av 4), European plum (Pru d 3), almond (Pru du 3, Pru du 4, Pru du 5, Pru du 6), peach (Pru p 1, Pru p 2, Pru p 3, Pru p 4, Pru p 7), pomegranate (Pun g 1), pear (Pyr c 1, Pyr c 3, Pyr c 4, Pyr c 5), castor bean (Ric c 1), red raspberry (Rub i 1, Rub i 3), Sesame (Ses i 1, Ses i 2, Ses i 3, Ses i 4, Ses i 5, Ses i 6, Ses i 7), yellow mustard (Sin a 1, Sin a 2, Sin a 3, Sin a 4), tomato (Sola I 1, Sola I 2, Sola I 3, Sola I 4), potato (Sola t 1, Sola t 2, Sola t 3, Sola t 4), Mung bean (Vig r 1, Vig r 2, Vig r 3, Vig r 4, Vig r 5, Vig r 6), grape (Vit v 1), Chinese date (Ziz m 1), *Anacardium occidentale* (Ana o 1.0101, Ana o 1.0102), *Apium graveolens* (Api g 1.0101, Api g 1.0201), *Daucus carota* (Dau c1.0101, Dau c1.0102, Dau c1.0103, Dau c1.0104, Dau c1.0105, Dau c1.0201), *Citrus sinensis* (Cit s3.0101, Cit s3.0102), *Glycine max* (Gly m1.0101, Gly m1.0102, Gly m3.0101, Gly m3.0102), *Lens culinaris* (Len c1.0101, Len c1.0102, Len c1.0103), *Pisum sativum* (Pis s1.0101, Pis s1.0102), *Lycopersicon sativum* (Lyc e2.0101, Lyc e2.0102), *Fragaria ananassa* (Fra a3.0101, Fra a3.0102, Fra a3.0201, Fra a3.0202, Fra a3.0203, Fra a3.0204, Fra a3.0301), *Malus domestica* (Mal d1.0101, Mal d1.0102, Mal d1.0103, Mal d1.0104, Mal d1.0105, Mal d1.0106, Mal d1.0107, Mal d1.0108, Mal d1.0109, Mal d1.0201, Mal d1.0202, Mal d1.0203, Mal d1.0204, Mal d1.0205, Mal d1.0206, Mal d1.0207, Mal d1.0208, Mal d1.0301, Mal d1.0302, Mal d1.0303, Mal d1.0304, Mal d1.0401, Mal d1.0402, Mal d1.0403, Mal d3.0101w, Mal d3.0102w, Mal d3.0201w, Mal d3.0202w, Mal d3.0203w, Mal d4.0101, Mal d4.0102, Mal d4.0201, Mal d4.0202, Mal d4.0301, Mal d4.0302), *Prunus avium* (Pru av 1.0101, Pru av 1.0201, Pru av 1.0202, Pru av 1.0203), and *Prunus persica* (Pru p4.0101, Pru p4.0201); and any variants thereof. The names of allergens associated with food are systematically named and listed according to IUIS Allergen Nomenclature Sub-Committee (see, International Union of Immunological Societies Allergen Nomenclature Sub-Committee, List of isoallergens and variants.)

In addition to food allergens, the detection molecules may detect airborne particulates/allergens and other environmental allergens. Samples that contain allergens may be obtained from plants (e.g. weeds, grasses, trees, pollens), animals (e.g., allergens found in the dander, urine, saliva, blood or other bodily fluid of mammals such as cat, dog, cow, pig, sheep, horse, rabbit, rat, guinea pig, mouse and gerbil), fungi/mold, insects (e.g., stinging insects such as bee, wasp, and hornet and *chirnomidae* (non-biting midges), as well as other insects such as the housefly, fruit fly, sheep blow fly, screw worm fly, grain weevil, silkworm, honeybee, non-biting midge larvae, bee moth larvae, mealworm, cockroach and larvae of *Tenibrio molitor* beetle; spiders and mites such as the house dust mite), rubbers (e.g. latex), metals, chemicals (e.g. drugs, protein detergent additives) and autoallergens and human autoallergens (e.g. Hom s 1, Hom s 2, Hom s 3, Hom s 4, Hom s 5) (see, Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants).

Examples of allergenic proteins from plants that can be detected using the detection molecules and devices of the present invention include, but are not limited to, ash (Fra e 1), Japanese cypress (Cha o1, Cha o 2), sugi (Cry j1, Cry j 2), cypress (Cup a 1), common cypress (Cup s 1, Cup s 3), mountain cedar (Jun a 1, Jun a 2, Jun a 3, Jun s 1), prickly juniper (Jun o 1), eastern red cedar (Jun v 1, Jun v 3), sweet vernal grass (Ant o 1), saffron crocus (Cro s 1, Cro s 2), Bermuda grass (Cyn d 1, Cyn d 7, Cyn d 12, Cyn d 15, Cyn d 22w, Cyn d 23, Cyn d 24), orchard grass (Dac g 1, Dac g 2, Dac g 3, Dac g 4, Dac g 5), meadow fescue (Fes p 4), velvet grass (Hol I 1, Hol I 5), barley (Hor v 1, Hor v 5), rye grass (Lol p 1, Lol p 2, Lol p 3, Lol p 4, Lol p 11), bahia grass (Pas n 1), canary grass (Pha a 1, Pha a 5), timothy (Phl p 1, Phl p 2, Phl p 4, Phl p 5, Phl p 6, Phl p 7, Phl p 11, Phl p 12, Phl p 13), date palm (Pho d 2), Kentucky blue grass (Poa p 1, Poa p 5), rye (Sec c 1, Sec c 5, Sec c 38), Johnson grass (Sor h 1), wheat (Tri a 15, Tri a 21, Tri a 27, Tri a 28, Tri a 29, Tri a 30, Tri a 31, Tri a 32, Tri a 33, Tri a 34, Tri a 35, Tri a 39), maize (Zea m 1, Zea m 12), alder (Aln g 1, Aln g 4), redroot pigweed (Ama r 2), short ragweed (Amb a 1, Amb a 2, Amb a 3, Amb a 4, Amb a 5, Amb a 6, Amb a 7, Amb a 8, Amb a 9, Amb a 10, Amb a 11), western ragweed (Amb p 5), giant ragweed (Amb t 5), mugwort (Art v 1, Art v 2, Art v 3, Art v 4, Art v 5, Art v 6), sugar beet (Beta v 1, beta v 2), European white birch (Bet v 1, Bet v 2, Bet v 3, Bet v 4, Bet v 6, Bet v 7), turnip (Bra r 5), hornbeam (Car b 1), chestnut (Cas s 1), rosy periwinkle (Cat r 1), lamb's-quarters, pigweed (Che a 1, Che a 2, Che a 3), Arabian coffee (Cof a 1, Cof a 2, Cof a 3), Hazel (Cor a 6, Cor a 10), Hazel nut (Cor a1.04, Cor a2, Cor a8), European beech (Fag s 1), ash (Fra e 1), sunflower (Hel a 1, Hel a 2), para rubber tree (Hey b 1, Hey b 2, Hey b 3, Hey b 4, Hey b 5, Hey b 6, Hey b 7, Hey b 8, Hey b 9, Hey b 10, Hey b 11, Hey b 12, Hey b 13, Hey b 14), Japanese hop (Hum j 1), privet (Lig v 1), *Mercurialis annua* (Mer a 1), olive (Ole e 1, Ole e 2, Ole e 3, Ole e 4, Ole e 5, Ole e 6, Ole e 7, Ole e 8, Ole e 9, Ole e 10, Ole e 11), *European hophornbeam* (Ost c 1), *Parietaria judaica* (Par j 1, Par j 2, Par j 3, Par j 4), *Parietaria officinalis* (Par o 1), *Plantago lanceolata* (Pal I 1), London plane tree (Pla a 1, Pla a 2, Pla a 3), *Platanus orientalis* (Pla or 1, Pla or 2, Pla or 3), white oak (Que a 1), Russian thistle (Sal k 1, Sal k 2, Sal k 3, Sal k 4, Sal k 5), tomato (Sola I 5), Lilac (Syr v 1, Syr v 5), Russian-thistle (Sal k 1), English plantain (Pla 11), *Ambrosia artemisiifolia* (Amb a8.0101, Amb a8.0102, Amb a9.0101, Amb a9.0102), *Plantago lanceolata* (Pla 11.0101, Pla 11.0102, Pla 11.0103), *Parietaria judaica* (Par j 3.0102), *Cynodon dactylon* (Cyn d1.0101, Cyn d1.0102, Cyn d1.0103, Cyn d1.0104, Cyn d1.0105, Cyn d1.0106, Cyn d1.0107, Cyn d1.0201, Cyn d1.0202, Cyn d1.0203, Cyn d1.0204), *Holcus lanatus* (Hol 11.0101, Hol 11.0102), *Lolium perenne* (Phl p1.0101, Phl p1.0102, Phl p4.0101, Phl p4.0201, Phl p5.0101, Phl p5.0102, Phl p5.0103, Phl p5.0104, Phl p5.0105, Phl p5.0106, Phl p5.0107, Phl p5.0108, Phl p5.0201, Phl p5.0202), *Secale cereale* (Sec c20.0101, Sec c20.0201), *Betula Verrucosa* (Bet v1.0101, Bet v1.0102, Bet v 1.0103, Bet v 1.0201, Bet v 1.0301, Bet v1.0401, Bet v 1.0402, Bet v 1.0501, Bet v 1.0601, Bet v 1.0602, Bet v1.0701, Bet v1.0801, Bet v1.0901, Bet v1.1001, Bet v1.1101, Bet v1.1201, Bet v 1.1301, Bet v1.1401, Bet v1.1402, Bet v1.1501, Bet v1.1502, Bet v1.1601, Bet v1.1701, Bet v 1.1801, Bet v1.1901, Bet v1.2001, Bet v1.2101, Bet v1.2201, Bet v1.2301, Bet v1.2401, Bet v 1.2501, Bet v1.2601, Bet v1.2701, Bet v1.2801, Bet v1.2901, Bet v1.3001, Bet v1.3101, Bet v 6.0101, Bet v6.0102), *Carpinus betulus* (Car b1.0101, Car b1.0102, Car b1.0103, Car b1.0104, Car b1.0105, Car b1.0106, Car b1.0106, Car b1.0106, Car b1.0106, Car b1.0107, Car b1.0107, Car b1.0108, Car b1.0201, Car b1.0301, Car b1.0302), *Corylus avellana* (Cor a1.0101, Cor a1.0102, Cor a1.0103, Cor a1.0104, Cor a1.0201, Cor a1.0301, Cor a1.0401, Cor a1.0402, Cor a1.0403, Cor a1.0404), *Ligustrum vulgare* (Syr v1.0101, Syr v1.0102, Syr v1.0103), *Cryptomeria japonica* (Cry j2.0101, Cry j2.0102), and *Cupressus sempervirens* (Cup s1.0101, Cup s1.0102, Cup s1.0103, Cup s1.0104, Cup s1.0105); and any variants thereof.

Lupin is an herbaceous plant of the leguminous family belonging to the genus *Lupinus*. In Europe, lupin flour and seeds are widely used in bread, cookies, pastry, pasta, sauces, as well as in beverages as a substitute for milk or soy, and in gluten-free foods. The International Union of Immunological Societies (IDIS) allergen nomenclature subcommittee recently designated β-conglutin as the Lup an 1 allergen. (Nadal, et al., (2012) *DNA Aptamers against the Lup an 1 Food Allergen.* PLoS ONE 7(4): e35253), and more recently, a high-affinity 11-mer DNA aptamer against Lup an 1 (β-conglutin) was reported (Nadal, et al., (2013) *Probing high-affinity 11-mer DNA aptamer against Lup an 1 (β-conglutin).* Anal. Bioanal. Chem. 405:9343-9349).

Examples of allergenic proteins from mites that can be detected using the detection molecules and devices of the present invention include, but are not limited to, mite (Blo t 1, Blo t 3, Blo t 4, Blo t 5, Blo t 6, Blo t 10, Blo t 11, Blo t 12, Blo t 13, Blo t 19, Blot t 21); American house dust mite (Der f 1, Der f 2, Der f 3, Der f 7, Der f 10, Der f 11, Der f 13, Der f 14, Der f 15, Der f 16, Der f 17, Der f 18, Der f 22, Der f 24); *Dermatophagoides microceras* (house dust mite) (Der m 1); European house dust mite (Der p 1, Der p 2, Der p 3, Der p 4, Der p 5, Der p 6, Der p 7, Der p 8, Der p 9, Der p 10, Der p 11, Der p 14, Der p 15, Der p 20, Der p 21, Der p 23); *Euroglyphus maynei* (House dust mite) (Eur m 2, Eur m 2, Eur m 3, Eur m 4, Eur m 14); storage mite (Aca s 13, Gly d 2, Lep d 2, Lep d 5, Lep d 7, Lep d 10, Lep d 13, Tyr p 2, Tyr p 3, Tyr p 10, Tyr p 13, Tyr p 24), *Dermatophagoides farinae* (Der f1.0101, Der f1.0102, Der f1.0103, Der f1.0104, Der f1.0105, Der f2.0101, Der f2.0102, Der f2.0103, Der f2.0104, Der f2.0105, Der f2.0106, Der f2.0107, Der f2.0108, Der f2.0109, Der f2.0110, Der f2.0111, Der f2.0112, Der f2.0113, Der f2.0114, Der f2.0115, Der f2.0116, Der f2.0117), *Dermatophagoides pteronyssinus* (Der p1.0101, Der p1.0102, Der p1.0103, Der p1.0104, Der p1.0105, Der p1.0106, Der p1.0107, Der p1.0108, Der p1.0109, Der p1.0110, Der p1.0111, Der p1.0112, Der p1.0113, Der p1.0114, Der p1.0115, Der p1.0116, Der p1.0117, Der p1.0118, Der p1.0119, Der p1.0120, Der p1.0121, Der p1.0122, Der p1.0123, Der p2.0101, Der p2.0102, Der p2.0103, Der p2.0104, Der p2.0105, Der p2.0106, Der p2.0107, Der p2.0108, Der p2.0109, Der p2.0110, Der p2.0111, Der p2.0112, Der p2.0113), *Euroglyphus maynei* (Eur m2.0101, Eur m2.0102), *Lepidoglyphus destructor* (Lep d2.0101, Lep d2.0101, Lep d2.0101, Lep d2.0102, Lep d2.0201, Lep d2.020) and *Glycyphagus domesticus* (Gly d2.0101, Gly d2.0201); and any variants thereof.

Examples of allergenic proteins from animals that can be detected using the detection molecules and devices of the present invention include, but are not limited to, domestic cattle (Bos d 2, Bos d 3, Bos d 4, Bos d 5, Bos d 6, Bos d 7, Bos d 8), dog (Can f 1, Can f 2, Can f 3, Can f 4, Can f 5, Can f 6), domestic horse (Equ c 1, Equ c 2, Equ c 3, Equ c 4, Equ c 5), cat (Fel d 1, Fel d 2, Fel d 3, Fel d 4, Fel d 5w, Fel d 6w, Fel d 7, Fel d 8), mouse (Mus m 1), guinea pig (Cav p 1, Cav p 2, Cav p 3, Cav p 4, Cav p 6), rabbit (Ory c 1, Ory c 3, Ory c 4) rat (Rat n 1), *Bos domesticus* (Bos d 2.0101, Bos d 2.0102, Bos d 2.0103) and *Equus caballus* (Equ c2.0101, Equ c 2.0102); and any variants thereof Examples of allergenic proteins from insects that can be detected using the detection molecules and devices of the present invention include, but are not limited to, yellow fever mosquito (Aed a 1, Aed a 2, Aed a 3), Eastern hive bee (Api c 1), giant honeybee (Api d 1), honey bee (Api m 1, Api m 2, Api m 3, Api m 4, Api m 5, Api m 6, Api m 7, Api m 8, Api m 9, Api m 10, Api m 11, Api m 12), pigeon tick (Arg r 1), German cockroach (Bla g 1, Bla g 2, Bla g 3, Bla g 4, Bla g 5, Bla g 6, Bla g 7, Bla g 8, Bla g 11), bumble bee (Bom p 1, Bom p 4, Bom t 1, Bom t 4), silk moth (Bomb m 1), midge (Chi k 10, Chi t 1, Chi t 1.01, Chi t 2, Chi t 2. 0101, Chi t 2. 0102, Chi t 3, Chi t 4, Chi t 5, Chi t 6, Chi t 6. 01, Chi t 7, Chi t 8, Chi t 9), cat flea (Cte f 1, Cte f 2, Cte f 3), yellow hornet (Dol a 5), white face hornet (Dol m 1, Dol m 2, Dol m 5), biting midge (For t 1, For t 2), Savannah Tsetse fly (Glo m 5), Asian ladybeetle (Har a 1, Har a 2), silverfish (Lep s 1), booklouse (Lip b 1), Australian jumper ant (Myr p 1, Myr p 2, Myr p 3), American cockroach (Per a 1, Per a 3, Per a 6, Per a 7, Per a 9, Per a 10), Indian meal moth (Plo i 1, Plo i 2), wasp (Pol a 1, Pol a 2, Pol a 5, Pol e 1, Pol e 4, Pol e 5, Pol f 5, Pol g 1, Pol g 5, Pol m 5, Poly p 1, Poly s 5, Ves vi 5), Mediterranean paper wasp (Pol d 1, Pol d 4, Pol d 5), tropical fire ant (Sol g 2, Sol g 3, Sol g 4), *Solenopsis invicta* (red imported fire ant) (Sol I 1, Sol I 2, Sol I 3, Sol I 4), black fire ant (Sol r 2, Sol r 3), Brazilian fire ant (Sol s 2, Sol s 3), horsefly (Tab y 1, Tab y 2, Tab y 5), pine processionary moth (Tha p 1, Tha p 2), California kissing bug (Tria p 1), European hornet (Vesp c 1, Vesp c 5), *Vespa magnifica* (hornet) (Vesp ma 2, Vesp ma 5), *Vespa mandarinia* (Giant asian hornet) (Vesp ml, Vesp m 5), yellow jacket (Ves f 5, Ves g 5, Ves m 1, Ves m 2, Ves m 5), *Vespula germanica* (yellow jacket) (Ves p 5), *Vespula squamosa* (Yellow jacket) (Ves s 1, Ve s s5), *Vespula vulgaris* (Yellow jacket) (Ves v 1, Ves v 2, Ves v 3, Ves v 4, Ves v 5, Ves v 6), *Blattella germanica* (Bla g 1.0101, Bla g 1.0102, Bla g 1.0103, Bla g 1.02, Bla g 6.0101, Bla g 6.0201, Bla g 6.0301), *Periplaneta Americana* (Per a1.0101, Per a1.0102, Per a1.0103, Per a1.0104, Per a1.02, Per a3.01, Per a3.0201, Per a3.0202, Per a3.0203, Per a7.0101, Per a7.0102), *Vespa crabo* (Ves pc 5.0101, Ves pc 5.0101), *Vespa mandarina* (Vesp m 1.01, Vesp m 1.02); and any variants thereof.

Examples of allergenic proteins from fungi/mold that can be detected using the detection molecules and devices of the present invention include, but are not limited to, *Alternaria alternata* (*Alternaria* rot fungus) (Alt a 1, Alt a 3, Alt a 4, Alt a 5, Alt a 6, Alt a 7, Alt a 8, Alt a 10, Alt a 12, Alt a 13), *Aspergillus flavus* (fungus) (Asp fl 13), *Aspergillus fumigatus* (fungus) (Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22, Asp f 23, Asp f 27, Asp f 28, Asp f 29, Asp f 34), *Aspergillus niger* (Asp n 14, Asp n 18, Asp n 25), *Aspergillus oryzae* (Asp o 13, Asp o 21), *Aspergillus versicolor* (Asp v 13), *Candida albicans* (Yeast) (Cand a 1, Cand a 3), *Candida boidinii* (Yeast) (Cand b 2), *Cladosporium cladosporioides* (Cla c 9, Cla c 14), *Cladosporium herbarum* (Cla h 2, Cla h 5, Cla h 6, Cla h 7, Cla h 8, Cla h 9, Cla h 10, Cla h 12), *Curvularia lunata* (Synonym: *Cochliobolus lunatus*) (Cur I 1, Cur I 2, Cur I 3, Cur I 4), *Epicoccum purpurascens* (Soil fungus) (Epi p 1), *Fusarium culmorum* (N.A.) (Fus c 1, Fus c 2), *Fusarium proliferatum* (Fus p 4), *Penicillium brevicompactum* (Pen b 13, Pen b 26), *Penicillium chrysogenum* (Pen ch 13, Pen ch 18, Pen ch 20, Pen ch 31, Pen ch 33, Pen ch 35), *Penicillium citrinum* (Pen c 3, Pen c 13, Pen c 19, Pen c 22, Pen c 24, Pen c 30, Pen c 32), *Penicillium crustosum* (Pen cr 26), *Penicillium oxalicum* (Pen o 18), *Stachybotrys chartarum* (Sta c 3), *Trichophyton rubrum* (Tri r 2, Tri r 4), *Trichophyton tonsurans* (Tri t 1, Tri t 4), *Psilocybe cubensis* (Psi c 1, Psi c 2), Shaggy cap (Cop c 1, Cop c 2, Cop c 3, Cop c 5, Cop c 7), *Rhodotorula mucilaginosa* (Rho m 1, Rho m 2), *Malassezia furfur* (Malaf2, Malaf3, Malaf4), *Malassezia sympodialis* (Malasl, Malas5, Malas6, Malas7, Malas8, Malas9, Malas10, Malas11, Malas12, Malas13) and *Alternaria* alternate (Alt a1.0101, Alt a1.0102); and any variants thereof.

Examples of additional allergens include, but are not limited to, Nematode (Ani s 1, Ani s 2, Ani s 3, Ani s 4), worm (Asc s 1), soft coral (Den n 1), rubber (Latex) (Hey b 1, Hey b 2, Hey b 3, Hey b 5, Hey b 6, Hey b 7, Hey b 8, Hey b 9, Hey b 10, Hey b 11, Hey b 12, Hey b 13), obeche (Trip s 1) and Heveabrasiliensis (Hey b6.01, Hey b6.0201, Hey b6.0202, Hey b6.03, Hey b8.0101, Hey b8.0102, Hey b8.0201, Hey b8.0202, Hey b8.0203, Hey b8.0204, Hey b10.0101, Hey b10.0102, Hey b10.0103, Hey b11.0101, Hey b11.0102); and any variants thereof.

In some embodiments, the present methods and devices may be used in a hospital for clinical food allergy or allergy test and to identify food/allergen(s) to which a patient is allergic. In addition, the portable device of the present invention may be used as a carry-on tester for people who have food/environmental allergy, for example at home to test commercial food, or at restaurant to check dishes they ordered. The food sample could be fresh food, frozen food, cooled food or processed food containing animal derived meat and/or vegetables.

Targets of the Invention: Pathogens

In some embodiments, the present invention provides detection molecules that bind to pathogenic microorganisms in a sample. The detection molecules as discussed above are nucleic acid molecules (preferably aptamers) that are designed to bind one or more target proteins specific to a pathogenic microorganism. The target protein may be a molecule secreted by a pathogen, a surface protein, a protein induced in a host which a pathogen attacks, or a portion of a target protein. The present invention allows for the detection and identification of many different types of pathogenic microorganisms, such as bacteria, yeasts, fungi, spores, viruses or prions.

As used herein, the term "pathogen" means any disease-producing agent (especially a virus or bacterium or other microorganism).

In some aspects, the present methods and devices provide extremely rapid detection and identification, with great specificity and sensitivity, of pathogenic microorganisms in a sample. The invention may be used for healthcase, public safety, military purpose or governmental use.

In accordance with the present invention, a pathogenic microorganism is a pathogenic bacterium. In certain embodiments, a pathogenic bacterium is a human pathogenic bacterium, such as, for example, *Bacillus anthracis, Bordetella pertussis, Borrelia burgdorferi, Brucella abortus, Brucella canis, Brucella melitensis, Brucella suis, Campylobacter jejuni, Chlamydia trachomatis, Chlamydophila, Clostridium botulinum, Clostridium difficile, Clostridium perfringens, Clostridium tetani, Corynebacterium diphtheria, Enterococcus faecalis, Enterococcus faecium, Escherichia coli, Enterotoxigenic Escherichia coli, Enteropathogenic E. Coli, E. coli* O 175: H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycolasma pneumonia, Neissaria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus,*

In some aspects, a pathogen may be a pathogenic virus such as, for example, a member of the Papilloma viruses, Parvoviruses, Adenoviruses, Herpesviruses, Vaccine virus, Arenaviruses, Coronaviruses, Rhinoviruses, Respiratory syncytial viruses, Influenza viruses, Picornaviruses, Paramyxoviruses, Reoviruses, Retroviruses, Rhabdoviruses, or human immunodeficiency virus (HIV), Polyomaviruses, Poxviruses, Hepadnaviruses, Astroviruses, Caliciviruses, Flaviviruses, Togaviruses, Hepeviviruses, Orthomyxoviruses, Bunyaviruses, or Filoviruses, Pathogens may be a fungus that is the causative agent of conditions such as, for example, Ringworm, Histoplasmosis, Blastomycosis, Aspergillosis, Cryptococcosis, Sporotrichosis, Coccidiodomycosis, Paracoccidioidomycosis, Mucomycosis, Candidiasis, Dermatophytosis, Protothecosis, Pityriasis, Mycetoma, Paracoccidiodomycosis, Phaeohphomycosis, Pseudallescheriasis, Trichosporosis, or Pneumocystis.

In some embodiments, pathogens may be plant pathogens that cause plant diseases. Pathogens that cause plant diseases include fungi, bacteria, protists, viruses, oomycetes, virus-like organisms, viroids, phytoplasmas, protozoa and nematodes. The majority of fungi that cause plant diseases include the Ascomycetes and the Basidiomycetes. Significant bacterial plant pathogens include *Burkholderia, Proteobacteria, Pseudomonas syringae* pv and phytoplasmas. As non-limiting examples, plant pathogens include *Xanthomonas axonopodis* (that causes Citrus Canker), *P. pachyrhizi* (that causes Soybean Rust), uncultured bacterium (that causes Lethal Yellowing), Tenuivirus (that causes Maize Stripe), *Phytophthora ramorum* (a water mold) (that causes Sudden Oak Death), *Candidatus Liberibacter asiaticus* (that causes Citrus Greening) and *Xtllella fastidiosa* (that causes Pierce's Diseases).

In some embodiments, pathogens may be animal pathogens capable of infecting animals. Animal Pathogens include, but are limited to, *Chlamydophila abortus, Bacillus anthracis, Ascaris suum, Aspergillus fumigatus, Aspergillus terreus,* other *Aspergillus* species, *asteurella multocida, Bordetella bronchiseptica, Babesia caballi, Babesia trautmanni, Babesia motasi, asteurella multocida, Blastomyces dermatitidis, Neospora caninum, Eimeria* species, *Ehrlichia*

*ruminantium*, Bovine Viral Diarrhea Virus (BVDV or BVD); Bluetongue Virus (BM; Foot-and-Mouth Disease Virus (FMDV); Malignant Catarrhal Fever WM; ovine herpesvirus-2 (OvHV-2); alcelaphine herpesvirus-1 (AHV1); Porcine Respiratory Reproductive Syndrome Virus (PRRSV or PRRS); Rinderpest Virus (RPV); Swine Vesicular Disease Virus (SVDV or Ski)); Vesicular Exanthema of Swine Virus (VEST); Vesicular Stomatitis Virus (VSV); Bovine Herpesvirus-1 (BHV-1 or BHV); Parapox (PPDX or PPox); and Bovine Papular Stomatitis Virus (BPSV).

In some embodiments, the detection molecules have specificity for a particular genera, species or strain of pathogenic microorganisms.

In some embodiments, the present invention may be used to detect and identify a pathogen in a sample. In some embodiments, the sample is a food sample, a beverage sample, a water sample, a soil sample, a plant sample, an agriculture sample, an animal sample, a biological sample, a surgical biopsy, a pharmaceutical sample or a personal care sample.

In some embodiments, the present invention may be used in food industry for detecting food contamination and food safety control. In accordance with the present invention, the detection molecules may detect and identify microorganisms (e.g. spoilage microorganism and pathogenic microorganisms) in a food sample.

In some embodiments, the food sample may be a food or a food product. The sample may be a raw ingredient, a finished food product or may be taken from the environment of manufacture or storage. As non-limiting examples, a food sample may be a raw meat or a meat product; a diary product (e.g. cheese yogurt); vegetables or a vegetable based product (e.g. salad); infant formula; or can food.

In some embodiments, the sample may be a beverage sample, such as beer or a sample taken during the brewing of beer. In other words the present invention may be used to detect the presence of microorganisms such as beer spoilage bacteria. In some aspect, the beverage includes drinking water. Accordingly, the present invention may be used to detect a pathogenic contamination in drinking water.

In some embodiments, the presence of pathogenic microorganisms may be detected in an animal sample. An animal sample may be from any organism, with mammalian samples, including human, livestock, (e.g. sheep, cow, horse, pig, goat, lama, emu, ostrich or donkey), poultry (e.g. chicken, turkey, goose, duck, or game bird), fish (e.g. salmon or sturgeon), laboratory animal (e.g. rabbit, guinea pig, rat or mouse), companion animal (e.g. dog or cat) or a wild animal.

In one embodiment, the sample may be a personal care product such as an eye care product, for example contact lens solution or antihistamine eyedrops.

In some embodiments, the sample may be a pharmaceutical preparation (e.g. a drug).

In some embodiments, the presence of pathogenic microorganisms may be detected in a plant sample. In accordance with the present invention, the plant sample may be leaves, roots, flowers, seeds, fruits, stems or any parts of a plant. Plant samples refer to any plant including but not limited to field crops or greenhouse-grown plants. The invention also encompasses plant samples obtained from wild plants (i.e. plants which are not grown by men).

In some embodiments, the presence of pathogenic microorganisms may be detected in an environmental sample, including, but not limited to, an air samples, an agricultural sample (including plant sample and crop sample), a water sample and a soil sample. Water sample may be obtained for example but not limited to from drinking water, reservoir sewage, sea water, lakes, groundwater, rivers and other water sources. The methods disclosed in the present invention may be applied for home use, municipal use, or governmental use.

In some embodiments, the detection molecules according to the present invention may be used in a manufacturing plant to detect for the presence of pathogenic microorganisms on or in equipment used therein.

In some embodiments, the present invention may be used as a tool in a research laboratory. For example, the detection molecules may detect pathogenic contamination in in vitro cell culture.

It is envisaged that the present invention may be find use in public health applications. For example, the detection molecules may be used to detect the presence of pathogenic microorganisms in national/worldwide infectious diseases.

It is also envisaged that the present invention provides a lightweight, low cost and man-portable device to detect, collect, and identify biological pathogens and toxins on the battlefield. In one embodiment, the devices and methods of the present invention may detect the presence of biological agents and identify target species.

Targets of the Invention: Disease Proteins

In addition to allergens and pathogenic proteins, the present invention provides detection molecules that bind to other target molecules such as diseases associated proteins to diagnose, stage diseases and disorders. Disease associated proteins may be secreted polypeptides and peptides (e.g. circulating molecules); cell surface proteins (e.g. receptors); biomarkers that are expressed or overexpressed in a particular disease condition; isoforms, derivatives and/or variants of a particular protein that are only present in a disease condition; mutated proteins that cause a disorder; and proteins derived from another organism which causes a clinical condition in the host such as viral infection. The detection molecules may be nucleic acid molecules (preferably aptamers) that are designed to specifically bind to an epitope on a target protein or a segment of an oligopeptide of the protein to be tested. The nucleic acid based detection molecules bind diagnostic proteins or portion thereof, providing fast and low cost assays and devices in the field of in vitro diagnosis and especially in the field of Point of Care (POC) diagnostics, for example, on the battlefields and refugee camp sites.

As non-limiting examples, secreted circulating proteins in accordance with the present invention include biomarkers that are indicative to proliferating tumor cells, inflammatory associated markers, hormones, cytokines, metabolites, and soluble molecules derived from a virus, a bacteria or a fungus infection. For example, cytokine-sensing microwells have been developed; fluorescence resonance energy transfer (FRET)-based aptamer beacons were used to detect IFN-γ (Tuleuova, et al., *Micropatterning of Aptamer Beacons to Create Cytokine-Sensing Surfaces*. Cellular and Molecular Bioengineering, 2010, 3(4):337-344).

Also as non-limiting examples, a cell surface protein in accordance with the invention are a receptor, a cell surface marker, a microbe antigen, or a receptor ligand.

In some embodiments, target proteins for diagnostics are obtained from biological samples from subjects (including human and animals). A biological sample may be a bodily fluid, a tissue, a tissue biopsy (e.g. surgical biopsy), a skin swab, an isolated cell population or a cell preparation. The bodily fluid samples may be at least one selected from blood, serum, plasma, spinal fluid, cerebrospinal fluid, joint fluid, amniotic fluid, tear fluid, broncheoalveolar fluid, sputum, vaginal fluid, semen, throat wash, nasal wash, saliva, urine and lysates from tissues, organs and cells or other source. In some aspects, the cells in the population of cells and cell preparation comprise primary cells and an in vitro cultured cell collection. In other aspects, the population cells contain diseased cells (e.g. cancer cells). In certain embodiments, the cells in the population of cells and cell preparation is selected from animal cells, plant cells, viral cells, bacteria cells and fungus cells.

According to the present invention, the detection methods and devices may be used for determining the presence, absence or amount of a target molecule, wherein said target molecule is a target molecule associated with a clinical condition and wherein the amount of said detectable moiety is indicative of the presence of the clinical condition in the subject. As non-limiting examples, the method of the invention may be employed in the detection of a viral infection, for example Hepatitis B virus (HBV), hepatitis C virus (HCV), Cytomegalovirus (CMV), Human immunodeficiency virus (HIV), Epstein-Barr virus (EBV), HERPES virus, Polio virus and influenza virus (both Human and Avian). It may also be employed in the detection of a bacterial infection, such as *Listeria, Staphylococcus Aureus, Methicillin* resistance *Staphylococcus Aureus* (MRSA), *Corynebacterium Diphtheriae* (causing Diphtheria), *E. coli*, Group B *streptococcus* (GBS), Group A *streptococcus, Mycobacterium Tuberculosis* (causing Tuberculosis (TB), *Salmonella, Vibrio Cholerae, Campylobacter, Brucellosis, Neisseria Meningitidis* (causing meningococcus), *Streptococcus pneumonia* and *Candida*.

The compositions and methods described herein are useful in treating or preventing an undesirable or deleterious immune response associated with defective NF-[kappa]B activation including, for example, allergies, organ-specific diseases, parasitic diseases, and inflammatory and autoimmune diseases. Examples of allergies include seasonal respiratory allergies, allergy to aeroallergens such as hay fever, allergy treatable by reducing serum IgE and eosinophilia, asthma, eczema, animal allergies, food allergies, chronic urticaria, latex allergies, allergic rhinitis, atopic dermatitis, or allergies treatable by allergic desensitization. Other clinical conditions that can be diagnosed using the detection molecules of the present invention include, but are not limited to, cancer (e.g. solid tumor, carcinoma, sarcoma, lymphoma, leukemia, germ cell tumor, blastoma or metastasis), inflammatory diseases (Crohn's disease, chronic inflammatory eye diseases, chronic inflammatory lung diseases and chronic inflammatory liver diseases, autoimmune hemolytic anemia, idiopathic leucopoenia, ulcerative colitis, dermatomyositis, scleroderma, mixed connective tissue disease, irritable bowel syndrome, systemic lupus erythromatosus (SLE), multiple sclerosis, myasthenia gravis, Guillan-Barre syndrome (antiphospholipid syndrome), primary myxoedema, thyrotoxicosis, pernicious anemia, autoimmune atrophic gastris, alopecia totalis, Addison's disease, insulin-dependent diabetes mellitus (IDDM), Goodpasture's syndrome, Behcet's syndrome, Sjogren's syndrome, rheumatoid arthritis, sympathetic ophthalmia, Hashimoto's disease/hypothyroiditis, celiac disease/dermatitis herpetiformis, adult-onset idiopathic hypoparathyroidism (AOIH), amyotrophic lateral sclerosis, and demyelinating disease primary biliary cirrhosis, mixed connective tissue disease, chronic active hepatitis, polyendocrine failure, vitiligo, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Graves' disease/hyperthyroiditis, scleroderma, chronic idiopathic thrombocytopenic purpura, peripheral neuropathy, diabetic neuropathy, hemochromatosis, Henoch-Schonlein purpura, idiopathic IgA nephropathy, insulin-dependent diabetes mellitus (IDDM), Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, and septic shock), genetic disorders, autoimmune diseases (e.g. Multiple sclerosis, Arthritis Autoimmune hepatitis, Crohn's disease, Diabetes mellitus, type 1, Inflammatory bowel disease, Multiple sclerosis, Psoriasis, systemic lupus erythematosus (SLE), myasthenia gravis, stiff-man syndrome, thyroiditis, Sydenham chorea, Rheumatoid arthritis, ankylosing spondylitis, autoimmune aplastic anemia, autoimmune hemolytic anemia, Churg Strauss disease, scleroderma, Wegener's granulomatosis, and Wiskott Aldrich syndrome), metabolic disorders, brain diseases and heart disorders. Other unwanted immune reactions that can also be treated or prevented by the present invention include antibodies to recombinant therapeutic agents such as anti-factor VIII antibodies in hemophilia or anti-insulin antibodies in diabetes.

Short, single-stranded DNA anti-thrombin aptamers are known and have been characterized (Hamaguchi, et al., *Aptamer Beacons for the Direct Detection of Proteins*. Analytical Biochemistry 2001, 294:126-131; Wang, et al., *Ultrasensitive colorimetric detection of protein by aptamer-Au nanoparticles conjugates based on a dot-blot assay*. Chem. Commun., 2008, 2520-2522). The nucleotide sequence of one such anti-thrombin aptamer is 5' GGTTG-GTGTGGTTGG 3' (SEQ ID NO: 10). A strong inverse correlation between the thermodynamics of hybridization and the speed of activation has been demonstrated, and by pre-organizing the thrombin-binding quadruplex within the aptamer, the speed of response was greatly increased. Thus, aptamer beacons could be designed to be activated by threefold within 1 min of the addition of thrombin. (Hall, et al., *Kinetic Optimization of a Protein-Responsive Aptamer Beacon*. Biotechnology and Bioengineering, 2009, 103(6): 1049-1059; incorporated herein by reference in its entirety).

In some aspects, the methods for the detection of a target protein in a biological sample may be used as companion diagnostics. The presence and/or absence of a biomarker associated with a particular disease in a patient will provide valuable information for a specific treatment. Physician could predict an outcome of a treatment for a patient and tailor a most effective regimen for the patient.

In other embodiments, the present invention may be used for monitoring the disease stage and progression of a subject and efficacy of a therapeutic regiment, i.e. monitor the response of the subject to treatment.

Accordingly, the present invention may be used in military settings such as on the battlefield, as well as civilian settings. The portable device and disposable cartridge make it easy to use and the quick detection of the present invention facilitates the large demand of in-field diagnosis of diseases such as wound infection and infectious diseases.

Targets of the Invention: Other Molecules

In some embodiments, the present invention provides detection molecules that bind to non-protein target molecules, for example, a ganglioside, a lipid, a phospholipid, a carbohydrate, a small molecule (e.g. a mycotoxin and an antibiotic), a hapten, and a nucleic acid (DNA or RNA).

In some aspects, the detection molecules of the present invention may be small molecule-binding aptamers. In some aspects, the small molecule-binding aptamers may be applied to detect the presence of pesticides and fertilizers remained in the environment. The small molecule-binding aptamers may recognize pesticides, fertilizers and other chloroaromatic pollutants. Such detection will help the removal of the residues of pesticides and fertilizers after usage.

Examples of pesticides include, but are not limited to, organophosphorus pesticides (e.g. phorate, profenofos, isocarbophos and omethoate); carbamate pesticides; organochlorine insecticides (e.g. DDT and chlordane); pyrethroid pesticides; and sulfonylurea herbicides (e.g. nicosulfuron, triflusulfuron methyl).

In other aspects, the small molecule-binding aptamers may be used to detect the presence of toxins in a sample, for example, the small molecule mycotoxin that contaminates a wide variety of food commodities such as cereal and wine. Application of the small molecule-binding detection molecules (preferably aptamers) may be used in other areas, such as metabolomics and drug discovery.

In other aspects, the small molecule-binding aptamers may be used to detect non-food toxins such urushiol, found in poison ivy, eastern poison oak, western poison oak, or poison sumac; such toxins cause urushiol-induced contact dermatitis. Urushiol, which is not itself a protein, acts as a hapten and chemically reacts with, binds to, and changes the shape of integral membrane proteins on exposed skin cells. Because the affected cells are not recognized as normal parts of the body, a T-cell-mediated immune response is aroused.

Universal Target Extraction Buffer

In some embodiments, a universal protein extraction buffer may be used to retrieve enough target proteins (e.g. allergens) (minimum 2 mg/ml total protein) for analysis from any food matrix. In some embodiments, the formulation of the universal protein extraction buffer can extract the protein at room temperature and in minimal time (less than 1 min). The buffer may need to be incorporated with an extraction protocol that will include food sampling, homogenization and filtration. The extraction protocol may be implemented in a way that is efficient and repeatable over time and in different food matrices. This universal formulation will be clinically relevant as to try to minimally effect the food tested and only sample approximately 0.5 g of food, allowing to detect traces of allergens their concentration will be minimal in the sample. This optimized protein extraction process will provide a fast, accurate and universal protocol that allows detection of an allergen in any food matrix.

Kits and Packaging

Kits.

The detection molecules, compounds and compositions of the present invention may be combined with other ingredients or reagents or prepared as components of kits or other retail products for commercial sale or distribution.

The kit will contain the compound or composition, along with instructions regarding administration and/or use of the kit. The kit may also contain one or more of the following: a syringe, a bag or bottle.

Packaging.

Formulations and/or compositions of detection molecules of the present invention can be packaged for use in a variety of pharmaceutically or diagnostically acceptable containers using any acceptable container closure, as the formulations are compatible with PVC-containing and PVC-free containers and container closures. Examples of acceptable containers include, but are not limited to, ampules and pre-filled syringes, cartridges and the like.

Alternatively, the formulation may contain lyophilized aptamer in one compartment of an admix bag and an acceptable solvent in a separate compartment of the admix bag such that the two compartments may be mixed together prior to administration to a patient. Acceptable containers are well known in the art and commercially available. Preferably, the formulations are stored in a Type 1 glass vial with a butyl rubber stopper. The formulations in liquid form may be stored in a refrigerated environment. Alternatively, the lyophililized formulations may be stored at room temperature, or refrigerated or frozen.

Preferably, the formulations are sterile. A "sterile" formulation, as used herein, means a formulation that has been brought to a state of sterility and has not been subsequently exposed to microbiological contamination, i.e., the container holding the sterile composition has not been compromised. Sterile compositions are generally prepared by pharmaceutical manufacturers in accordance with current Good Manufacturing Practice ("cGMP") regulations of the U.S. Food and Drug Administration.

In some embodiments, sterile pharmaceutical formulations can be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the formulations can be sterile filled into a container to avoid the heat stress of terminal sterilization.

In some embodiments, the formulations are terminally sterilized using moist heat. Terminal sterilization can be used to destroy all viable microorganisms within the final, sealed container containing the pharmaceutical formulation. An autoclave is typically used to accomplish terminal heat-sterilization of drug products in their final packaging. Typical autoclave cycles in the pharmaceutical industry to achieve terminal sterilization of the final product are 121° C. for at least 10 minutes.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Where the term "about" is used, it is understood to reflect+/−10% of the recited value. In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control. Section and table headings are not intended to be limiting.

EXAMPLES

Example 1: Detection System

One embodiment of the detection system of the present invention is shown in FIG. 1.

The digital detection device comprises a food collection mechanism, a drill or macerating member, an optional pump or vacuum for facilitating flow through, one or more excitation means (e.g., an LED), one or more filters to receive the emitted light from the excitation means, a readout mechanism and a user interface screen.

The cartridges or disposable or interchangeable portion of the device may comprise one or more collection probes with optional covers, the allergen specific cartridge, one or more excitation means (e.g., LED lights) and one or more filters.

Example 2: Design of Aptamers as Signaling Polynucleotides

In this proof-of-concept example, two previously known aptamer sequences were used to design three different signaling polynucleotides. An aptamer against the Ara h 1 protein allergen is described by Tran et al. in *Selection of aptamers against Ara h 1 protein for FO-SPR biosensing of peanut allergens in food matrices*. Biosensors and Bioelectronics, 2013, 43, 245-251 (incorporated herein by reference in entirety). The sequence of this aptamer is shown below.

(SEQ ID NO: 1)
5'CGCACATTCCGCTTCTACCGGGGGGGTCGAGCTGAGTGGATGCAATC
TGTGGGTGGGCCGTAAGTCCGTGTGTGCGAA3'

The original aptamer of SEQ ID NO: 1 was modified to add a 5'-T residue to improve the functioning of the fluorophore-quencher pair. Fluorescein was then linked to the 5'-T residue as shown below.

(SEQ ID NO: 2)
5'FluoresceinTCGCACATTCCGCTTCTACCGGGGGGGTCGAGCTGAG
TGGATGCGAATCTGTGGGTGGGCCGTAAGTCCGTGTGTGCGAA3'

A 9-nucleotide linker with a 3"-DABCYL quencher was designed as shown below to be complementary to the first ten residues of the 5'-end of the T-modified aptamer of SEQ ID NO: 2.

3'DABCYLAGCGTGTAA5' (SEQ ID NO: 3)

The 9-nucleotide linker (SEQ ID NO: 3) was then annealed to the 5'-end of the main modified anti-peanut allergen aptamer sequence (SEQ ID NO: 2) to bring the fluorescein fluorophore into proximity with the DABCYL quencher moiety. The structure of the assembled signaling polynucleotide for detection of peanut allergen Ara h 1 is shown below.

```
              3'DABCYLAGCGTGTAA5'
(SEQ ID NO: 3)
                 |||||||||
5'FluoresceinTCGCACATTCCGCTTCTACCGGGGG
GGTCGAGCTGAGTGGATGCGAATCTGTGGGTGGGCCGT
AAGTCCGTGTGTGCGAA3'
(SEQ ID NO: 2)
```

Figure 4:
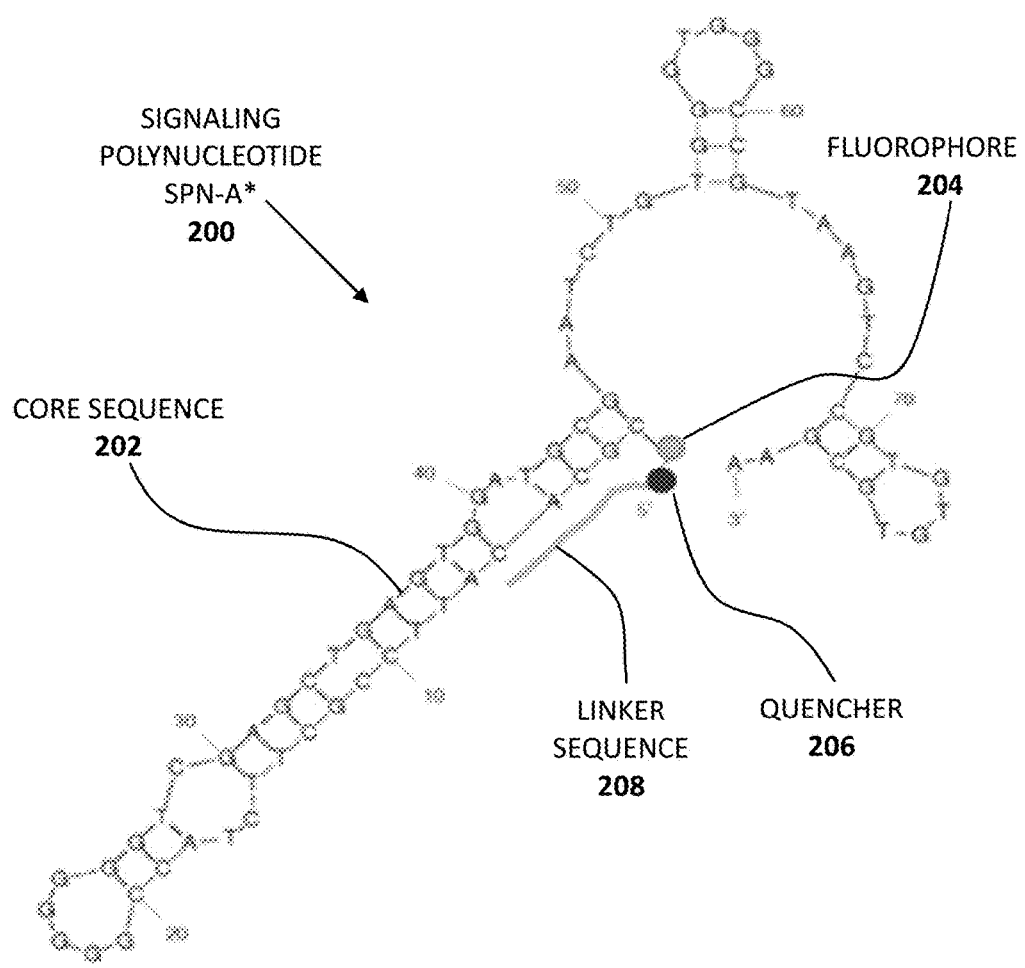
FIG. 4 shows the secondary sequence of a detection molecule represented by signaling polynucleotide SPN-A* 200 which comprises core sequence 202, fluorophore 204, quencher 206 and linker sequence 208.

The signaling polynucleotide prepared from annealing SEQ ID NOs: 2 and 3 is a dimeric entity herein designated SPN-A*. The secondary structure of SPN-A* is shown in FIG. 4. The arrangement of the components of the signaling polynucleotide 200 are core sequence 202, fluorophore 204, quencher 206 and linker sequence 208.

In a similar manner, a signaling polynucleotide was designed based upon the sequence of an aptamer against egg white lysozyme described by Tran et al. in *Selection and Characterization of DNA Aptamers for Egg White Lysozyme*. Molecules 2010, 15(3), 1127-1140 (incorporated herein by reference in entirety). The sequence of this aptamer is shown below.

(SEQ ID NO: 4)
5'GCAGCTAAGCAGGCGGCTCACAAAACCATTCGCATGCGGC3'

The original aptamer of SEQ ID NO: 4 was modified to add a 5'-T residue to improve the functioning of the fluorophore-quencher pair. Fluorescein was then linked to the 5'-T residue as shown below.

(SEQ ID NO: 5)
5'FluoresceinTGCAGCTAAGCAGGCGGCTCACAAAACCATTCGCATG
CGGC3'

A 10-nucleotide linker with a 3'-DABCYL quencher was designed as shown below to be complementary to the first ten residues of the 5'-end of the T-modified aptamer of SEQ ID NO: 5.

(SEQ ID NO: 6)
3'DABCYLACGTCGATTC5'

The 10-nucleotide linker (SEQ ID NO: 6) was then annealed to the 5'-end of the main modified anti-lysozyme aptamer sequence (SEQ ID NO: 5) to bring the fluorescein fluorophore into proximity with the DABCYL quencher moiety. The structure of the assembled signaling polynucleotide for detection of lysozyme is shown below.

```
                3'DABCYLACGTCGATTC5'
(SEQ ID NO: 6)
                    ||||||||||
5'FluoresceinTGCAGCTAAGCAGGCGGCTCACAAA
ACCATTCGCATGCGGC3'
(SEQ ID NO: 5)
```

Figure 6:
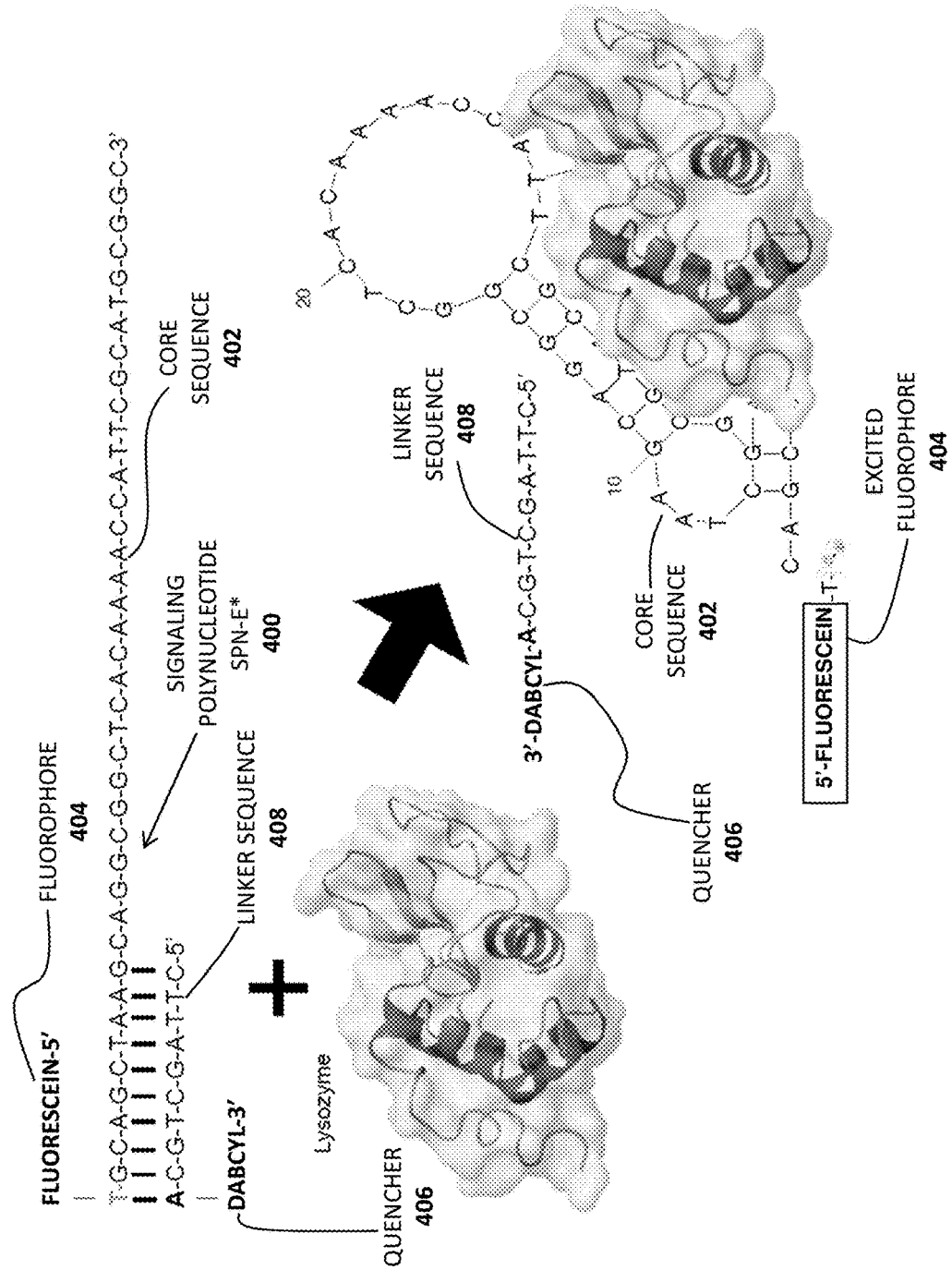
FIG. 6 shows a reaction between a detection molecule represented by a dimeric signaling polynucleotide SPN-E* 400 (including an annealed linker sequence 408) with its target molecule lysozyme. Also shown are the aptamer core sequence 402, the fluorophore 404 and the quencher 406.
Figure 7A:
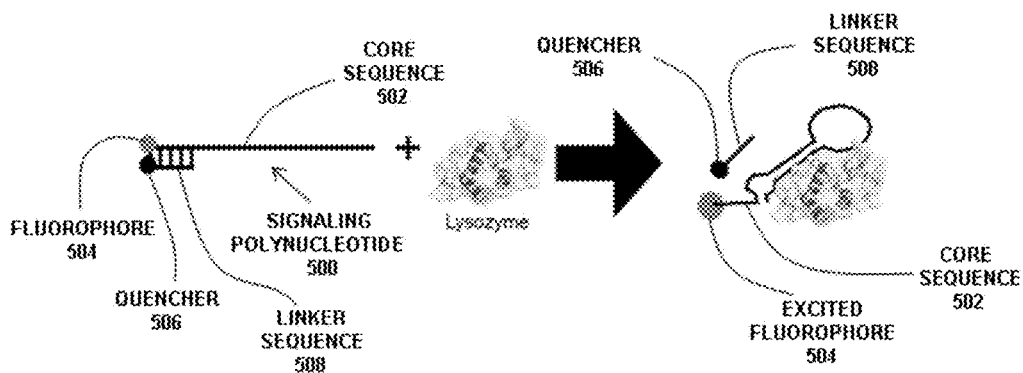
FIG. 7A shows a reaction between a generic signaling polynucleotide 500 and lysozyme as the molecular target. The signaling polynucleotide 500 has a core sequence 502 with a linked fluorophore 504. The signaling polynucleotide 500 also includes a linker sequence 508 with a linked quencher 506. The linker sequence 508 is annealed to the core sequence 502 thereby bringing the quencher 506 into close proximity with the fluorophore 504. Binding of lysozyme to the core sequence 502 generates a secondary structure with a hairpin that causes release of the linker sequence 508 such that the quencher 506 no longer quenches fluorescence of the fluorophore 504.
Figure 7B:
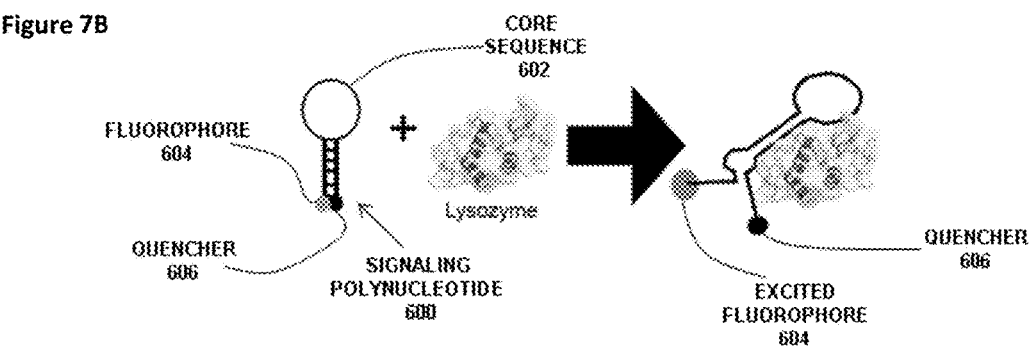
FIG. 7B is a reaction between a generic hairpin-type signaling polynucleotide 600 and lysozyme as the molecular target. The signaling polynucleotide 600 has a core sequence 602 with a linked fluorophore at the 5'-end and a linked quencher 606 at the 3'-end. The core sequence 602 has a hairpin section which brings the quencher 606 into sufficient proximity to the fluorophore 604 to quench its fluorescence. Binding of lysozyme to the core sequence 602 disrupts the hairpin structure and causes the quencher 606 to move away from the fluorophore 604 such that quencher 606 no longer quenches fluorescence of the fluorophore 604.

The dimeric signaling polynucleotide prepared from SEQ ID NOs: 5 and 6 is herein designated SPN-E*. A reaction between SPN-E* and lysozyme is shown schematically in FIG. 6. The arrangement of the components of the signaling polynucleotide SPN-E* 400 are core sequence 402, fluorophore 404, quencher 406 and linker sequence 408. It is seen that binding of lysozyme disrupts the hairpin structure and causes the fluorophore 404 to move away from the quencher 406, thereby allowing the fluorophore 404 to fluoresce upon excitation.

A third signaling polynucleotide was designed based upon the aptamer sequence of SEQ ID NO: 4 described above. A 5'-T residue was appended to SEQ ID NO: 4 and the 3'-end was modified by addition of a five nucleobase segment complementary to the last five nucleobases of the 5'-end of the original aptamer sequence of SEQ ID NO: 4. Then 5'-fluorescein and 3"-DABCYL moieties were linked to produce the sequence shown below (SEQ ID NO: 7) wherein the additional five nucleobase segment is underlined along with the first five nucleobases at the 5'-end of the original aptamer sequence (not including the added the 5'-T residue).

```
                                         (SEQ ID NO: 7)
5'FluoresceinTGCAGCTAAGCAGGCGGCTCACAAAACCATTCGCATG
CGGCGCTGCDABCYL3'
```

This signaling polynucleotide is a hairpin entity herein designated SPN-E. It will be recognized that the underlined residues at the 5"-end and the 3"-end are complementary for the purpose of forming a hairpin secondary structure as shown in the leftmost structure of FIG. 5 (core sequence 302). This structure brings the fluorophore 304 and quencher 306 into close proximity with each other to allow the quencher 306 to quench the fluorophore 304. The binding of the signaling polynucleotide to lysozyme can disrupt the hybridization of the two ends of the signaling polynucleotide 300 as shown in the rightmost structure of the core sequence 302, resulting in separation of the fluorophore 304 from the quencher 306, thereby activating the fluorophore 304.

Example 3: Procedure for Obtaining Fluorescence Readings for Hairpin-Type Signaling Polynucleotides in Detection of a Target Molecule This example describes one procedure for obtaining fluorescence readings and thereby determining the effectiveness of signaling polynucleotides in identifying and quantifying the presence of a molecular target such as a protein. This procedure is useful for detection of hairpin-type signaling polynucleotides such as SPN-E as well as dimeric signaling polynucleotides such as SPN-E* and SPN-A*, for example.

The protein of interest is diluted to an appropriate concentration in double-distilled water. The signaling polynucleotide is diluted to 200 μM in 10 mM TRIS-HCl, pH 7.5. This solution is heated to 99° C. for 3 minutes and then cooled to room temperature. As an alternative to TRIS-HCl, PBS or tris(hydroxyamino)methane-glycine-potassium buffer (TGK buffer) at pH 8.3 may be used. The protein solution is added to the wells of a 96-well plate and then the signaling polynucleotide is added to each well, as quickly as possible using a multi-pipettor. Fluorescence readings are then taken at 2 minute intervals for a period of 40 minutes.

Example 4: Procedure for Obtaining Fluorescence Readings for Dimeric Signaling Polynucleotides This example describes a procedure for obtaining fluorescence readings and thereby determining the effectiveness of signaling polynucleotides in identifying and quantifying the presence of a molecular target such as a protein. This procedure is useful for detection of partially double-stranded signaling polynucleotides such as SPN-A* and SPN-E*, for example.

The core sequences of signaling polynucleotides SPN-A* and SPN-E* (SEQ ID NOs: 2 and 5, respectively) are re-suspended in 10 mM TRIS-HCl, pH 7.5, each to a concentration of 200 μM. These solutions are then heated for 5 minutes within a temperature range from about 95° C. to about 100° C. The corresponding 10-nucleobase DABCYL-linked strands (SEQ ID NOs: 3 and 6 for SPN-A* and SPN-E*, respectively) are then added and the mixtures are allowed to cool to room temperature in the dark for 30 minutes to promote annealing. After 30 minutes, the signaling polynucleotide mixture is diluted to 100 μM.

A series of serial dilutions of lysozyme are prepared as described in Table 1.

TABLE 1

Preparation of Lysozyme Dilutions for a Signaling Polynucleotide Detection Experiment

| Starting Lysozyme Concentration | Dilution Factor | Solution Preparation | Sample No. |
| --- | --- | --- | --- |
| 50 mg/mL | — | — | L1 |
| 5 mg/mL | 1:10 | 50 μL of L1 in 450 μL TRIS buffer | L2 |
| 0.5 mg/mL | 1:10 | 50 μL of L2 in 450 μL TRIS buffer | L3 |
| 0.05 mg/mL | 1:10 | 50 μL of L3 in 450 μL TRIS buffer | L4 |
| 5 μg/mL | 1:10 | 50 μL of L4 in 450 μL TRIS buffer | L5 |
| 0.5 μg/mL | 1:10 | 50 μL of L5 in 450 μL TRIS buffer | L6 |
| 0.05 μg/mL | 1:10 | 50 μL of L6 in 450 μL TRIS buffer | L7 |
| 5 ng/mL | 1:10 | 50 μL of L7 in 450 μL TRIS buffer | L8 |
| 0.5 ng/mL | 1:10 | 50 μL of L8 in 450 μL TRIS buffer | L9 |

A series of dilutions of peanut butter in PBS are prepared as described in Table 2.

TABLE 2

Preparation of Peanut Butter Dilutions for a Signaling Polynucleotide Detection Experiment

| Starting Peanut Butter Concentration | Dilution Factor | Solution Preparation | Sample No. |
| --- | --- | --- | --- |
| 1 mg/mL | — | — | A3 |
| 10 μg/mL | 1:10 | 50 μL of A3 in 450 μL TRIS buffer | A1 |
| 0.1 μg/mL | 1:10 | 50 μL of A1 in 450 μL TRIS buffer | A2 |

Dilutions of egg white are also prepared, starting from whole raw egg white diluted 1:1 in PBS (sample E1). This original preparation is then diluted 1:10 to generate sample E2, 1:100 to generate sample E3 and 1:1000 to generate sample E4.

In one experiment, 60 μL of the protein solutions was added to 96-well plates and 60 μL of signaling polynucleotide at a concentration of 50 μM was then added. Controls included signaling polynucleotide alone (wells 8 and 9), buffer (well 10) and signaling polynucleotide combined with bovine serum albumin (BSA—wells 11 and 12). The arrangement of samples in the 96-well plate is shown below in Table 3.

TABLE 3

Sample Placement in 96-well Plate for Preliminary Experiment

| Well 1 | Well 2 | Well 3 | Well 4 | Well 5 | Well 6 | Well 7 | Well 8 | Well 9 | Well 10 | Well 11 | Well 12 |
|---|---|---|---|---|---|---|---|---|---|---|---|
| L2 | L5 | L8 | E1 | E4 | A2 | A5 | SPN-E* | SPN-A* | Buffer | BSA + SPN-E* | BSA + SPN-A* |

The results of this experiment indicated that the protein and signaling polynucleotide concentrations could be decreased. The starting concentration of signaling polynucleotide was reduced from 200 μM to 100 μM. Mixed protein solutions comprising skim milk (0.1 mg/mL and 0.01 mg/mL diluted in PBS) were also investigated. An additional control comprising egg yolk diluted in the same manner as the egg white (described above) was also added. Additional mixtures of egg white and egg yolk were prepared (1:2, 1:20 and 1:20,000). It was advantageous to obtain fluorescence readings within 2 minutes of mixing the signaling polynucleotide with the protein solution. The signaling polynucleotide+BSA control sampling was repeated three times to ensure that a stable control was present. If various concentrations of signaling polynucleotide are being investigated, the corresponding concentrations of signaling polynucleotide+BSA control samples can be assessed concurrently. It is advantageous to read an entire plate of samples to ensure stability of the fluorescence signal.

Example 5: Signaling Polynucleotide Proof-of-Concept Experiments

Figure 8:
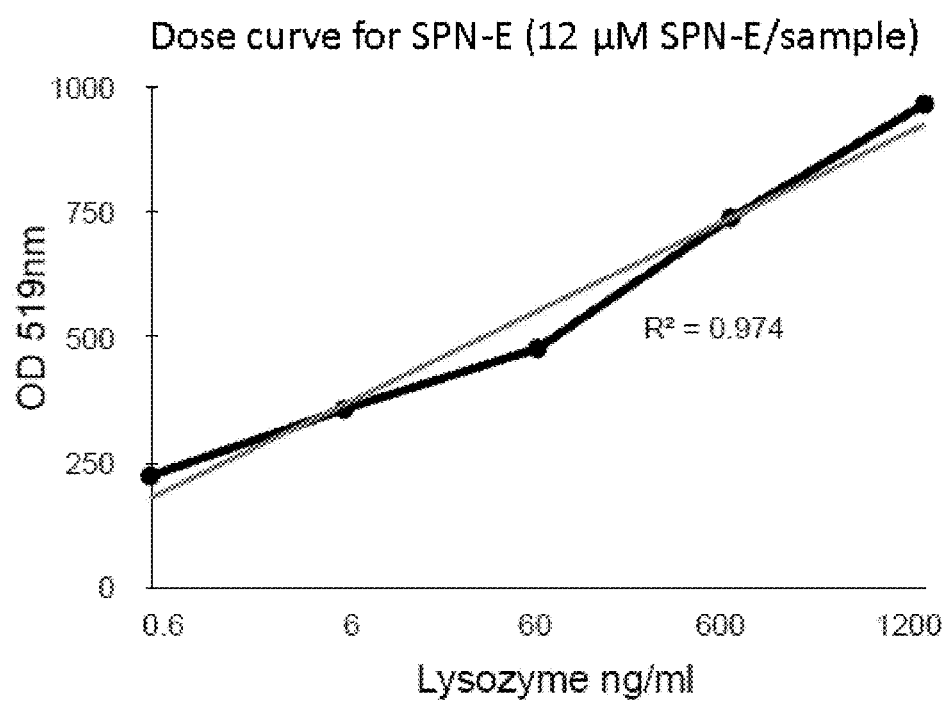
FIG. 8 is a plot of fluorescence detection of lysozyme by SPN-E (optical density at 519 nm vs. concentration of lysozyme).

The general protocol developed on the basis of the preliminary experiments described in Example 4 is described below.
General Protocol Protein samples are diluted to specified concentrations in PBS. The signaling polynucleotide solutions are prepared at 200 μM in 10 mM TRIS-HCl, pH 7.5, heated to 99° C. for 3 minutes and then cooled to room temperature for 20 minutes. Volumes of 60 μL of protein solutions are added to the wells of a 96-well plate. Signaling polynucleotides are added to the wells as soon as possible after the addition of the protein samples. Fluorescence readings are taken immediately with all readings obtained at 25° C. with an excitation wavelength of 495 nm and emission monitored at the fluorescence peak of 519 nm. The signaling polynucleotides were synthesized by TriLink Biotechnologies (San Diego, Calif.), pure lysozyme was obtained from Pierce (Thermoscientific) and BSA was obtained from Sigma Aldrich.
Detection of Lysozyme by the Signaling Polynucleotides SPN-E* and SPN-E An assay was performed to obtain a dose curve (12 μM of detection of signaling polynucleotide SPN-E per sample). The results are shown in FIG. 8 and indicate that SPN-E detects lysozyme concentrations ranging from 0.6 ng/mL to 1200 ng/mL, translating to less than 50 pg of lysozyme per sample.

Figure 9A:
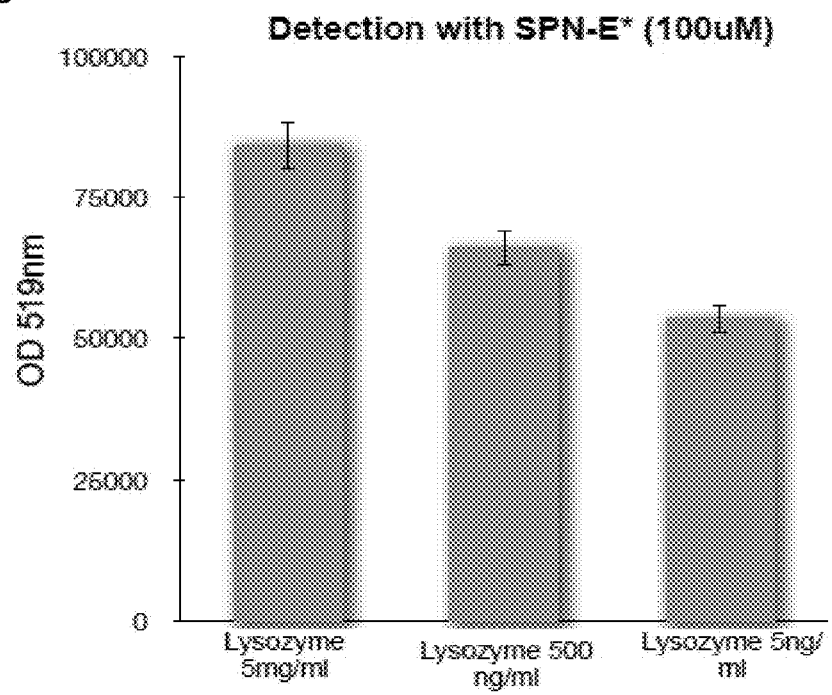
FIG. 9A is a bar chart showing the extent of fluorescence detection of lysozyme by SPN-E* (optical density at 519 nm) for three samples with varying concentrations of lysozyme.
Figure 9B:
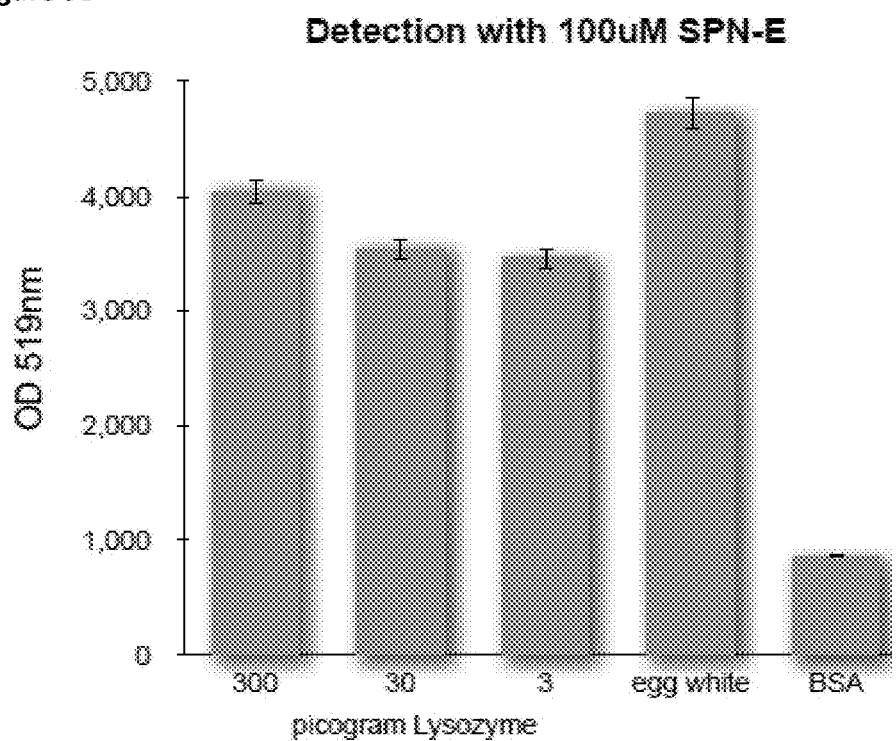
FIG. 9B is a bar chart showing the extent of fluorescence detection of lysozyme by SPN-E (optical density at 519 nm) for three samples containing varying picogram amounts of lysozyme as well as samples containing egg white and BSA. Egg white naturally contains lysozyme.

The data plotted in FIG. 9A indicate that SPN-E* at a concentration of 100 μM detects lysozyme at a 5 ng/mL concentration and increases the detection level to 3 pg/sample. The data plotted in FIG. 9B indicate that SPN-E can be used to detect lysozyme in unprocessed egg white which was diluted 1:20 (sample size was 30 μL). SPN-E gave a minimal signal with BSA as the negative control protein.

Figure 10:
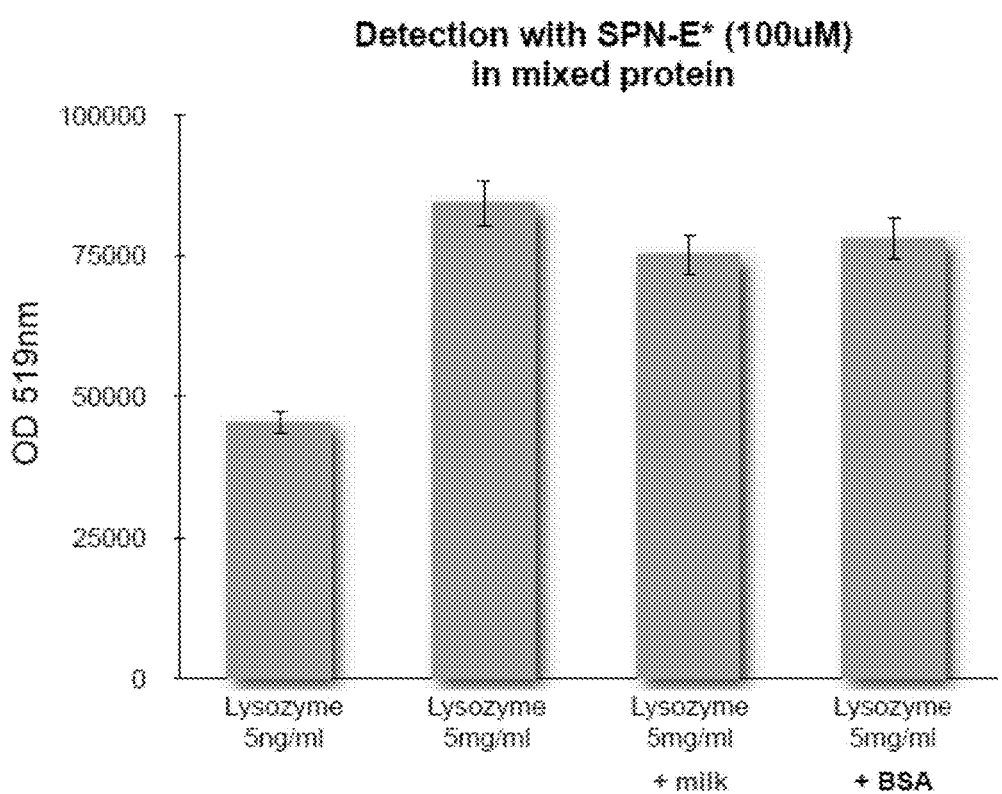
FIG. 10 is a bar chart showing the extent of fluorescence detection of lysozyme by SPN-E* (optical density at 519 nm) for four samples containing varying concentrations of lysozyme, including two samples with lysozyme mixed with milk or BSA.

The data plotted in FIG. 10 indicate that detection of lysozyme in a mixed protein solution by SPN-E* at 100 μM is not significantly altered when this protein is mixed with milk or with BSA.

Figure 11A:
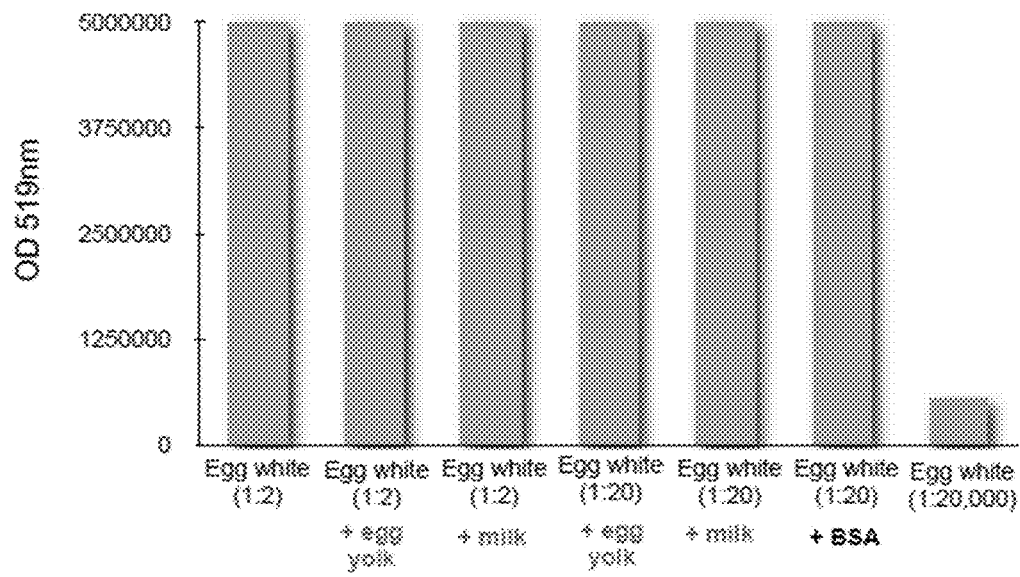
FIG. 11A is a bar chart showing the extent of fluorescence detection of lysozyme by SPN-E* (optical density at 519 nm) for a series of seven samples with varying dilutions of egg white either alone or in mixed protein solutions. Egg white naturally contains lysozyme.
Figure 11B:
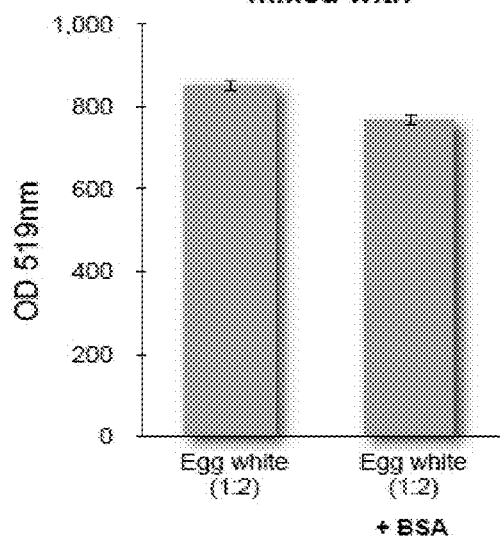
FIG. 11B is a bar chart showing the extent of fluorescence detection of lysozyme by SPN-E (optical density at 519 nm) by SPN-E for diluted egg white alone and diluted egg white in a mixed protein solution (BSA). Egg white naturally contains lysozyme.

The data plotted in FIG. 11A indicate that SPN-E* can be used to detect minute levels of egg white, regardless of the protein with which it is mixed. SPN-E* at 100 μM can detect egg white diluted 1:20,000 (sample size 30 μL). Mixing of egg white with egg yolk or with milk did not significantly decrease the ability of SPN-E* to detect the presence of egg white. The data plotted in FIG. 11B indicate that SPN-E also detected egg white regardless of the protein with which it is mixed. Decreased concentrations of SPN-E can still detect egg white diluted 1:20 (not shown—sample size 30 μL). When the egg white is mixed with the control protein BSA, the detection was not significantly decreased.

Figure 12:
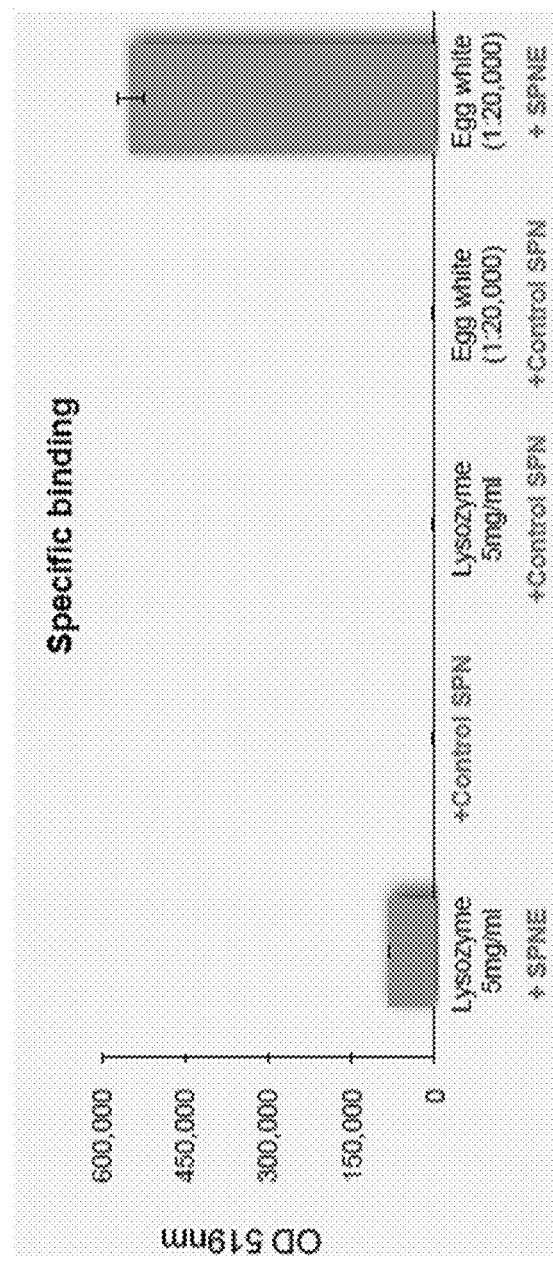
FIG. 12 is a bar chart demonstrating the specific binding of SPN-E to lysozyme. Egg white naturally contains lysozyme.

In another experiment designed to assess the specific binding, both lysozyme and egg white were treated with a control signaling polynucleotide comprising a short antisense strand of SPN-E. As indicated in FIG. 12, no signal was detected when protein samples were treated with the control signaling polynucleotide.
Detection of Peanut Allergen Ara h1 by the Signaling Polynucleotide SPN-A*

Figure 13A:
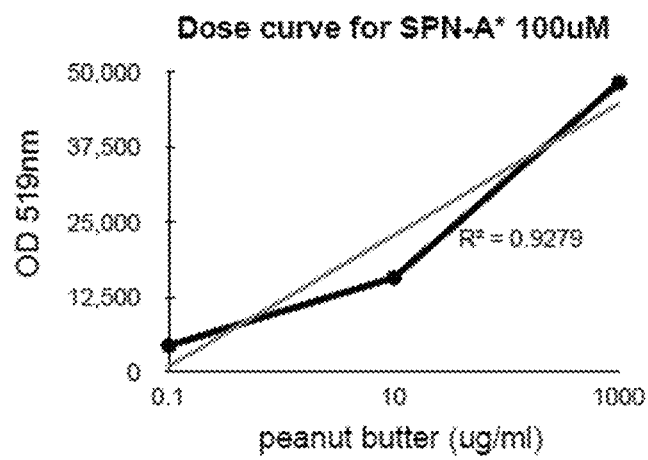
FIG. 13A is a plot of fluorescence detection of the peanut allergen ara h1 by SPN-A* (optical density at 519 nm vs. concentration of peanut butter).
Figure 13B:
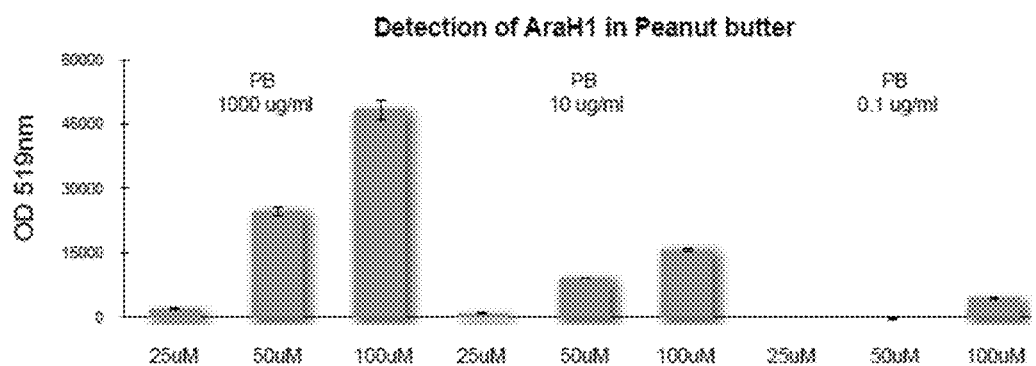
FIG. 13B is a bar chart showing fluorescence detection of the peanut allergen ara h1 by SPN-A* (optical density at 519 nm vs. concentration of peanut butter) for a series of samples containing varying concentrations of SPN-A* per sample.
Figure 14A:
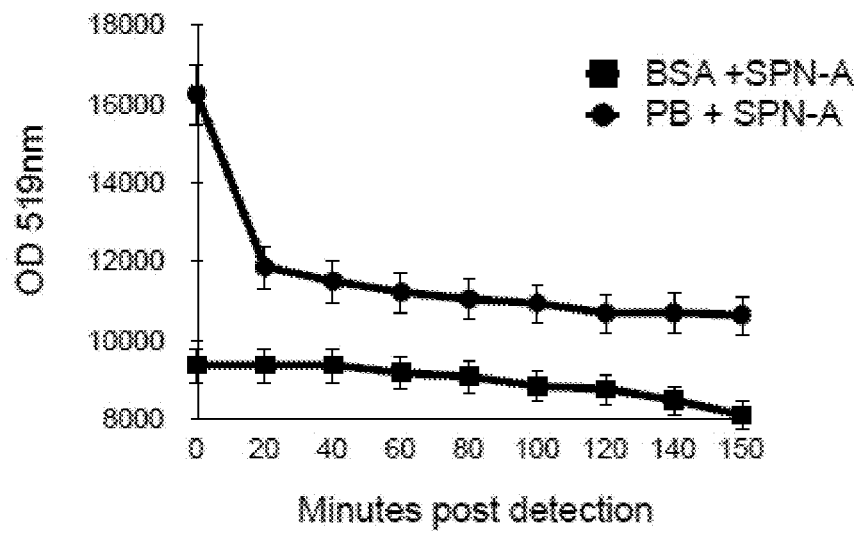
FIG. 14A is a plot of fluorescence detection of the peanut allergen ara h1 by SPN-A* (optical density at 519 nm) as a function of time after mixing of SPN-A* with a sample of peanut butter. A control plot with BSA is shown for comparison.
Figure 14B:
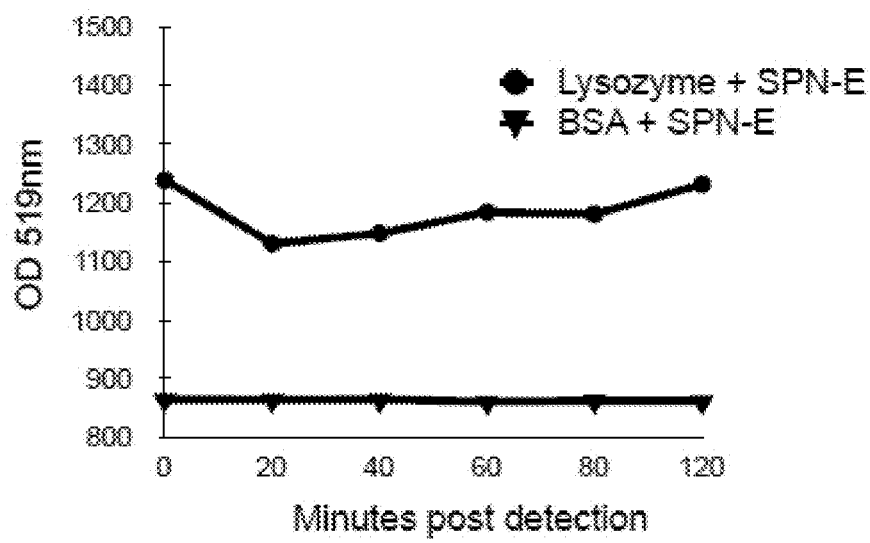
FIG. 14B is a plot of fluorescence detection of lysozyme by SPN-E (optical density at 519 nm) as a function of time after mixing of SPN-E with a sample of lysozyme. A control plot with BSA is shown for comparison.

In this experiment, the ability of SPN-A* to detect the peanut allergen Ara h1 in peanut butter (reduced fat Skippy™) was tested. Peanut butter contains roasted peanuts as well as other ingredients. Approximately 1 mg of peanut butter was obtained on a toothpick and diluted in 1 mL of PBS. No heating or centrifugation steps were involved. The data shown in FIGS. 13A and 13B indicate that SPN-A* detected the Ara h1 allergen in peanut butter concentrations ranging from 0.1 μg/mL to 1 mg/mL.
Stability of Fluorescence Signals of SPN-A and SPN-E The stability of fluorescence signals of SPN-A and SPN-E was determined. As shown in FIG. 14A, the fluorescence signal of SPN-A decreased by about 30% after a period of about 20 minutes after mixing with the protein sample. The signal remained relatively stable for at least three hours. Shown in FIG. 14B is a similar plot for SPN-E where the fluorescence signal of SPN-E was observed to decrease by about 12% after mixing with the protein sample. The signal remained stable for at least 2 hours.

Advantages of Signaling Polynucleotides Over ELISA

The signaling polynucleotides can be used in a wide range of concentrations and have been shown to effectively bind at concentrations as low as 6 µM and as high as 100 µM. The detection time is instant and the detection signals are stable for at least 2 hours. One of the lysozyme signaling polynucleotides was shown to detect lysozyme at concentrations as low as 0.6 ng/mL.

The signaling polynucleotides are capable of detecting lysozyme in 10 mM Tris-HCl buffer as well as in PBS.

The signaling polynucleotides of both types (the stem-loop structure as well as the single strand structure with the annealed linker sequence) were capable of detecting protein in food matrixes. The signaling polynucleotides designed to detect lysozyme (SPN-E and SPN-E*) are capable of detecting lysozyme in egg white, mixed egg-white and egg yolk, egg white mixed with skim milk, and egg white mixed with BSA.

The signaling polynucleotide designed to detect Ara h1 was demonstrated to be capable of detecting this allergen in peanut butter.

All experiments were performed at room temperature, thereby indicating that the signaling polynucleotides are stable at room temperature.

Table 4 indicates a series of parameters derived from the experiments described above, which indicate advantages of the use of signaling polynucleotides for detection of molecular targets, in comparison with the currently more widely used ELISA techniques. These parameters indicate that detection assays based on signaling polynucleotides have definite advantages over and may replace ELISA techniques.

TABLE 4

Comparison of Signaling Polynucleotide-based Detection Methods with ELISA

| Parameter | ELISA | Signaling Polynucleotide |
|---|---|---|
| Sensitivity | 3 ng/mL | 0.5 ng/mL |
| Time | 4-48 hours | Seconds |
| Stability of Signal | 30 minutes | at least 150 minutes |
| Temperature | 4° C. | Room temperature |
| Concentration of Detection Agent Required | 1-10 µg/mL | 0.001 µg/mL |

Example 6: Other Aptamers Useful in Allergen Detection and Diagnostic Devices

Other aptamer sequences are useful in the presently disclosed devices and methods. For example, aptamers against immunoglobulin E (IgE) as well as lupin and gliadin protein allergens have been described; exemplary sequences are shown below.

11-mer SGQ aptamer against Lup an 1 (β-conglutin) has the nucleotide sequence: 5' GGTGGGGGTGG 3' (SEQ ID NO: 8). (See Nadal et al., 2013, Anal. Bioanal. Chem. 405:9343-9349, incorporated herein by reference in its entirety).

A single-stranded DNA aptamer capable of recognizing and binding specifically to gliadin has the nucleotide sequence: 5' AAACTACTAACTAGGTAAGATCACGCAGCACTAAACGACGTAGTTGCCA 3' (SEQ ID NO: 9) (Pinto, et al., 2014, *Label-free detection of gliadin food allergen mediated by real-time apta-PCR*. Anal. Bioanal. Chem. 406(2):515-24; incorporated herein by reference in its entirety).

Aptamers have also been designed to target immunoglobulin E (IgE), a known biomarker associated with atopic allergic diseases. In a comparison of the performance of aptamer-based and antibody-based quartz crystal microbalance (QCM) biosensors for the detection of immunoglobulin E (IgE) in human serum, and a lower detection limit could be observed in the aptamer-based biosensor. The base sequence for the anti-IgE aptamer (D17.4) was identified as 5' GGGGCACGTTTAT-CCGTCCCTCCTAGTGGCGTGCCCC 3' (SEQ ID NO: 11) (Yao, et al., *Development of a Quartz Crystal Microbalance Biosensor with Aptamers as Bio-recognition Element*. Sensors 2010, 10:5859-5871; incorporated herein by reference in its entirety). Another DNA aptamer against IgE was designed to have the following sequence: 5' GCGCGGGGCACGTTTATCCGTCCCTCCTAGTGGCGTGCCCCGCGC 3' (SEQ ID NO: 12) (Wang, et al., *Fluorescence protection assay: a novel homogeneous assay platform toward development of aptamer sensors for protein detection*. 2011, Nucleic Acids Research, 39(18) e122).

Example 7: Optimization of Digestion Buffer

The first step in creating an SPN allergen detection platform is to optimize and unify the protein extraction process with a fast, accurate and universal protocol that allows detection of allergen in any food matrix. Various extraction buffer protocols that will include reduction, and blocking agents, detergents and surfactants.

The chemicals that are suitable for universal sampling are tested and optimized (listed in Table 5) and buffers may be used for this purpose are listed in Table 6.

TABLE 5

Chemicals for Protein Extraction Buffer and Justification

| Chemicals | Justification |
|---|---|
| Beta-Mercaptoethanol 0.5-5% | A mild reducing agent for cleaving protein disulfide bonds |
| Dithiothreitol (DTT) 0.2-2.5% | A strong reduction agent used to reduce the disulfide bounds of proteins and prevent intramolecular and intermolecular disulfide bonds from forming between cysteine residues of proteins. |
| Deoxycholate sodium | An ionic detergent that is especially useful for disrupting and dissociating protein interactions, commonly used in protein methods. chromatography and a cell culture media supplement. |

TABLE 5-continued

Chemicals for Protein Extraction Buffer and Justification

| Chemicals | Justification |
|---|---|
| Sodium Dodecyl Sulfate (SDS) | SDS is a very effective surfactant in solubilizing almost all proteins. It disrupts non-covalent bonds within and between proteins; thus it denatures them, resulting in the loss of their native conformation and function. |
| NP-40/ Triton100/ Tween20 | Mild surfactant used to break the protein-protein, protein-lipid and lipid-lipid associations, denature proteins and other macromolecules and prevent unspecific binding |
| $MgCl_2$/KCl | Adding $MgCl_2$ or KCl can affect the Tm of the SPN. Tm in the presence of $MgCl_2$ is higher pushing towards the double strand/inactive structure. Tm with either NaCl or KCl is lowered pushing towards the active SPN binding the protein. |
| Gelatin/BSA/ Skim milk | Inhibit non-specific binding of SPNs. |

TABLE 6

Protein Extraction Buffers

| Buffer base | pH | Reduction agents | Agents effect double helix of SPN | Surfactants/ Detergents | Inhibitors of non-specific binding |
|---|---|---|---|---|---|
| PBS (Phosphate Buffer Saline) | 7.4-8.5 | Beta-Mercaptoethanol (0.5-5%) | MgCl (5-10 mM) | NP-40 (0.5-5%) | Gelatin (0.1-1%) |
| Tris-HCl (50-150 mM) | 7.4-8.5 | DTT (0.2-2.5%) | KCl (1-5 mM) | Tween (0.5-5%) Triton (0.5-5%) Deoxycholate sodium (0.1-0.5%) | BSA (0.5-5%) Skim-milk (1-5%) |

A comparison of these tested buffers to known extraction buffers used in the food allergen field today primarily for ELISA testing, by testing at least three different ELISA assay for each allergen protein is performed. The optimal extraction buffer may be selected through a structured process that will test and compare up to 20 different food matrices known to be tested in the optimization of ELISA assays (baked goods, sausages, soups, ice cream etc. Table 7) as well as more challenging food matrices (salad dressing, soy sauce and chocolate). Uniformity of matrix will be established by using the protein extraction program on the gentle MAC dissociator.

As an example of a selection process, about 0.5 mg food sample is spiked with known amounts of allergens before and after processing (baking, boiling, frying etc.). Total protein extraction as well as specific allergen retrieval is tested and recorded to compare efficiency of different extraction buffers. The readout will be total protein extraction and relative recovery of specific allergen (% of amount spiked). The deliverable will be a table comparing the total protein, specific allergen recovery (such as egg, wheat, peanut, fish, crustacean, milk, cashew, soy) before and after processing in 3 different buffers compared to 3 different extraction buffers from commercial ELISA assays.

Once an optimal buffer has been selected, the extraction time is decreased by accelerating the homogenization process. This can be achieved by changing blade positioning and size, increasing RPM of blending, and decreasing buffer to sample ratios. Additionally, the debris particles as well as larger protein complexes are eliminated by filtering the homogenized solution through a low protein-binding filter such as commercially available PES Polyethersulfone, PCTE (Polycarbonate), or polyvinylidene difluoride (PVDF).

TABLE 7

Examples of food matrices

| Food Category | Examples of food tested | Allergens tested | Testing procedure | Deliverable |
|---|---|---|---|---|
| Baked Goods | Cake | Wheat, egg, milk, soy, fish, crustaceans, | Measured amounts of allergens will be spiked before and after baking. Total allergen recovery | Determine specific allergen recovery pre and post processing. Determine SPN |

TABLE 7-continued

Examples of food matrices

| Food Category | Examples of food tested | Allergens tested | Testing procedure | Deliverable |
|---|---|---|---|---|
| | | peanut, cashew | will be tested. | binding specificity in processed and unprocessed samples. Determine SPN binding specificity compared to ELISA assay. |
| Baked Goods | Bread | Gluten | Test bread and gluten free breads, spike gluten free breads with increasing levels of gluten and determine the minimum level of gluten detected. | Determination of gluten recovery range. Determine SPN binding specificity in processed and unprocessed samples. Determine SPN binding specificity compared to ELISA assay. |
| Baked Goods | Cookies | Gluten, milk, egg, peanut and cashew | Test food samples that indicate the presence of a specific allergen and compare to food that have a label indicating the presence of "traces" of the allergen. | Determination of specific allergen recovery range. Determine SPN binding range of "traces" of allergens. Determine SPN binding specificity compared to ELISA assay. |
| Dairy | Strawberry Pudding (non refrigerated) | milk | Test for milk allergen protein recovery in food sample with high levels of food coloring and preservatives. Test at different dilution of sample. | Determination of milk allergen recovery range in processed sample. Determine SPN binding capabilities in highly processed food. Determine SPN binding specificity compared to ELISA assay. |
| Dairy | Peanut butter cup ice cream | Milk, peanuts | Test for milk and peanut allergen protein recovery in complex food sample that includes milk, chocolate and peanuts butter. Frozen matrix. | Determine the effect of freezing on allergen protein recovery and SPN binding. Determine the effect of chocolate on peanut and milk allergen protein recovery and SPN binding. Determine SPN binding specificity compared to ELISA assay. |
| Dairy | Cheddar Cheese | Milk | Test the cheddar cheese at different temperatures - cold and melted. Test for milk allergen. | Determine the effect of heating on allergen protein recovery and SPN binding. Determine SPN binding specificity compared to ELISA assay. |
| Dairy | Baby formula | Soy, milk | Test milk and soy based baby formula and compare the presence of allergens. Dilute samples to determine minimum and maximum protein recovery and detection capabilities. | Determination of specific allergen recovery range. Determine SPN binding range of minute allergen concentrations. Determine SPN binding specificity compared to ELISA assay. |
| Snack | Peanut butter filled pretzels | Gluten, eggs and peanuts | Test allergen protein recovery from high fat, processed foods which include different food textures. Dilute samples to | Determination of specific allergen recovery range from high fat processed samples. Determine SPN |

TABLE 7-continued

Examples of food matrices

| Food Category | Examples of food tested | Allergens tested | Testing procedure | Deliverable |
|---|---|---|---|---|
| | | | determine minimum and maximum protein recovery and detection capabilities. | binding in high fat samples. Determine SPN binding specificity compared to ELISA assay. |
| Snack | Twinkies (TWINKIE ®) | Milk, gluten, eggs and soy | Test allergen protein recovery from high fat, processed foods which include different food textures. Dilute samples to determine minimum and maximum protein recovery and detection capabilities. | Determination of specific allergen recovery range from high fat processed samples. Determine SPN binding in high fat samples. Determine SPN binding specificity compared to ELISA assay. |
| Meat | Cheese and pork sausages | Milk and soy | Test allergen protein recovery from high fat, processed foods which include meat/high protein content. Dilute samples to determine minimum and maximum protein recovery and detection capabilities. | Determination of specific allergen recovery range from meat samples. Determination of specific allergen recovery range from processed meat samples Determine SPN binding in processed meat samples. Determine SPN binding specificity compared to ELISA assay. |
| Meat | Chicken Nuggets | Gluten, soy, milk and eggs | Test allergen protein recovery from high fat, processed foods which include meat/high protein content. Dilute samples to determine minimum and maximum protein recovery and detection capabilities. | Determination of specific allergen recovery range from meat samples. Determination of specific allergen recovery range from processed meat samples Determine SPN binding in processed meat samples. Determine SPN binding specificity compared to ELISA assay. |
| Fish | Clam Chowder | Fish and crustaceans | Test allergen protein recovery from high fat, processed foods, heated samples. Dilute samples to determine minimum and maximum protein recovery and detection capabilities. | Determination of specific allergen recovery range from high fat processed and heated samples. Determine SPN binding in high fat samples. Determine SPN binding specificity compared to ELISA assay. |
| Fish | Instant lunch - ramen noodles - seafood | Soy, fish and crustaceans | Test allergen protein recovery from high fat, processed foods, heated samples. Dilute samples to determine minimum and maximum protein recovery and detection capabilities. | Determination of specific allergen recovery range from high fat processed and heated samples. Determine SPN binding in high fat samples. Determine SPN binding specificity compared to ELISA assay. |
| Crustaceans | Canned shrimp/crab | Fish and crustaceans | Test allergen protein recovery from processed | Determination of allergen recovery range |

TABLE 7-continued

Examples of food matrices

| Food Category | Examples of food tested | Allergens tested | Testing procedure | Deliverable |
|---|---|---|---|---|
| | | | foods. Dilute samples to determine minimum and maximum protein recovery and detection capabilities. | in processed sample. Determine SPN binding capabilities in highly processed food. Determine SPN binding specificity compared to ELISA assay. |
| Crustaceans | Instant lunch - ramen noodles - shrimp | Soy, fish and crustaceans | Test allergen protein recovery from high fat, processed foods, heated samples. Dilute samples to determine minimum and maximum protein recovery and detection capabilities. | Determination of specific allergen recovery range from high fat processed and heated samples. Determine SPN binding in high fat samples. Determine SPN binding specificity compared to ELISA assay. |
| Cashew | Almond and cashew milk | Cashew | Test cashew recovery from liquid maxtrix with mixed nuts, test for detection selectivity. Dilute samples to determine minimum and maximum protein recovery and detection capabilities. | Determination of cashew allergen recovery range from mixed nut liquid sample Determine SPN binding in mixed nut samples. Determine SPN binding specificity compared to ELISA assay. |
| Egg | Fried/boiled eggs | Egg | Determine the allergen protein recovery following different processes comparing raw, boiled and fried eggs. | Determination of egg allergen recovery range from different processed samples. Determine SPN binding in different processed samples. Determine SPN binding specificity compared to ELISA assay. |
| Challenging matrices | Salad dressing | Soy, milk and gluten | Determine allergen protein from high fat, high acid sample. Test allergens listed and spike with known amount of allergen proteins, test immediately and after 3, 6 and 12 hours. Dilute samples to determine minimum and maximum protein recovery and detection capabilities. | Determination of allergen recovery range from high fat high acid sample. Determine SPN binding in in high fat high acid samples. Determine SPN binding specificity compared to ELISA assay. |
| Challenging matrices | Soy, fish and tariakyi sauce | Gluten and soy | Fermented food is considered difficult for protein extraction, we will test different sauces and compare to gluten free sauces. Dilute samples to determine minimum and maximum protein recovery and detection capabilities. | Determination of allergen recovery from fermented foods. Determine SPN binding in fermented foods. Determine SPN binding specificity compared to ELISA assay. |
| Challenging matrices | chocolate | Milk, peanut and cashew | Chocolate is considered a difficult food matrix for protein extraction due to the high content of tannins and other phenolic compounds that have a high binding affinity to proteins. | Determination of allergen recovery from food samples with high tannins and phenolic compounds. Determine SPN binding in chocolate based foods. |

TABLE 7-continued

Examples of food matrices

| Food Category | Examples of food tested | Allergens tested | Testing procedure | Deliverable |
| --- | --- | --- | --- | --- |
| | | | We will test the allergen recovery and compare milk and dark chocolate with/without peanuts/cashews. Dilute samples to determine minimum and maximum protein recovery and detection capabilities. | Determine SPN binding specificity compared to ELISA assay. |

Total protein from the listed food matrices will be extracted using different extraction buffers and total protein recovery will be tested using BCA protein assay kit (Thermo Scientific Pierce) and specific allergen recovery in different extraction buffers will be tested by ELISA assay kits (Elution Technologies Neogen and BioCheck) and compared to SPN binding (GloMax Detection System).

Example 8: Establishing and Optimizing Device Sampling Mechanism

Tests and optimization processes are established to achieve this objective to be protein extraction from high fat, and highly processed foods and decreasing the protein extraction time to under one minute.

Some food matrices containing high fat, acid or food coloring will be challenging for protein extraction; however, some chemicals are introduced so that will reduce non-specific binding (gelatin, BSA or skim milk) to the extraction buffer, decrease pore size in filters to remove larger molecules, increase detergent concentrations to overcome fatty content, increase sample to buffer ratio, etc. Decreasing the processing time might trigger more debris and protein complexes that might clog the filter and interfere with the detection mechanism. The digestion process is then optimized by increasing the rpm of the blender, increasing/decreasing pH of buffer as well as increasing the pore size in the filters. These changes will be done in the context of time considerations.

A table is created, comparing the total protein, specific allergen recovery (all 8 allergens) before and after processing in 3 different buffers compared to 3 different extraction buffers from commercial ELISA assays. The table will display an average recovery rate from at least 20 different food matrices (see Table 7). Based on the comparison table determine the extraction buffer with the highest total yield and specific recovery rate for further analysis and optimization.

Example 9: Selection and Optimization of Detection Aptamers for 8 Food Allergens To combine the signal transduction capability of MB and the protein-binding specificity of aptamers to create signaling polynucleotides (SPNs) that will bind to food allergens and signal of their presence, an in-vitro screening and selection of the food allergen aptamers will be done using SELEX as described in the application. The dissociation constant of 5 different sequences for each of the aptamers is tested. These 5 sequences will be chosen by both positive selection for the specific allergen protein and negative selection to the other 7 allergen proteins. The protein we will select with will include both folded and denatured protein. The sequences remaining after 10 rounds of selection will be further analyzed to determine the Kd affinities, signal-to-background, LOD, targeting and EC50/IC50. The top 5 sequences with Kd in the low nanomolar range (<300 nM) will be chosen for further analysis. The Kd will be assessed preferably by ForteBio but if appropriate other means including Dot Blot, Gel-shift assay, or Flow Cytometry are tested. The lower the Kd the higher the binding affinity this will increase sensitivity.

The SELEX selection process is done on crude protein samples purchased from the ELISA assay manufactures and approved by AOAC to serve as a standard for the specific allergen. The protein is a mixture of pure, processed and denatured allergen protein. This will enable selecting an aptamer that will bind the protein in all of its different forms. The aptamer will undergo negative selection for any of the other 7 allergens to increase the selectivity.

Once specific aptamer sequences are selected for each of the major 8 food allergen, the sequence of the aptamer will be incorporated into a MB structure. The aptamer sequence is designed as the loop sequence of the MB and the result will be an SPN molecule. In the presence of protein, there will be a fluorescence signal change in the SPN that depends on the protein concentration.

To assess and optimize the binding sensitivity and specificity of the different SPN their binding affinity will be tested on different food matrices (see Table 7) and compared to ELISA kit testing. The $MgCl_2$:KCl ratio in the buffer is changed and optimize the binding affinity and selectivity of the selected aptamers. Tm in the presence of $MgCl_2$ is higher, pushing towards the stem-loop structure, while adding NaCl or KCl pushes towards the active SPN protein binding. non-manipulating aptamers are also tested and compared with manipulated aptamers post selection. If the binding affinity is decreased, the length of the flanked sequences are changed, adding chemical modification or mismatches to the double helix to increase/decrease the non-binding structure. If these modifications are unsuccessful, a different sequence is chosed to manipulate from the sequences selected.

Through this process, all the sequences for all 8 allergens are selected (i.e. wheat, egg, milk, peanuts, tree-nuts, fish, shell-fish and soy), and the top 5 sequences will be rated based on their Kd values, which are manipulated as SPNs for each of the 8 allergens. These sequences will have binding affinity that is not significantly higher than the non-manipulated sequences.

Example 10: Establishing and Optimizing Device-Sampling Mechanism

The sampling mechanism is further optimized to ensure reliable, and reproducible food sampling, with high accuracy between different food matrices.

Sampling Process

The analysis of food sample begins by inserting the sample collection probe into a target sample. During the sample collection, a drill bit residing inside the needle is spun by a motor causing it to act as a screwpump (also known as an Archimedes screw). The "chip-clearing" action of the drill bit serves to capture pieces of the target sample and convey them from the collection needle in to the middle of the mixing chamber. The mechanism will be optimized to sample a specific amount of food each round. The coring abilities will be tested over a large range of food textures and optimized.

Digestion and Protein Extraction

Once a piece of the target sample is collected and delivered to the mixing chamber, the syringe pump plunger is depressed. This forces the digestion buffer into the mixing chamber. This forces the digestion buffer through one-way valve 1422 and into the mixing chamber. The one-way valve 1424 is oriented to prevent flow backwards into the detection chamber; its function will be described in step 3. Once the digestion buffer is delivered to the mixing chamber, a motor spins the mixing spindle following a prescribed time and speed profile to properly homogenize the sample, freeing the constituent proteins of interest. The driving motor is attached at the motor attachment point, and it is the same motor that spins the drill bit screwpump during the first step.

The RPM, torque as well as the blade placement of the blending unit will be optimized to ensure full homogenization of different food textures. The ratio between the extraction buffer and food sample will be challenged, extracting high levels of protein without diluting the food sample.

Filtration

After the sample is digested and homogenized, it must be passed through the purification filter into the detection chamber by drawing the syringe pump plunger that was previously depressed. This time, however, one-way valve 1424 serves to block material from exiting the mixing chamber backwards, and one-way valve 1422 opens to provide negative pressure across the purification filter, thereby drawing the sample into the detection chamber. A hydrophobic filter is placed at the exit of the detection chamber to allow any interfering gas to pass through while preventing the sample of interest from escaping. Once the sample is in the detection chamber, the analysis unit can perform interrogation of the sample and report the measurement to the user.

The filtration unit could not only eliminate debris but also concentrate the allergen proteins. Most food allergens are smaller the 70 KDa. Using a 100 KDa threshold membrane we will significantly concentrate the allergen proteins in our sample yet would require immense pressure (100 psi). Filters with different pore size (0.2, 0.1, 0.03 and 0.01 um) will be tested and compared to reverse osmosis membranes.

The unique configuration of a circulating loop with strategically placed filters and one-way valves, means that the syringe pump plunger can be drawn and depressed through several cycles to ensure that enough of the sample material is delivered to the detection chamber. It also means that, aside from the mixing motor, only 1 additional precision stepper/control motor is required to sample transport. Otherwise one motor would be required to deliver the digestion buffer, and another would be required to draw the sample into the detection chamber. The benefit of this is significant, since each additional motor would add size, weight, cost, and power consumption to the overall device.

Once the sample is collected in the first step, all subsequent steps are designed to be automated under the control of the analysis unit, so that no further user interaction is required.

Through these optimizations, a food sampling mechanism that is a single step, measured and reproducible mechanism is established. The protein extraction will be no more than 1 minute.

Example 11: Design of the Signaling Polynucleotides

The following method is used for engineering signaling polynucleotides.

A polynucleotide is first selected for design. The 3-dimensional folding of the selected polynucleotide is then performed using the mFOLD software (Michael Zuker & Nick Markham, © Rensselaer Polytechnic Institute, hosted by The RNA Institute, College of Arts and Sciences, State University of New York at Albany, and supported by the SUNY Albany Research IT Group).

A nucleotide sequence between 4 and 18 or between 4-12 is then added to the 3' of the polynucleotide which underwent initial folding analysis. This added nucleotide sequence represents, in part or in whole a sequence which is the reverse complement to the sequence at the 5' end of the initial polynucleotide.

The 3-dimensional structures of the resulting signaling polynucleotide comprising the first polynucleotide and the added polynucleotide are then analyzed through m-FOLD. Based on the mFOLD analysis, which can include selection of thermodynamic parameters or structural parameters, selected candidates are chosen. In some embodiments, the complete polynucleotide sequences chosen for further testing are the polynucleotide sequences which form a closed stem-loop structure attaching the 5'- and 3' ends to each other and which have the lowest Δ G.

Example 12: Test of Protein Extraction and Allergen Recovery Using Different Extraction Buffers As proposed in Example 7, different digestion/extraction buffers with different chemical components were tested and compared in order to find the proprietary extraction buffer for allergen detection. This universal extraction buffer can maximize protein extraction and allergen retrieval. The universal extraction buffer will be applicable to any allergen and to all foods (e.g. pre-processed or post-processed). Additionally, the universal extraction buffer can improve signaling polynucleotides (SPNs) binding affinity, minimize non-specific binding and increase signal to noise ratio.

Serial experiments were designed to compare different extraction buffers for total protein extraction and specific allergen recovery. Tris based buffers, PBS based buffers and Neogen ELISA extraction buffer were tested and compared with each other. The buffers used in the experiments were listed in Table 8. Different modifications to Tris based and PBS based buffers were performed to optimize buffer conditions in order to achieve maximal protein recovery and SPN detection capacities.

TABLE 8

Different buffers tested and compared
for total protein and allergen recovery

| Tris based buffer | PBS based buffer | Neogen ELISA buffer |
|---|---|---|
| Tris PH 7.4 | PBS 0.2 mol NaCl | |
| Tris PH 7.4, EDTA 5 mM | PBS 0.2 mol NaCl, betamercaptoethanol | |
| Tris PH 7.4, 20% EtOH | PBS 0.2 mol NaCl, 40% EtOH | |
| Tris PH 7.4, EDTA 5 mM, 20% EtOH | PBS 0.2 mol NaCl, 20% EtOH | |
| Tris PH 8.0 | PBS 0.2 mol NaCl, 10% EtOH | |
| Tris PH 8.0, EDTA 5 mM | PBS 1 mol NaCl | |
| Tris PH 8.0, 20% EtOH | PBS 1 mol NaCl, betamercaptoethanol | |
| Tris PH 8.0, EDTA 5 mM, 20% EtOH | | |

Experimental Set-Up:

allergen (e.g. gluten) at different concentrations was spiked to either prebaked or postbaked cake. Regular bread, gluten free (GF) bread and gluten free cake were also used as food sources to test allergen recovery with different testing extraction buffers. Different extraction buffers were add to food samples, (the formulation of the buffer was as stated in the table above). Different sample to buffer ratios were tested starting at a 1:20 (0.5 g sample and 10 ml buffer), 1:10 (0.5 gr sample and 5 ml buffer), 1:5 (0.5 gr sample and 2.5 buffer). We also tried increasing the sample size and keeping the buffer stable at 2.5 ml. Food samples were 0.5, 1, 1.5, 2 and 2.5 gr in 2.5 ml buffer. The food sample with buffer were homogenized using a gentleMAC or hand held homogenizer. The homogenized solution was either left at room temp for 15 min to let the sediment settle or centrifuged for 5 min at 5000 rpm. The top aqueous solution was collected and transferred to a new tube for further analysis. Total protein extraction was tested using the BCA pierce kit or by testing total Nitrogen (test strips). Specific allergen recovery rates were tested using the commercially available ELISA kits. For egg and peanut samples the specific SPNs were tested as well.

Figure 15:
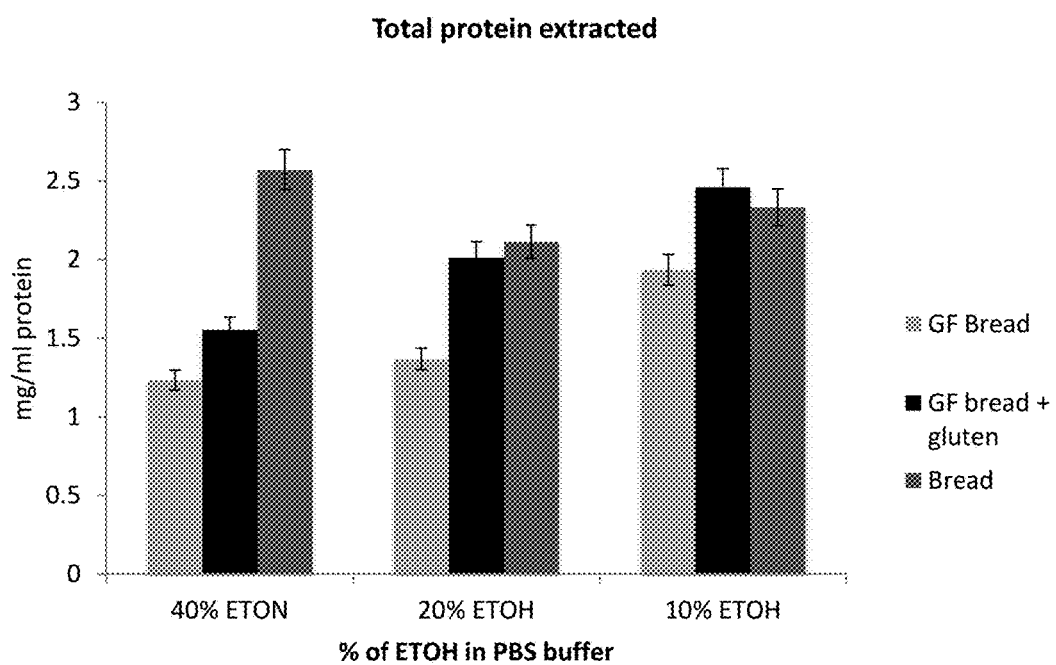
FIG. 15 is a histogram showing total protein extracted in PBS based bufffers containing 10%, 20% and 40% ethanol (EtOH). GF means gluten free.

The comparison indicated that in PBS based buffers, addition of betamercaptoethanol did not increase total protein extraction, but addition of 10% EtOH increased total protein extraction as shown in FIG. 15.

Figure 16:
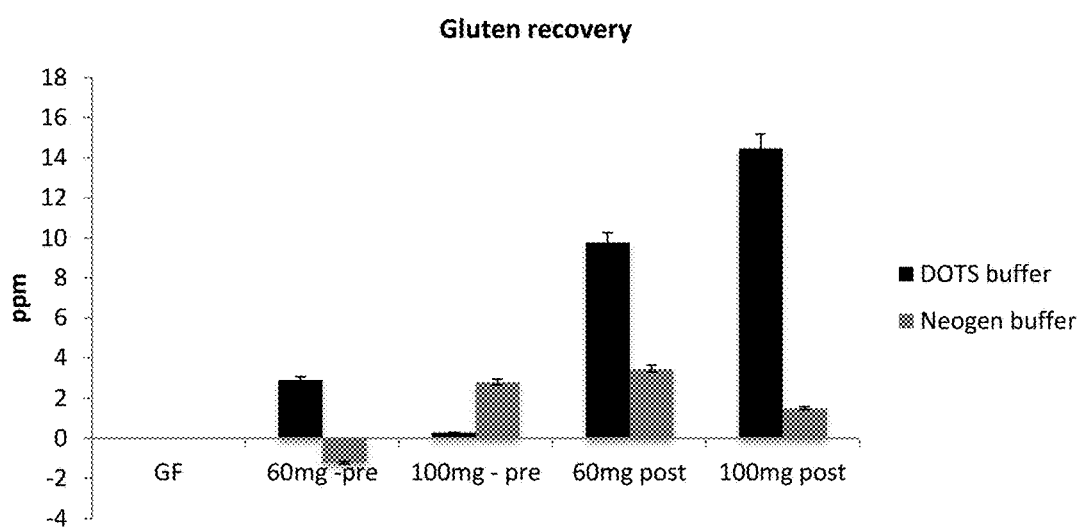
FIG. 16 is a histogram showing gluten recovery in Tris based buffer (DOTS buffer) containing Tris base pH8.0, 5 mMEDTA and 20% ethanol and Neogen buffer.

Tris based buffers with different pH values and additives were compared to Neogen gluten extraction buffer. The results showed that Tris buffer with pH8.0, 5 mM EDTA and 20% EtOH (designated as DOTS buffer in FIG. 16) resulted in better gluten recovery as compared to Neogen gluten extraction buffer. Furthermore, Gluten retrieval from post-bake increased 200% with Tris buffer (pH8.0, 5 mM EDTA and 20% EtOH, as DOTS buffer) but no retrieval with Neogen buffer (FIG. 16). The comparison further suggested that the gluten retrieved from prebaked goods after dilution of 1:50 with either buffers is too diluted to be detected. It is also shown that 100 mM Tris buffer with pH8.0 was better than that with pH7.4 and that addition of EDTA (5 mM) and 10% EtOH improved total protein extraction.

To further optimize the extraction buffer, Tris based buffers were further modified with different salts and additives as listed in Table 5). The components in each modified Tris pH8.0 based buffer are indicated in Table 9.

TABLE 9

Modified Tris-based buffers

| | Buffer A | Buffer B | Buffer C | Buffer D | Buffer E | Buffer F |
|---|---|---|---|---|---|---|
| Tris pH 8.0 | + | + | + | + | + | + |
| SDS 0.1% | + | + | + | + | + | − |
| DETA 5 mM | + | + | + | + | − | + |
| Gelatin 1% | + | + | + | − | − | + |
| NP-40 1% | + | + | + | + | + | + |
| 0.5% Deoxycholate | + | + | − | + | + | + |
| NaCl 150 mM | + | + | + | + | + | + |
| EtOH | − | + | − | − | − | − |

Figure 5:
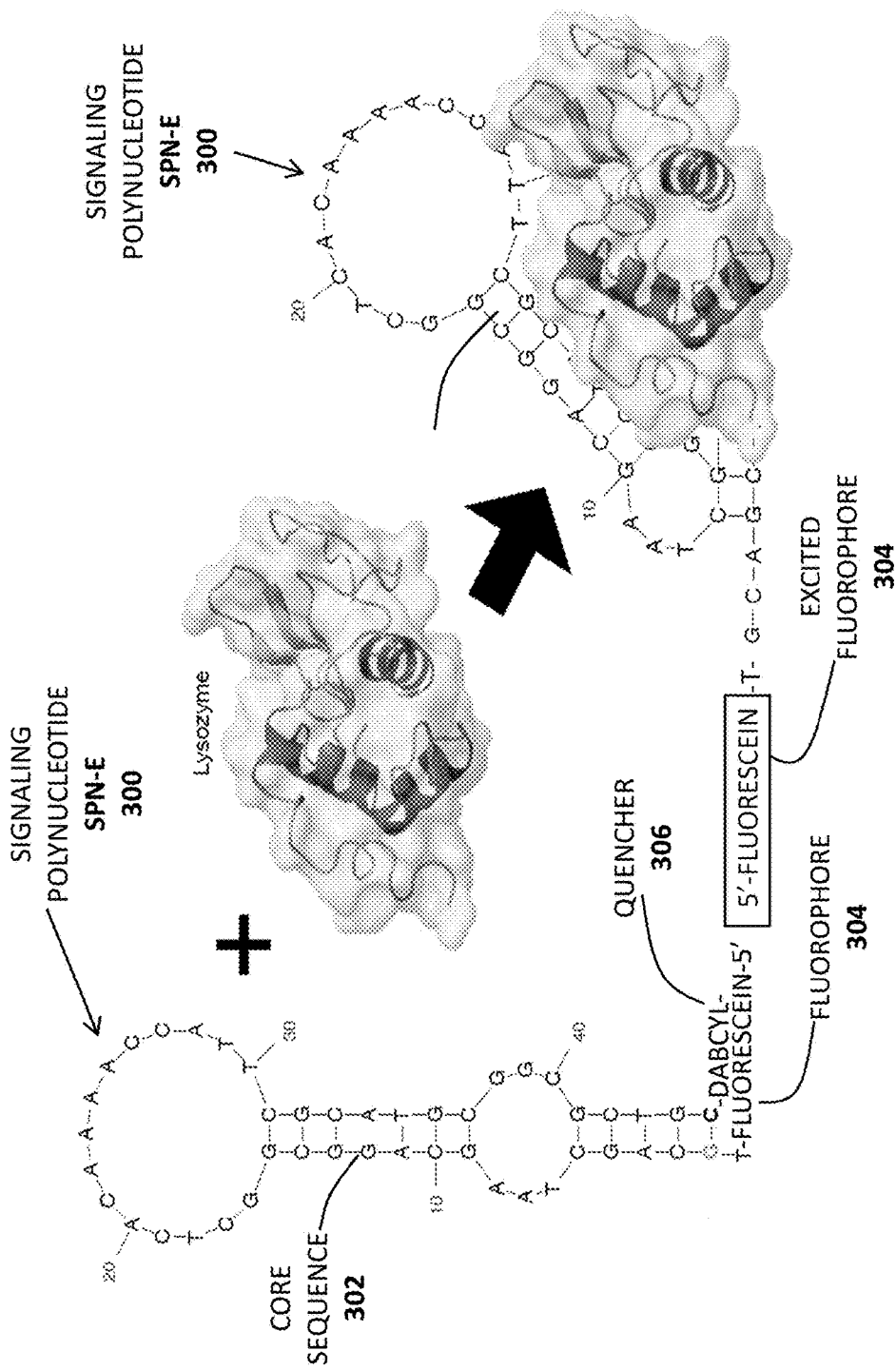
FIG. 5 shows a reaction between a detection molecule represented by a hairpin-type signaling polynucleotide SPN-E 300 with its target molecule lysozyme. Also shown are the aptamer core sequence 302, the fluorophore 304 and the quencher 306.
Figure 17A:
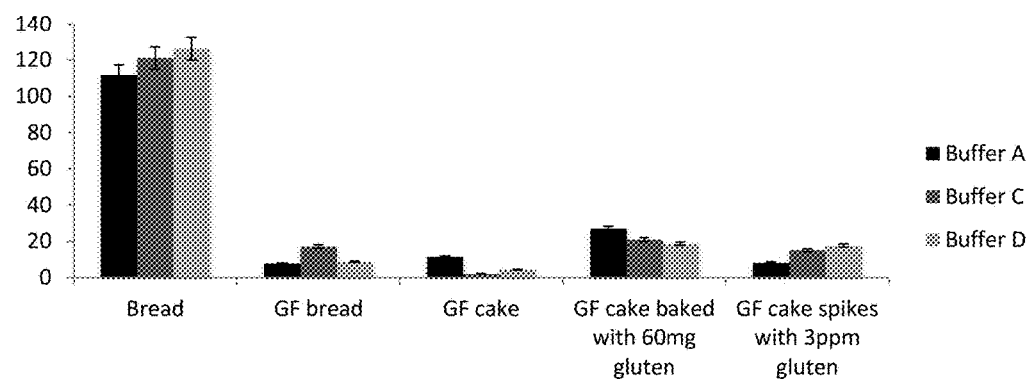
FIG. 17A shows gluten recovery (ppm) in modified Tris based buffers A, C and D
Figure 17B:
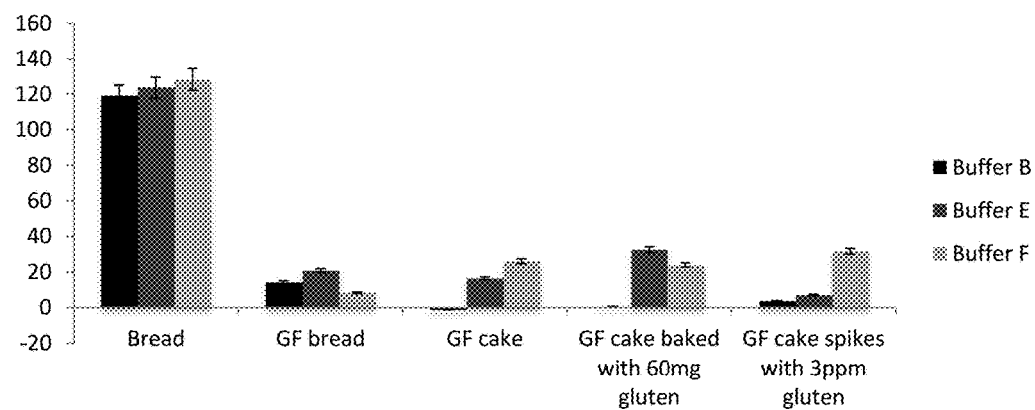
FIG. 17B shows gluten recovery (ppm) in modified Tris based buffers B, E and F.
Figure 18A:
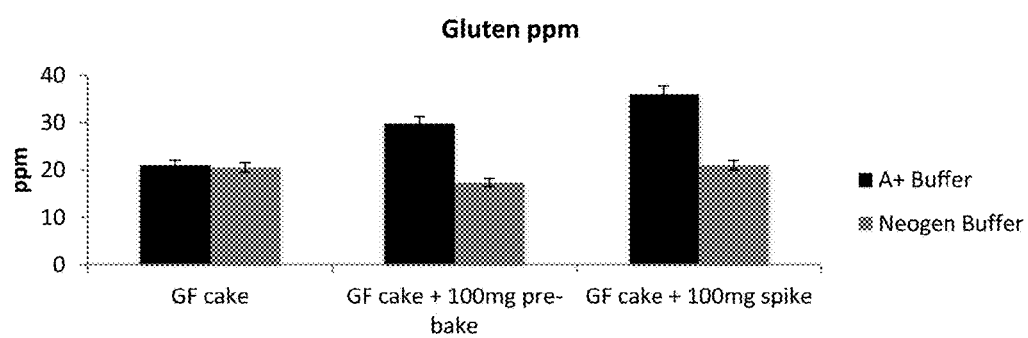
FIG. 18A and FIG. 18B show gluten recovery in Tris based buffer A+ and Neogen extraction buffer.
Figure 18B:
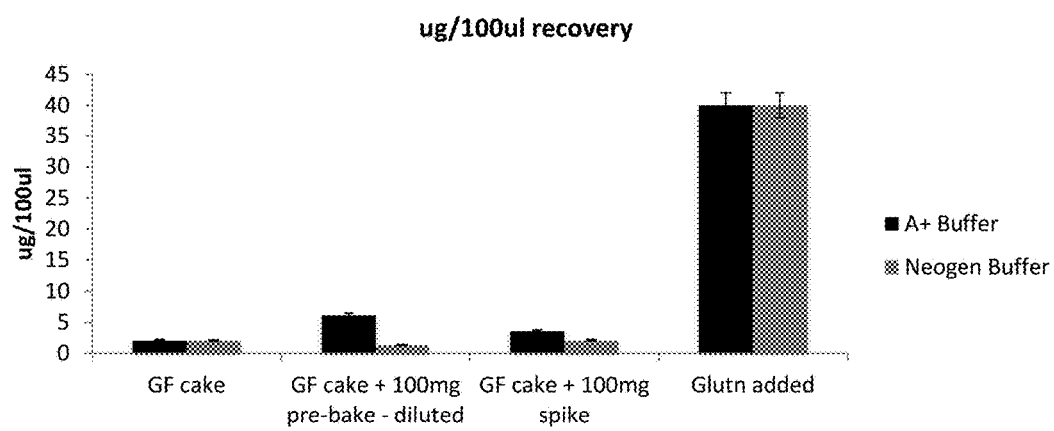
Figure 19:
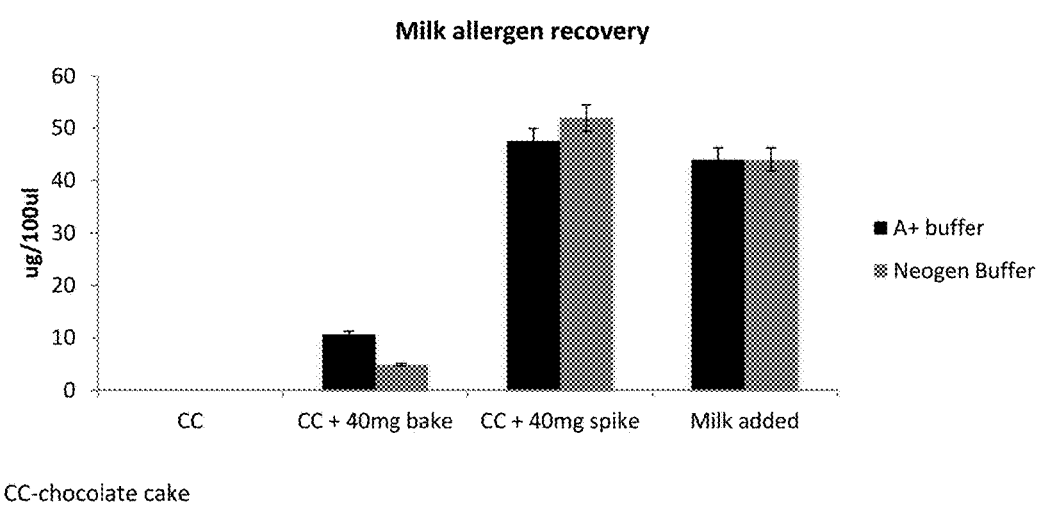
FIG. 19 shows milk allergen recovery in Tris based buffer A+ and Neogen extraction buffer. Samples were diluted 1:10 for testing. It shows 10% milk allergen recovery for spiking pre-baking and 100% recovery for spiking post-baking in Tris based buffer A+.

FIG. 17 shows gluten recovery using buffers A to F. Buffer A was then further modified to decrease the concentration of gelatin to 0.5%. Such decrease can allow for easier filtration. The modified buffer is designated as Buffer A+. In a test, pre and post baking cake were spiked with 40 μg/100 μl gluten. The baking goods were extracted with either buffer A+ or Neogen extraction buffer and extraction samples were diluted at a ratio of 1:10, 1:100 or 1:1000 dependent on the sample in order to be in the linear range of the ELISA kit for detection. FIGS. 18 (A&B) showed that only buffer A+ can recover about 7-10% of spiked gluten. FIG. 5 showed the recovery percentage of milk allergen using buffer A+. 10% and 100% of milk allergen spiked pre-baking and post-baking were recovered using buffer A+, respectively. Neogen ELISA extraction buffer generated similar recovery percentages as buffer A+(FIG. 19).

Figure 20A:
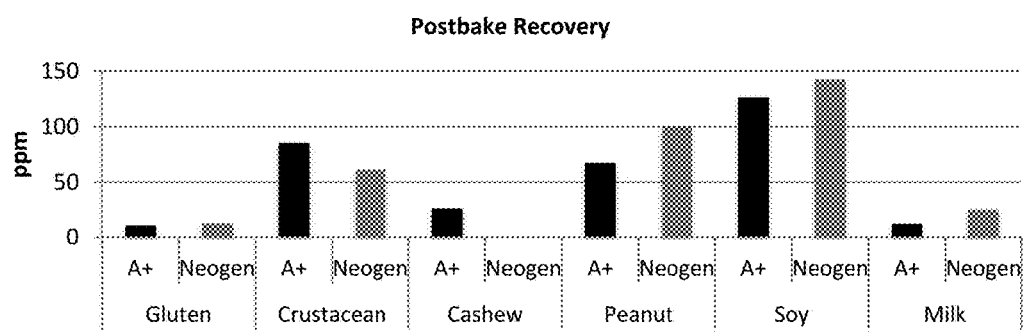
FIG. 20A shows postbake allergen recovery in Tris based buffer A+ and Neogen buffer.
Figure 20B:
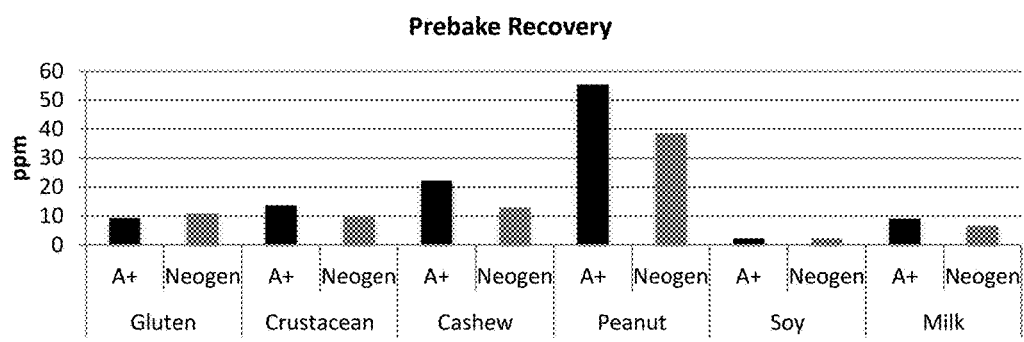
FIG. 20B shows prebake allergen recovery in Tris based buffer A+ and Neogen buffer.

Buffer A+ extraction capacities with other common allergens, such as gluten, Crustacean, cashew, peanut, soy and milk were tested and compared with Neogen ELISA buffer. The Results are shown in FIGS. 20 (A&B).

In another set of tests, PBS based buffers were further modified with different salts an additives listed in Table 5. The modified PBS based buffers were designated as P+ buffer or P− buffer and the components in P+ and P− buffers are listed in Table 10.

TABLE 10

PBS based buffers: P+ buffer and P− buffer

| | P+ buffer | P− buffer |
|---|---|---|
| PBS pH 8.0 | + | + |
| SDS 0.1% | + | + |
| MgCl$_2$ | + | + |
| Gelatin 0.1% | + | − |
| NP-40 1% | + | + |
| 0.5% Deoxycholate | + | + |
| NaCl 150 mM | + | + |

Figure 21A:
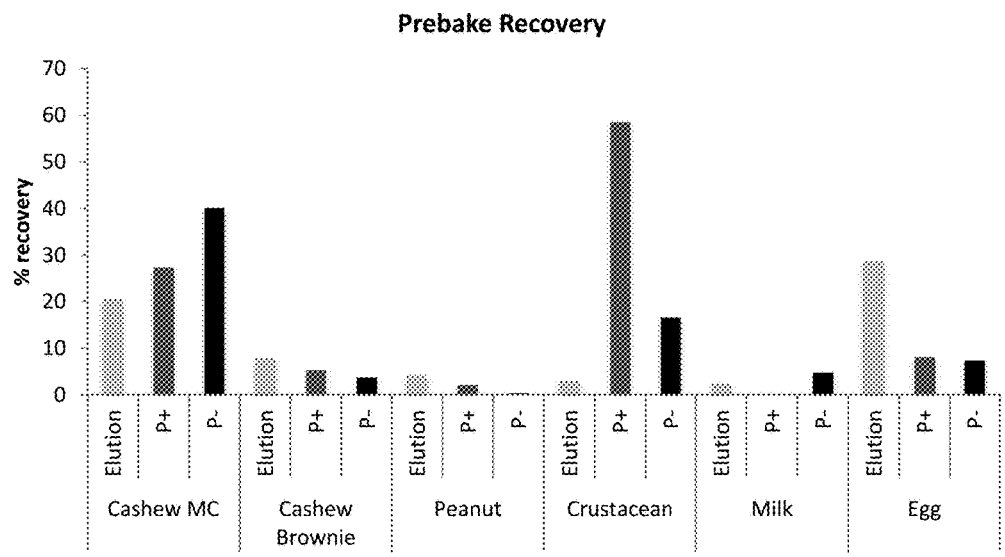
FIG. 21A shows prebake allergen recovery in PBS based buffers: P+ buffer and P− buffer.
Figure 21B:
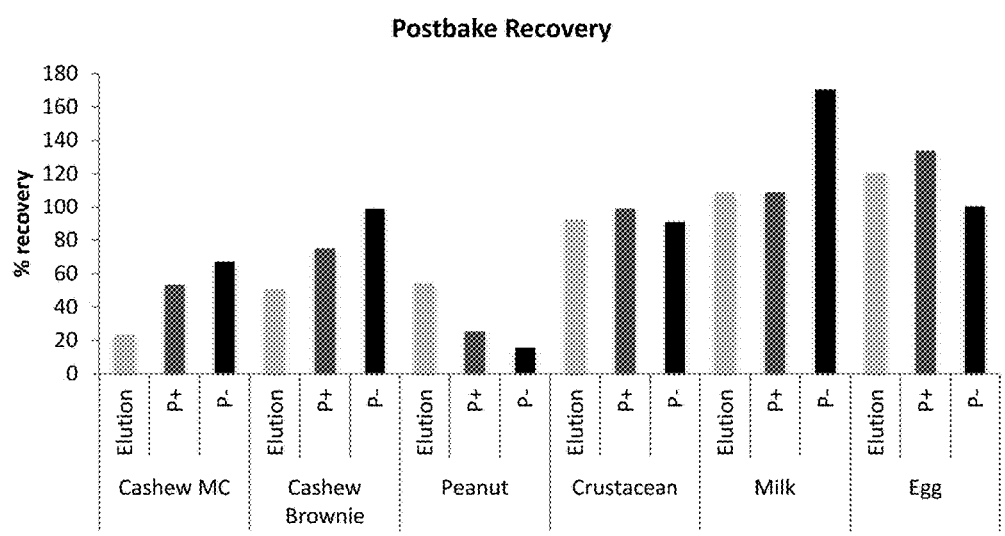
FIG. 21B shows postbake allergen recovery in PBS based buffers: P+ buffer and P− buffer.

Allergen recovery was tested with P+ buffer and P− buffer in both pre-baked and postbaked goods. FIGS. 21A and 21B showed the allergen recovery rates in pre-baked goods and postbaked goods, respectively.

PBS buffer was further modified to increase the allergen recovery percentage. The modification includes lowering the concentration of MgCl and adding another salt KCl. The components of modified PBS based buffer, which is designated as K buffer, are listed in Table 11.

TABLE 11

| PBS based buffer: K buffer | |
| --- | --- |
| | K buffer |
| 0.1M PBS pH 8.0 | + |
| SDS 0.1% | + |
| MgCl$_2$ 10 mM | + |
| Gelatin 0.1% | + |
| NP-40 1% | + |
| 0.5% Deoxycholate | + |
| NaCl 100 mM | + |
| KCl 50 mM | + |

Tested results suggest that K buffer can significantly increase the allergen recovery rates and is applicable to any allergen tested and to all food sources (e.g. prebaked and postbaked) (See Table 12).

TABLE 12

K buffer recovery rates
Allergen Recovery

| | Waffle | | | | Mug cake | | | |
| --- | --- | --- | --- | --- | --- | --- | --- | --- |
| | K buffer | | Elution | | K buffer | | Elution | |
| | Pre | Post | Pre | Post | Pre | Post | Pre | Post |
| Gluten | 42% | 268% | 27% | 324% | | | | |
| Egg White | 7% | 114% | 10% | 149% | | | | |
| Milk | 9% | 113% | 8% | 73% | | | | |
| Crustacean | 11% | 107% | 8% | 42% | 20% | 76% | 20% | 47% |
| Cashew | 23% | 62% | 22% | 52% | 48% | 68% | 64% | 79% |
| Soy | 2% | 231% | 1% | 28% | 0% | 4% | 0% | 3% |
| Fish | 26% | 66% | 33% | 78% | 48% | 68% | 64% | 79% |
| Peanut | 11% | 35% | 22% | 40% | 11% | 18% | 29% | 56% |

Figure 22A:
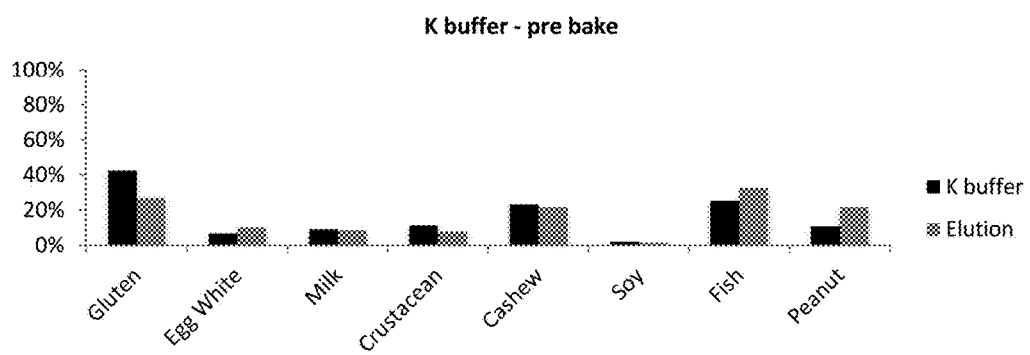
FIG. 22A and FIG. 22B show allergen recovery rates in PBS based K buffer compared to those in Elution ELISA kits.
Figure 22B:
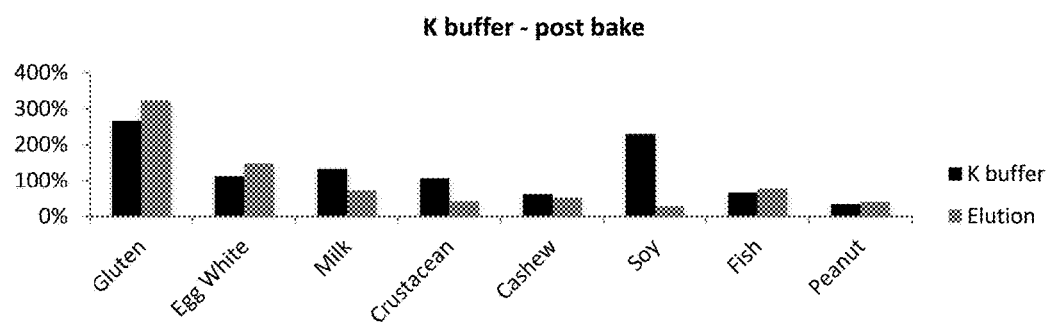

As compared to Elution ELISA buffer (Elution Technologies Neogen and BioCheck), K buffer has comparable extraction capacity as Elution buffer (FIGS. 22A&B).

Figure 23:
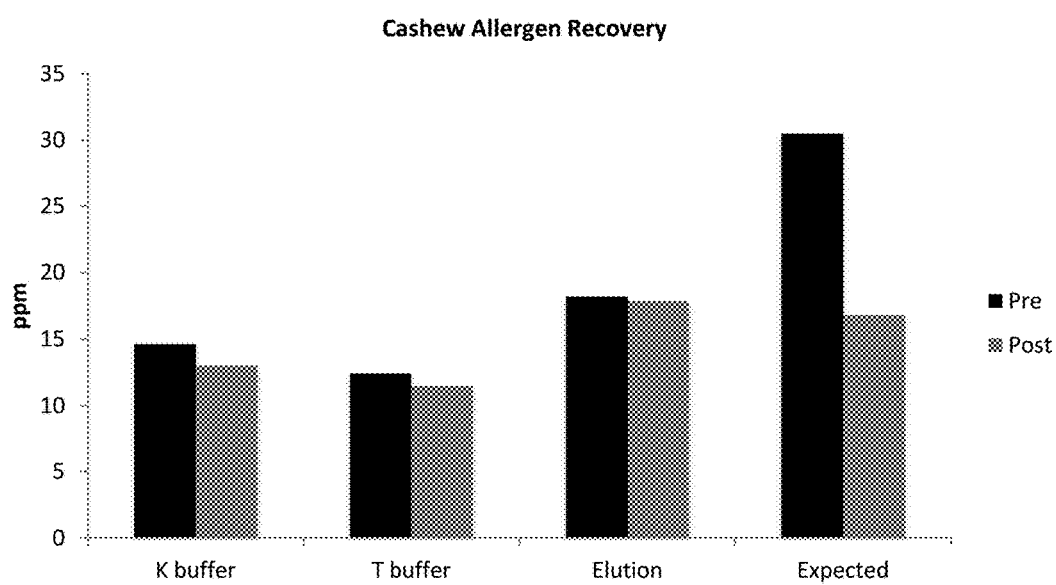
FIG. 23 shows a comparison of cashew allergen recovery between Tris based T buffer and PBS based K buffer. In this experiment, vanilla pudding was used as a food matrix.

Given the fact that a Tris based buffer is usually preferred to in oligonucleotide binding experiments, the PBS component in K buffer is replaced with Tris pH 8.0 to generate T buffer. The components in T buffer are listed in Table 13. The influence of Tris base on allergen recovery as well as SPN binding was tested. FIG. 23 compared cashew allergen recovery in K buffer, T buffer and Elution ELISA buffer.

TABLE 13

| Tris based buffer: T buffer | |
| --- | --- |
| | T buffer |
| Tris pH 8.0 | + |
| SDS 0.1% | + |
| MgCl$_2$ 10 mM | + |
| Gelatin 0.1% | + |
| NP-40 1% | + |
| 0.5% Deoxycholate | + |
| NaCl 100 mM | + |
| KCl 50 mM | + |

Example 13: Test of SPN Binding Affinity Using Different Extraction Buffers

After testing allergen recovery rates of different extraction buffers, signal polynucleotide (SPN) binding affinity to allergen retrieved with different buffers were tested and compared in order to develop a universal extraction buffer for SPN mediated allergen detection.

A set of binding assays were performed using lysozyme SPNs (MB4, MB5 and MB6). Experimental procedures: Food samples were homogenized as stated above—generally 2.5 ml buffer was added to 0.5 food sample. The samples were homogenized and centrifuged. 25 ul of the sample was added to a 96 flat bottom well plate. The specific SPN was resuspended to a 100 uM concentration and 25 ul of the SPN was added to the plate—final concentration 50 uM. The samples were immediately read with the GloMax Promega plate reader using the blue laser. (detection was quantified as the intensity of FITC minus the background—buffer alone and non-spiked samples).

The sequences of Signal polynucleotide MB4, MB5 and MB6 are shown as below:

MB4:
(SEQ ID NO: 13)
5'Fluorescein-
TGCAGCTAAGCAGGCGGCTCACAAAACCATTCGCATGCGGCTGCA-
Dabcy1-3'

MB5:
(SEQ ID NO: 14)
5'Fluorescein-
TGCAGCTAAGCAGGCGGCTCACAAAACCATTCGCATGCGGCCTGCA-
Dabcy1-3'

MB6:
(SEQ ID NO: 15)
5'Fluorescein-
TGCAGCTAAGCAGGCGGCTCACAAAACCATTCGCATGCGGCGCTGCA-
Dabcy1-3'

Figure 24:
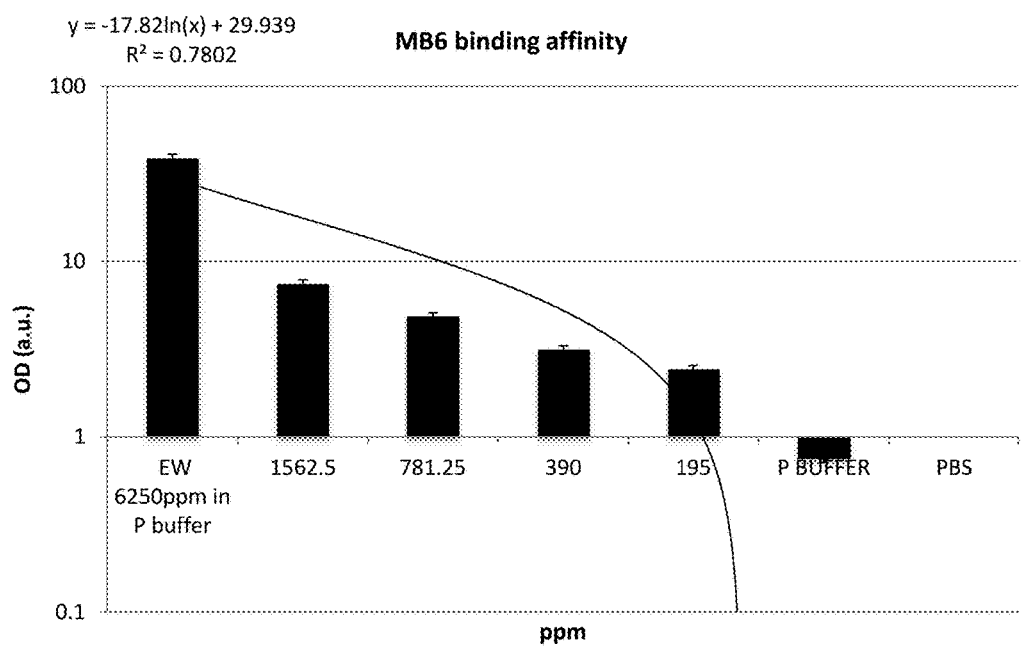
FIG. 24 shows MB6 binding affinity of egg white in PBS based P+ buffer, indicating that P+ buffer decreases binding affinity of SPNs to egg white.
Figure 25:
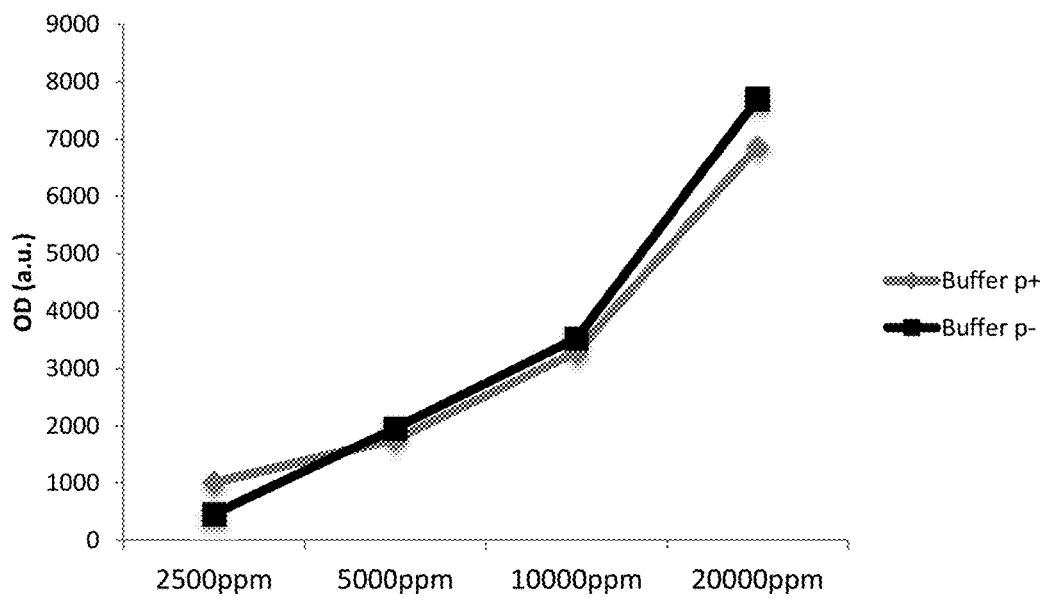
FIG. 25 is a plot of fluorescence detection of SPN MB-5 binding to egg white in P+ buffer and P− buffer, indicating that the effect of gelatin is insignificant for the binding of MB-5.
Figure 26A:
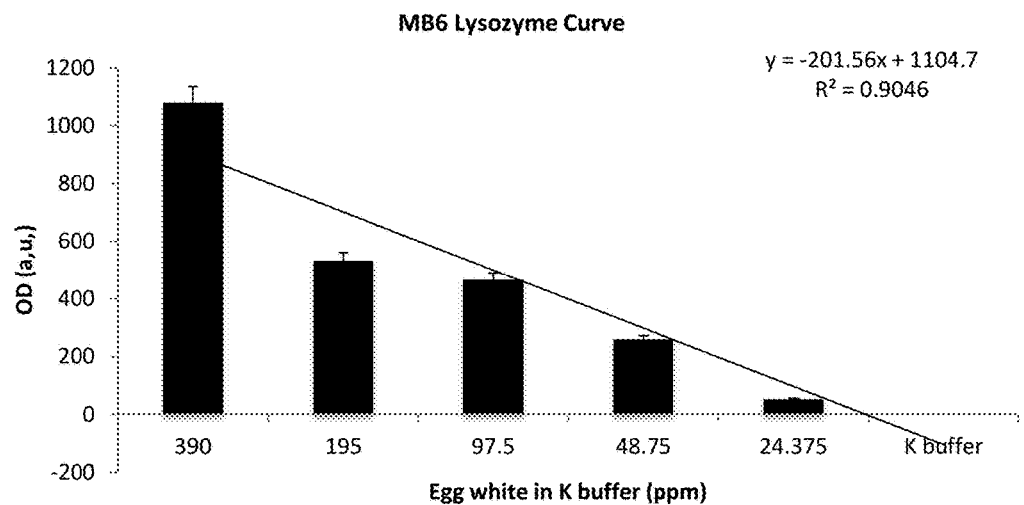
FIG. 26A and FIG. 26B show MB6 and MB4 binding affinity to egg white in K buffer, indicating that K buffer increases the binding affinity of SPNs
Figure 26B:
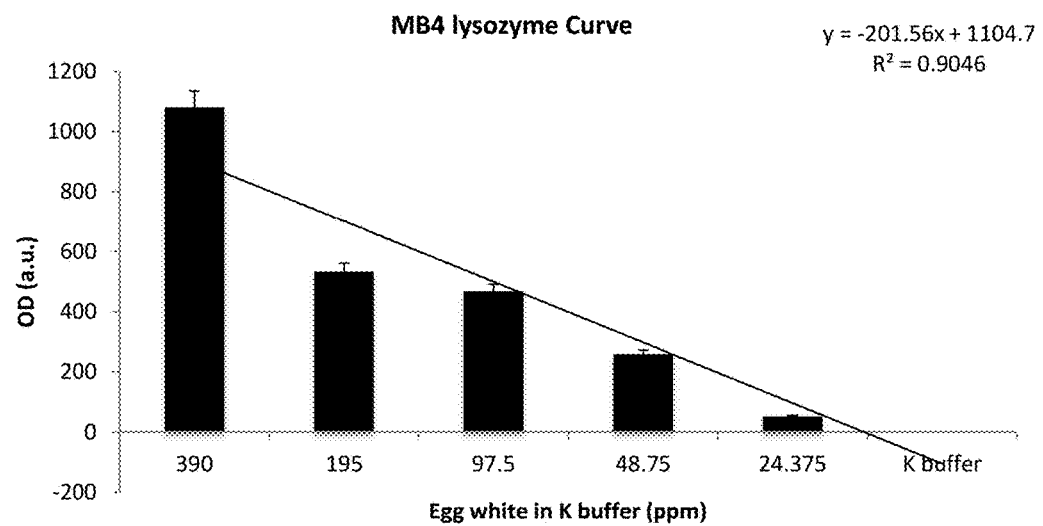
Figure 27A:
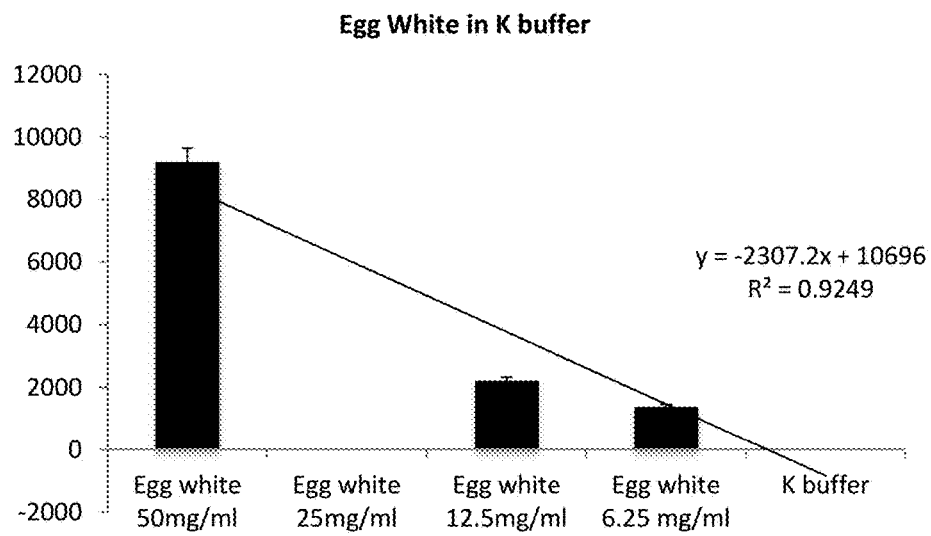
FIG. 27A shows MB5 binding affinity to pure egg white protein in PBS based K buffer.
Figure 27B:
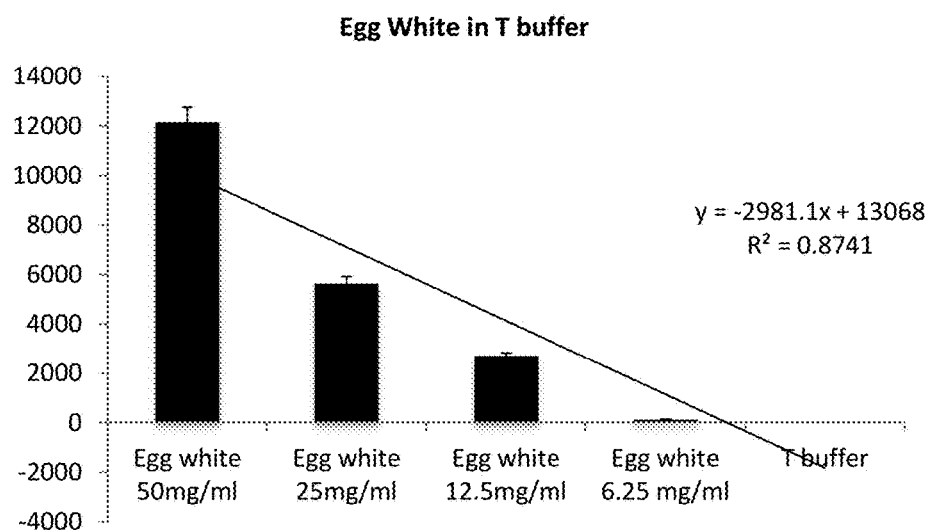
FIG. 27B shows MB5 binding affinity to pure egg white protein in Tris based T buffer.
Figure 28A:
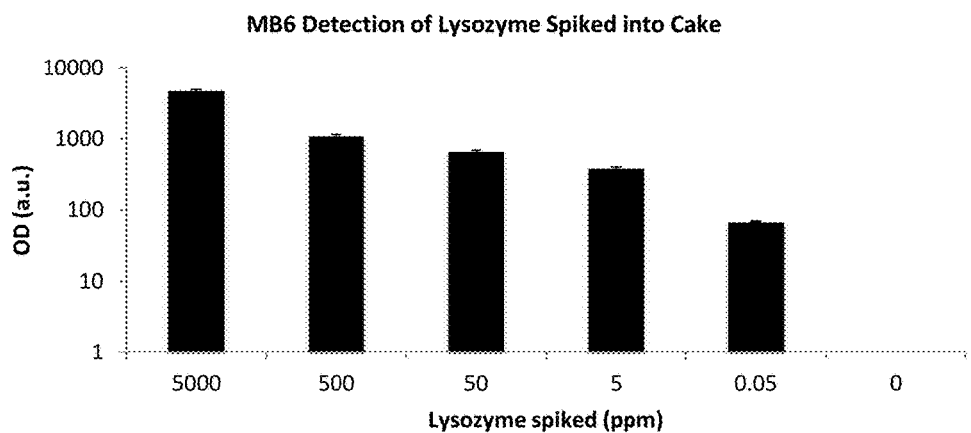
FIG. 28A is a bar chart showing MB6 detection of lysozyme spiked into chocolate cake.
Figure 28B:
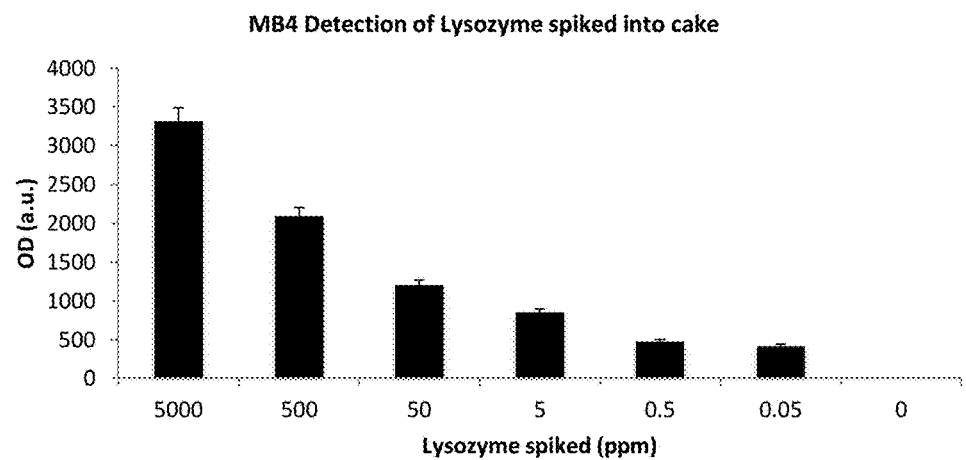
FIG. 28B is a bar chart showing MB4 detection of lysozyme spiked into chocolate cake.
Figure 29A:
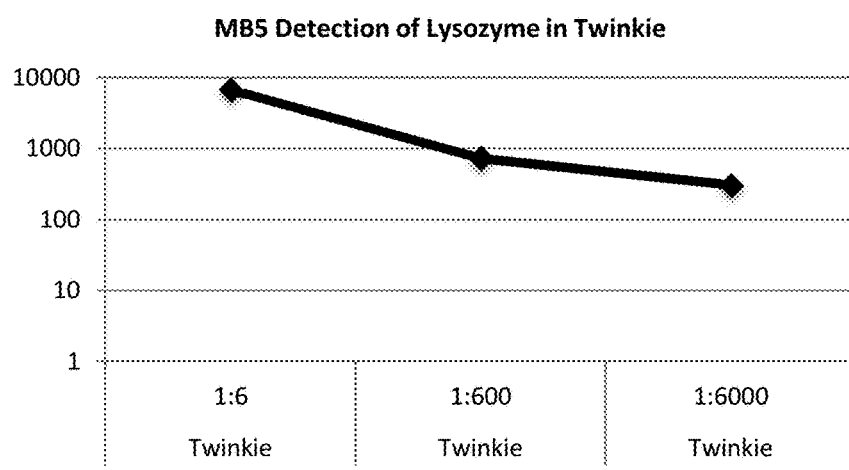
FIG. 29A is a bar chart showing MB6 detection of lysozyme in food containing eggs.
Figure 29B:
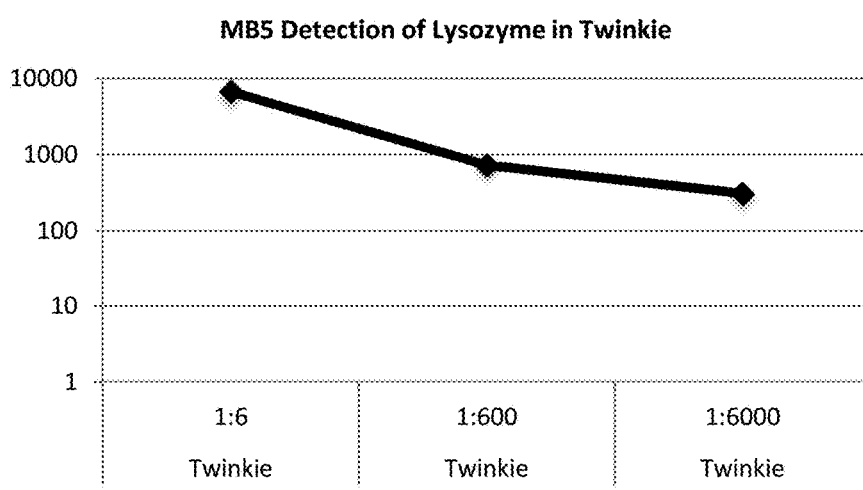
FIG. 29B is a bar chart showing MB4 detection of lysozyme in food containing eggs.

FIGS. 24 and 25 compare the effect of P+ buffer and P− buffer on MB6 binding affinity to egg whites. The similar binding curves of P+ buffer and P− buffer (FIG. 25) suggest that although the presence of gelatin in extraction buffer is very crucial for protein extraction, the effect of gelatin is insignificant for the binding of SPN. As shown in FIG. 10, P+ buffer decreases binding affinity of SPNs to egg white. However, the result suggests that K buffer can increase binding affinity of SPNs to egg white (FIG. 26). As compared to SPN binding affinity to pure egg white protein in T buffer, K buffer can enable a detection of lower lysozyme levels (FIG. 27). Similarly, T buffer allows a detection of lower levels of lysozyme spiked into chocolate cake (FIG. 28) and in food containing eggs such as Twinkies (TWINKIE®) (FIG. 29).

Binding affinity of Ara H1SPNs (MB7 and MB9) was also tested in K buffer. The Signal polynucleotides MB7 and MB9 were designed having the following sequences respectively.

MB7:
(SEQ ID NO: 16)
5'Fluorescein-
TCGCACATTCCGCTTCTACCGGGGGGGTCGAGCTGAGTGGATGCGAATCT
GTGGGTGGGCCGTAAGTCCGTGTGTGCGAA TGTGCGA Dabcy1-3'

MB9:
(SEQ ID NO: 17)
5'Fluorescein-
TCGCACATTCCGCTTCTACCGGGGGGGTCGAGCTGAGTGGATGCGAATCT
GTGGGTGGGCCGTAAGTCCGTGTGTGCGAA AATGTGCGA Dabcy1-3'

Figure 30A:
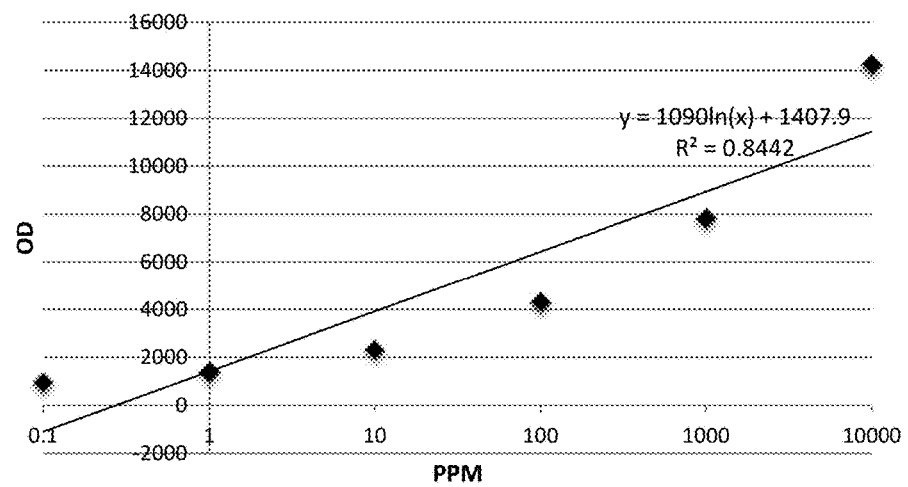
FIG. 30A is a plot of fluorescence detection of MB7 binding to pure peanut flour.
Figure 30B:
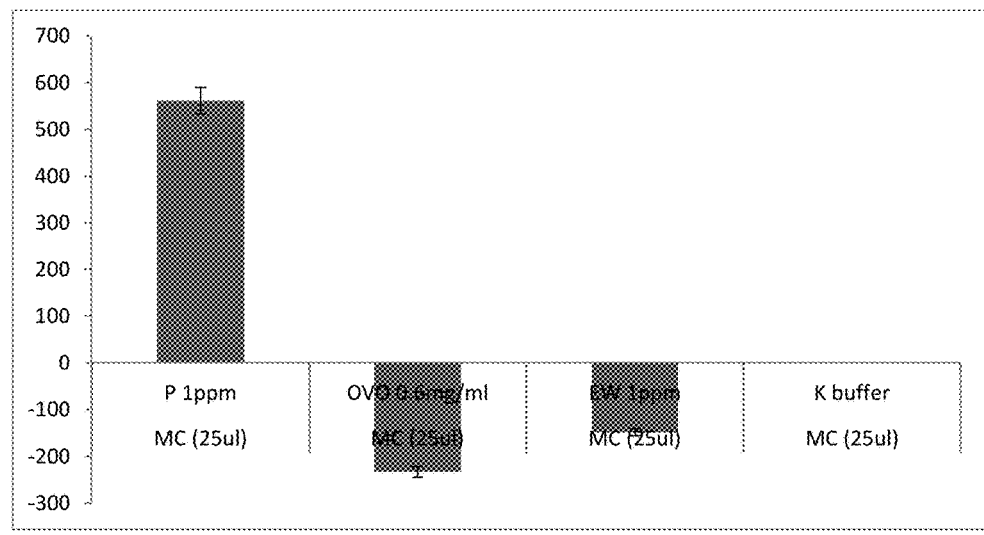
FIG. 30B shows that MB7 specifically binds peanut (P) flour at lower level of 1 ppm but not egg white (EW) or Ovomucoid (ovo) when spiked in a mug cake (MC) matrix.
Figure 31A:
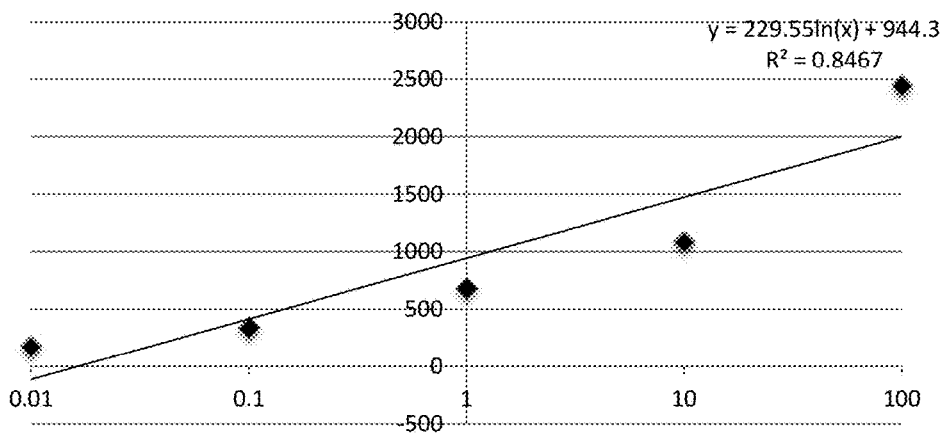
FIG. 31A is a plot of fluorescence detection of MB9 binding to pure peanut flour.
Figure 31B:
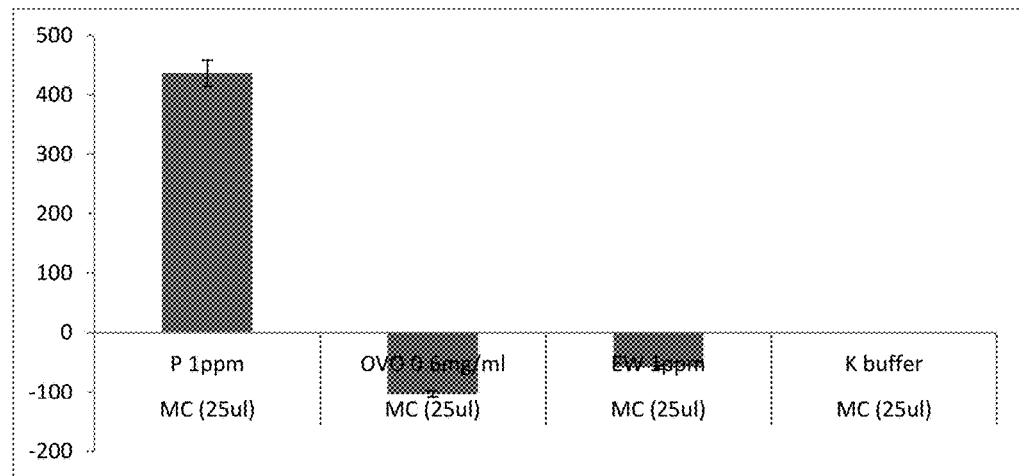
FIG. 31B shows that MB9 specifically binds peanut (P) flour at lower level of 1 ppm but not egg white (EW) or Ovomucoid (ovo) when spiked in a mug cake (MC) matrix.

Both MB7 and MB 9 can specifically bind to peanut allergen, but not to egg white and Ovomucoid (FIGS. 30A&B for MB7 and FIGS. 31A&B for MB9).

Figure 32A:
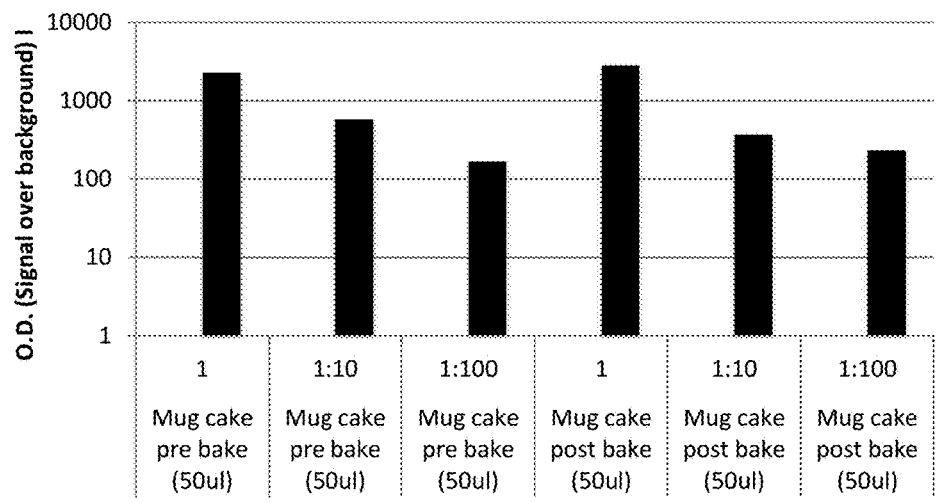
FIG. 32A shows MB7 detection of peanut at low ppm levels spiked into cake pre-baking and post-baking.
Figure 32B:
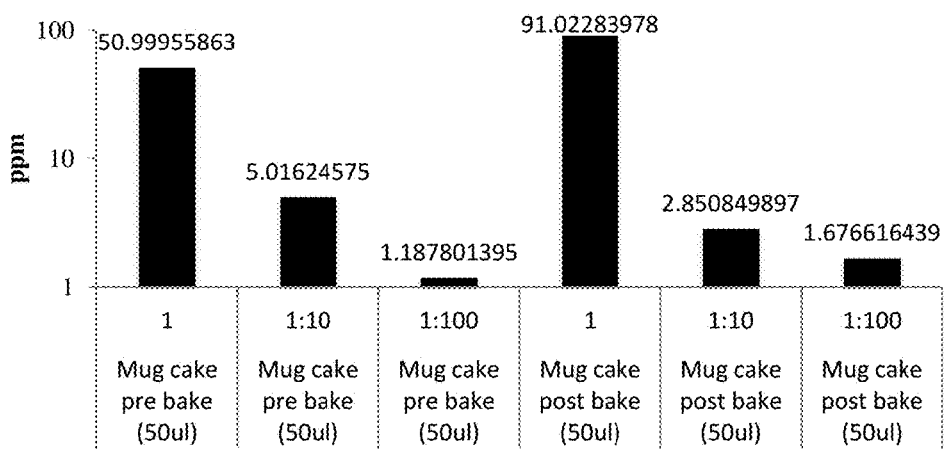
FIG. 32B is a bar chart showing the MB7 detection in FIG. 32A converted to ppm.
Figure 33A:
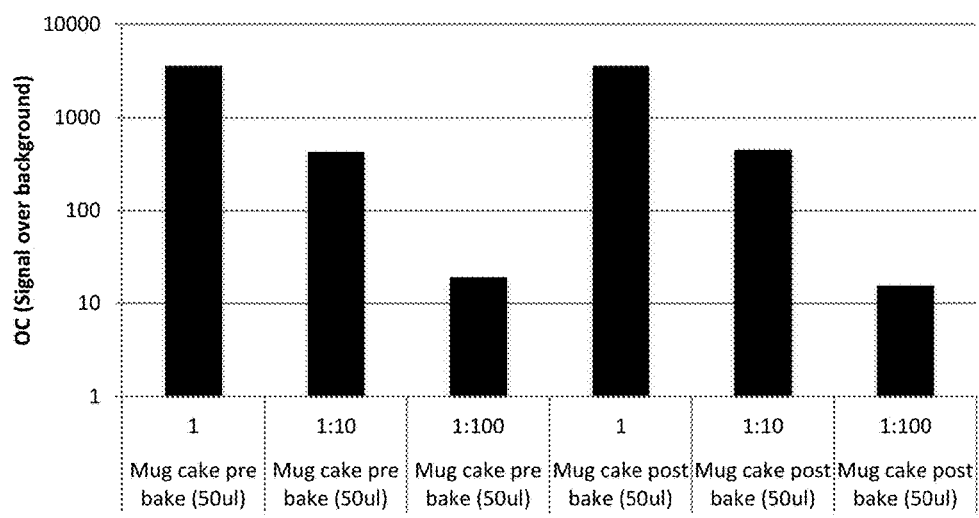
FIG. 33A shows MB9 detection of peanut at low ppm levels spiked into cake pre-baking and post-baking.
Figure 33B:
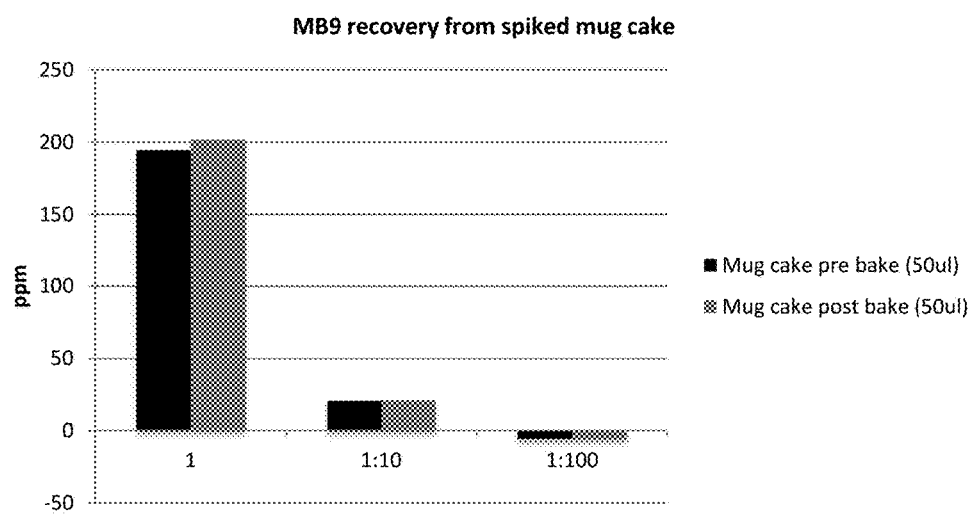
FIG. 33B is a bar chart showing the MB9 detection in FIG. 33A converted to ppm.
Figure 34:
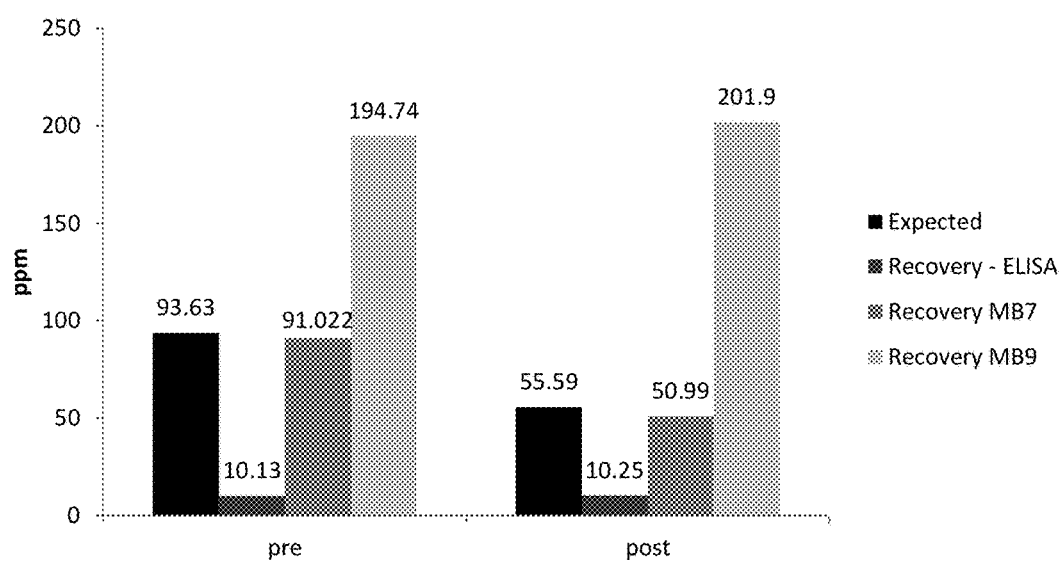
FIG. 34 is a histogram showing MB7 and MB9 recovery rates in K buffer compared to the peanut recovery rate in ELISA assay.

The effect of K buffer on MB7 and MB9 binding affinity to peanut allergen in food matrices was also tested. Different amounts of peanut flour were spiked in a mug cake matrix either pre-baking or post-baking. The allergen was retrieved using K buffer and the extracted samples were diluted prior to SPN (i.e. MB7 or MB9) detection. FIGS. 32 (A&B) showed that MB7 can detect low ppm levels spiked into cake pre and post baking when using K buffer as the extraction buffer. Similarly, MB9 can also detect low ppm levels spiked into cake pre and post baking when using K buffer as the extraction buffer, as shown in FIGS. 33 (A&B). As compared to the allergen recovery rate with ELISA assay detection, both MB7 and MB9 significantly increase peanut recovery rate when using K buffer as the extraction buffer (FIG. 34).

Commercially processed foods were also tested. The results indicate that MB7 and MB9 can detected diluted peanut allergen in processed foods such as pretzel and ice cream when using K buffer as the extraction buffer (FIG. 35).

Figure 36A:
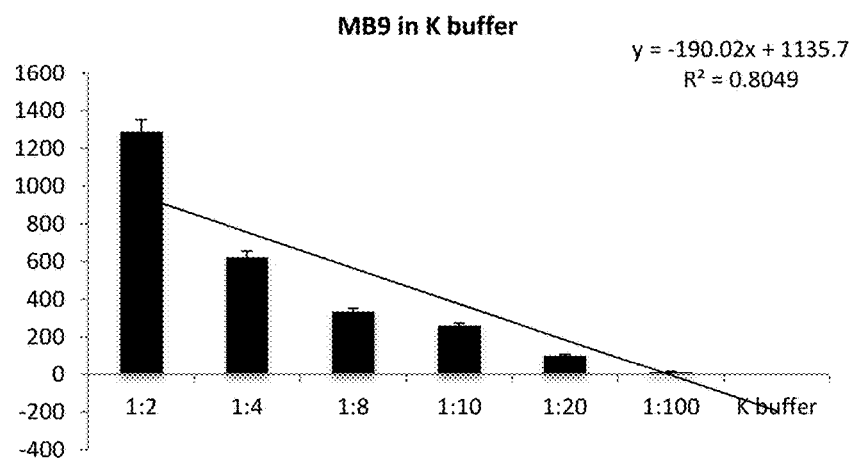
FIG. 36A shows MB9 binding affinity to pure peanut protein in PBS based K buffer.
Figure 36B:
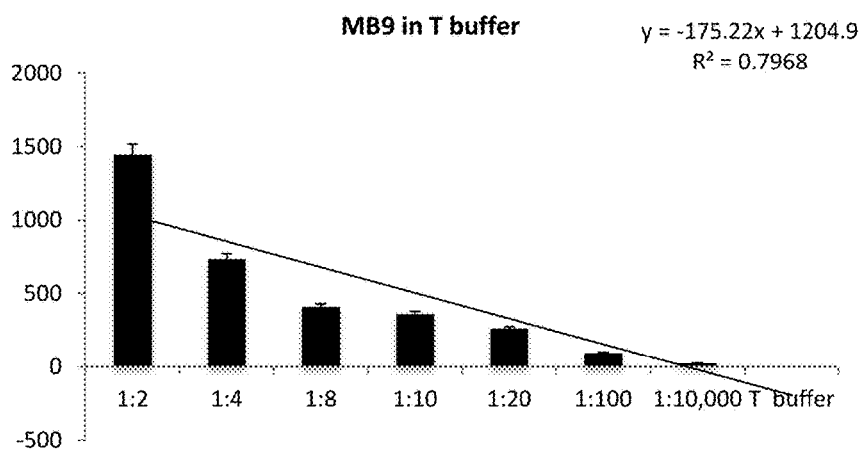
FIG. 36B shows MB9 binding affinity to pure peanut protein in Tris based T buffer.

A test was also performed to compare the effect of K buffer and T buffer on MB9 binding affinity to pure peanut protein. As shown in FIG. 36, T buffer can enable a detection of lower AraH1 levels.

Figure 37A:
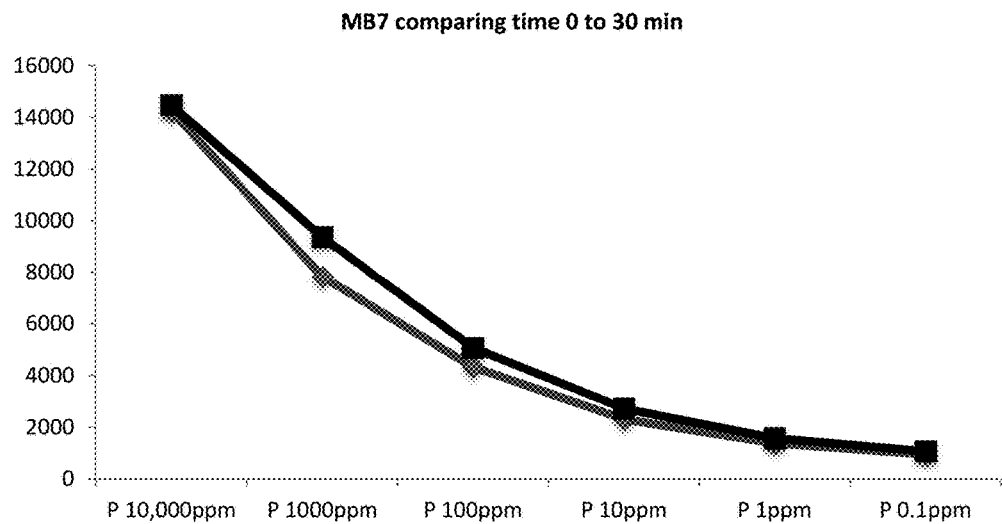
FIG. 37A is a comparison of MB7 detection signals between time 0 minute and time 30 minutes.
Figure 37B:
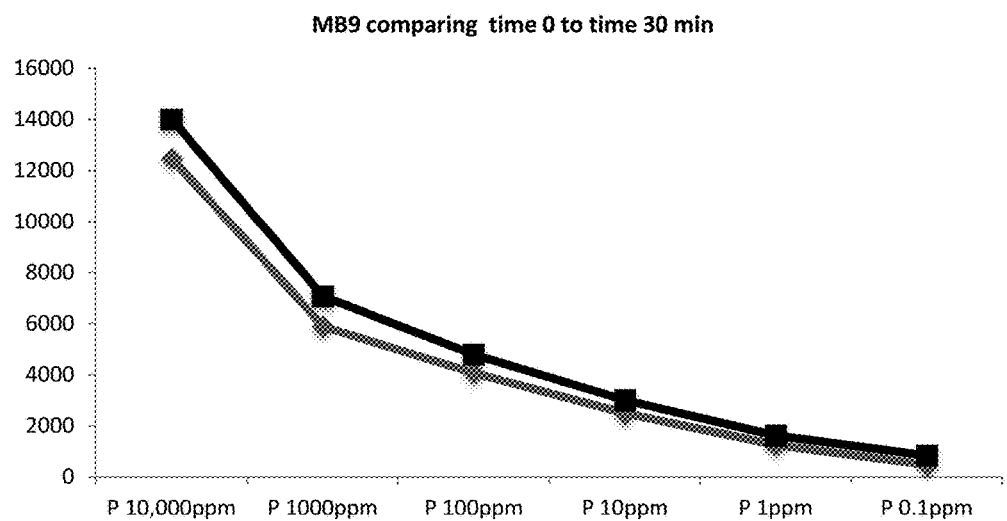
FIG. 37B is a comparison of MB9 detection signals between time 0 minute and time 30 minutes.

We then further tested SPN detection signals at different reaction times and found that the immediate detection signal at 0 min is not significantly different from that at 30 min. FIGS. 37 A&B demonstrated that the immediate detection signals of MB7 and MB9 are similar to those at 30 min.

Example 14: Test of the Effect of Physical Disruption on SPN Binding Affinity

Figure 38A:
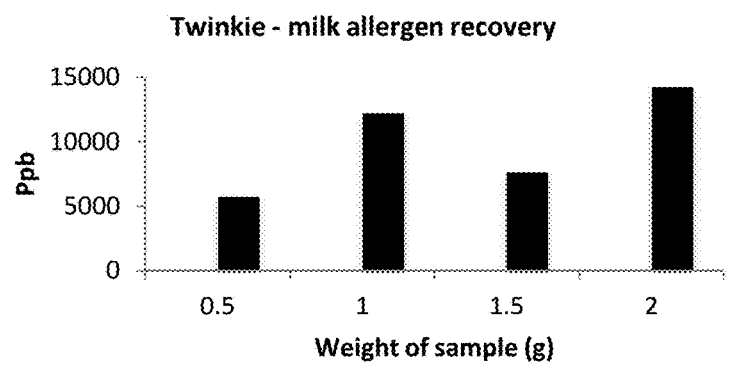
FIG. 38A is a histogram showing milk allergen recovery in Twinkies (TWINKIBID) at different sample sizes.
Figure 38B:
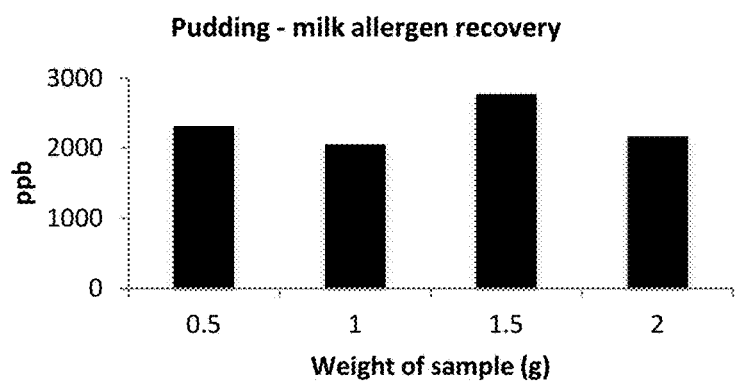
FIG. 38B a histogram showing milk allergen recovery in pudding at different sample sizes.
Figure 38C:
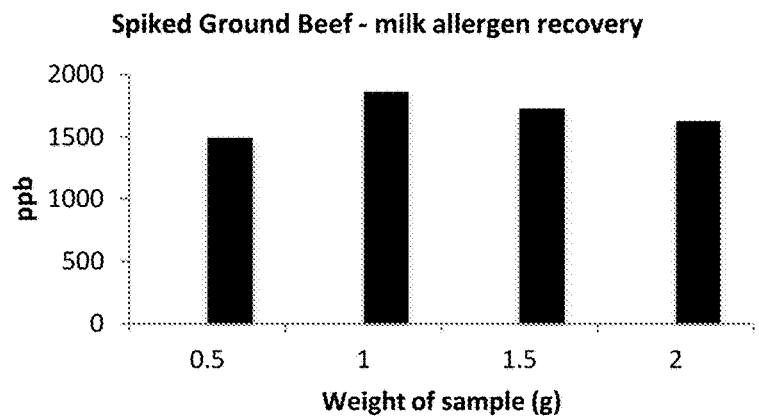
FIG. 38C is a histogram showing milk allergen recovery spiked in ground beef at different sample sizes.
Figure 39:
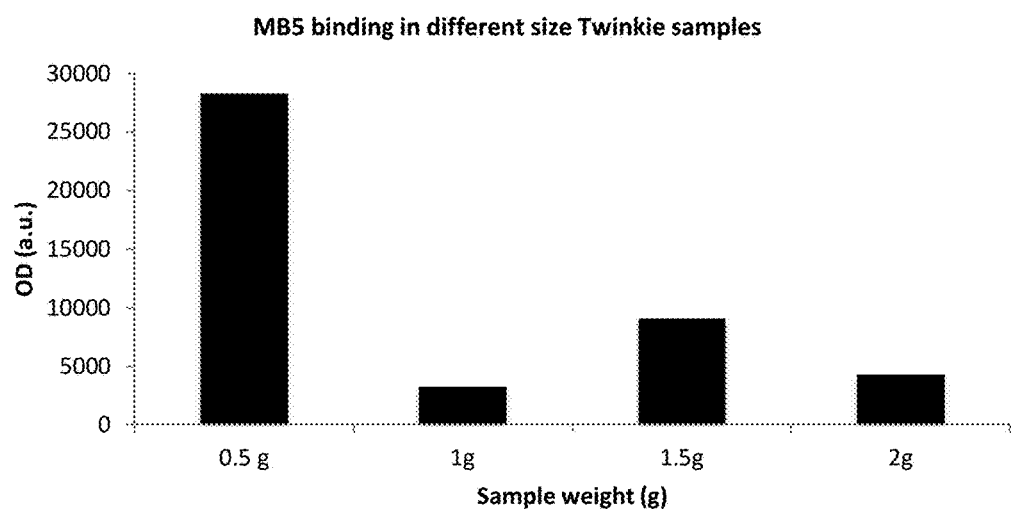
FIG. 39 shows MB5 binding affinity to lysozyme in different size Twinkies (TWINKIE®) samples, indicating that increased sample size can decrease MB5 binding.

We then further tested the sample size, methods for preparing protein samples and physical programs and their influence on allergen recovery and SPN binding affinity to allergen.
Experiment Procedures
Food Samples and Sizes:
Twinkies (TWINKIE®), vanilla pudding and spiked beef at 0.5 g, 1 g, 1.5 g and 2 g were used for the test.
Dissociators:
Different dissociators such as Gentle MAC, mini MAC, Continuum dissociator at low and high Watt were used to process food samples. Protein programs on gentle MAC were used to prepare protein samples.
Extraction Buffer:
T buffer, as discussed in Examples 11 and 12 was used for protein extraction and allergen recovery.
Filtration:
In order to remove debris, to concentrate samples and to enrich specific size proteins, a filtration procedure was performed after processing samples.
Test Results
It is shown that there is no significant difference of milk allergen recovery on all sample sizes (FIG. 38A-C). However, MB5 binding to lysozyme was decreased in larger sample sizes (FIG. 39).

Figure 40A:
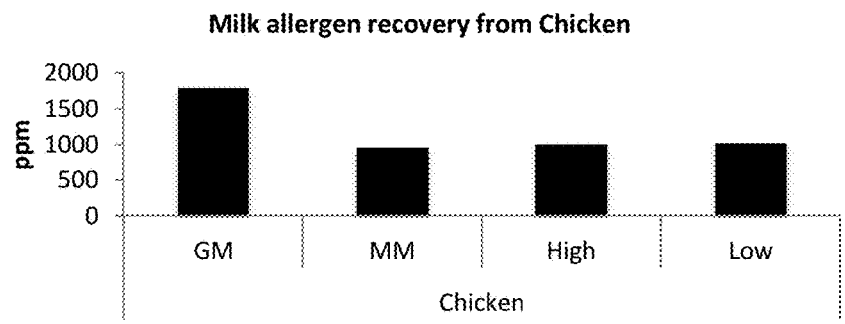
FIG. 40A shows milk allergen recovery from chicken using different dissociators (GM: gentleMAC; MM: mini-MAC; low: Contiuum dissociator low watt; high: Contiuum dissociator high watt).
Figure 40B:
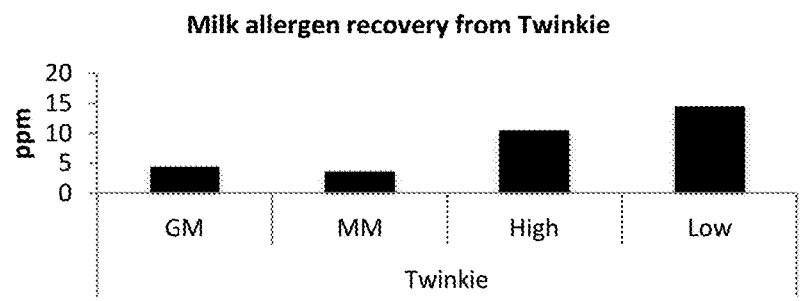
FIG. 40B shows milk allergen recovery from Twinkies (TWINKIE®) using different dissociators.
Figure 40C:
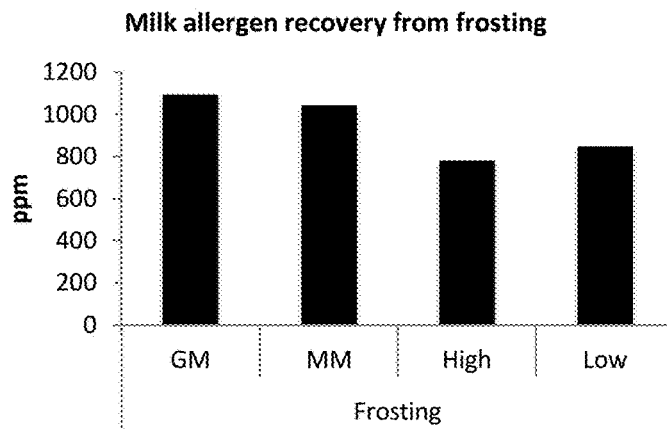
FIG. 40C shows milk allergen recovery from frosting using different dissociators.
Figure 41:
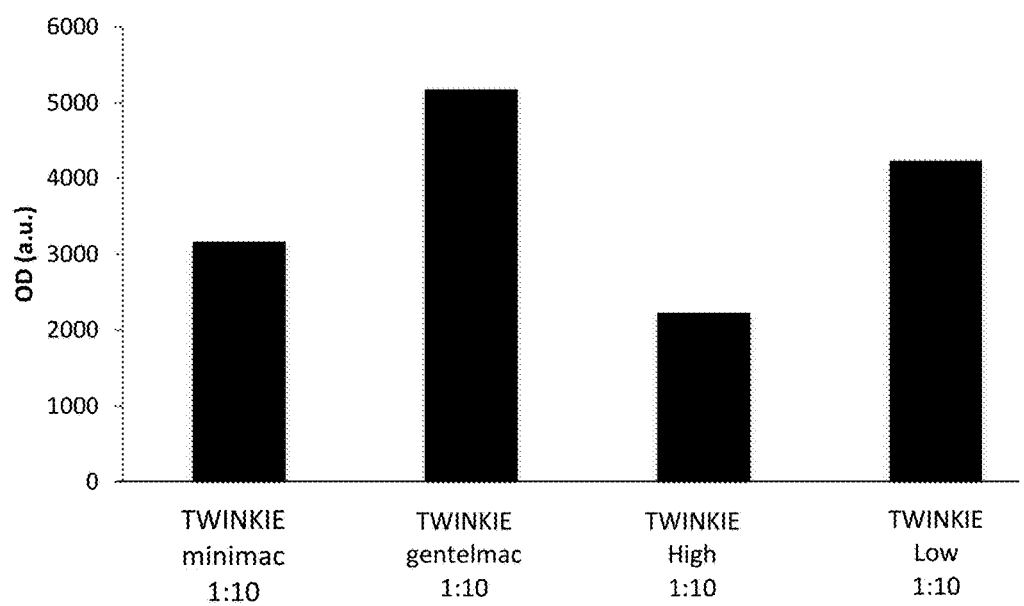
FIG. 41 is a bar chart showing MB5 binding using different dissociators.

Different dissociators and protein programs were tested. The results suggest a high variability between different foods. For example, milk allergen recoveries from chicken, Twinkie (TWINKIE®) and Frosting are different when using different dissociators (FIG. 40A-C). The gentle MAC gave the highest binding of MB5 to lysozyme, as compared to other dissociators. However, the low watt Contiuum dissociator was not significantly different from gentle MAC (FIG. 41).

Example 15: Signal Polynucleotides Selected and Designed for 8 Food Allergens

The general experimental design on screening, selecting and engineering aptamer-based signal polynucleotides that can detect a food allergen is described in Examples 9 and 11. Following such selection and design procedure, an in vitro screening experiment based on SELEX method was carried out and aptamers were selected against the allergen targets including egg, gluten, milk, soy, fish, peanut, cashew and crustacean, over the counter-target (combinations of the non-target proteins) and were further engineered for their capability in detecting targeted food allergens.
Experimental Process Various RNA libraries were used to select for binding ability in selection buffer consisting of 100 mM Tris [pH 8], 5 mM EDTA, 150 mM NaCl, 10 mM MgCl2, 0.1% SDS, 0.1% Gelatin, 1% NP-40 (Tergitol), 0.5% Deoxycholate Sodium at 23° C. A given round of selection began with incubating RNA library members in either the buffer alone (negative selection), then collecting the portion of the library that did not respond (i.e. cleave). The second part of each round (when called for) consisted of incubating the non-responsive molecules from the prior negative selection step with the full combination of non-positive targets (as the counter), or with just the selection buffer again for a second negative selection. Once again, the non-responsive (non-cleaving) molecules would be collected. The final step of each round consists of incubating the material from the previous step with the positive target (each of the allergens as appropriate) in buffer, then collecting the responsive material (i.e. cleaved RNA). Each selection round was followed by reverse transcription to generate cDNA, library amplification through PCR, and regeneration of the RNA library by transcription. After subjecting the initial library of diverse random sequences to varying consecutive rounds of selection (i.e. negative, counter and positive selections), again project-dependent, and the enriched libraries were divided into three fractions to perform the parallel assessments. The parallel assessment involves simultaneously exposing one third of the enriched library to selection buffer alone, another one-third to the counter-target complex in selection buffer, and the final one-third of the enriched library to the target allergen in buffer. Any residual RNA molecules that react indiscriminately to both target allergen and counter-targets, or that still generate a response in the absence of the target allergen were identified and discarded for further analysis.

The enriched RNA libraries after the parallel assessment were subjected to PAGE gel assessment. 40 pmoles of enriched library was exposed separately to either the negative (buffer only), counter target or target allergen in selection buffer. After 5 minutes incubation at 23° C., library exhibiting a positive response (i.e. cleavage) material was collected, ethanol precipitated, reverse transcribed, and PCR-amplified for sequencing and bioinfomatic analysis.
Aptamers Selected A set of aptamer sequences were selected and further designed as signal polynucleotides for detecting 8 different food allergens, including cashew, peanut, fish, milk, soy, gluten, egg and crustacean. 6 different signal polynucleotides were selected for detecting cashew, peanut, fish, egg and gluten, respectively; and 5 for milk, soy and crustacean, respectively. The sequences of these signal polynucleotides are listed in Table 14. In addition to the aptamers (the binding regions of the each signal polynucleotide) which are labeled as SPNs in Table 14, the original sequences including the primer pairs are listed as the starting sequences for designing the signal polynucleotides (i.e. riboswitch sequences), which are labeled as Ribo-SPN in Table 14. The selected aptamers for each food allergen are then further modified at either one or both of the 5' end and the 3' end to optimize the binding affinity. Some of modified sequences are also included in Table 14, which are labeled as SPN-comp. Modified sequences that are intended to have a fluorescein (e.g., FITC/FAM molecule) on the 5'end and a quencher on the 3' end are the signal polynucleotides that will be tested for allergen detection as described herein. Following the design procedure described in Example 10, the 3 dimensional structure of each designed signal polynucleotide are also predicted. See Table 15 for all the thermodynamic data.

TABLE 14

Signal polynucleotides for detecting 8 different food allergens

| Allergen | SPN ID | SEQ ID NO. | Sequence (5'-3') |
|---|---|---|---|
| Cashew | 1501 Ribo-SPN | 18 | TAATACGACTCACTATAGGCGTAGCCTGATGAGGCACA CCACGTCAAAAATCATTGTCACCACGAAGCCGAAACGT GGTGAAAGCCACGTAGCTGCGCC |
| | 1501 SPN | 19 | GCACACCACGTCAAAAATCATTGTCACCACGAAGC |
| | 1501 SPN comp-1 | 20 | GCAGCACACCACGTCAAAAATCATTGTCACCACGAAGCUGC |
| | 1501 SPN com-2 | 21 | AUGCCGCACACCACGUCAAAAAUCAUUGUCACCACGA AGCGGCAU |
| | 1494 Ribo-SPN | 22 | TAATACGACTCACTATAGGCGTAGCCTGATGAGTGCGC AACATAAGTCTCTTGAAAGACCACGTTCAACGAAACGT GGTGAAAGCCACGTAGCTGCGCC |
| | 1494 SPN | 23 | TGCGCAACATAAGTCTCTTGAAAGACCACGTTCAA |
| | 1494 SPN-comp 1 | 24 | TGCGCAACATAAGTCTCTTGAAAGACCACGTTCAAUUG CGCA |
| | 1494 SPN-comp2 | 25 | TGCGCAACATAAGTCTCTTGAAAGACCACGTTCAAGCG CA |
| | 1065 Ribo-SPN | 26 | TAATACGACTCACTATAGGCGTAGCCTGATGAGCACCC ACCATACCAGAAATGTTGACACCACGTGGACGAAACGT GGTGAAAGCCACGTAGCTGCGCC |
| | 1065 SPN | 27 | CACCCACCATACCAGAAATGTTGACACCACGTGGA |
| | 1065 SPN-comp-1 | 28 | CGACACCCACCATACCAGAAATGTTGACACCACGTGGA GUGUCG |
| | 1065 SPN-comp-2 | 29 | CGACCUCACCCACCAUACCAGAAAUGUUGACACCACG UGGAAGGUCG |
| | 1904 Ribo-SPN | 30 | TAATACGACTCACTATAGGCGTAGCCTGATGAGTGCAC AATGTAATTATCAAAATACACCACGTTGGCCGAAACGT GGTGAAAGCCACGTAGCTGCGCC |
| | 1904 SPN | 31 | TGCACAATGTAATTATCAAAATACACCACGTTGGC |
| | 1904 SPN-comp-1 | 32 | CGCAATGCACAATGTAATTATCAAAATACACCACGTTG GCTTGCG |
| | 1904 SPN-comp-2 | 33 | GCCAATGCACAATGTAATTATCAAAATACACCACGTTG GC |
| | 1 Ribo-SPN | 34 | TAATACGACTCACTATAGGCGTAGCCTGATGAGCCACA TCGTGCAATGCCCGAAACATACCACGTAGACGAAACGT GGTGAAAGCCACGTAGCTGCGCC |
| | 1 SPN | 35 | CCACATCGTGCAATGCCCGAAACATACCACGTAGA |
| | 1 SPN-comp-1 | 36 | CCACATCGTGCAATGCCCGAAACATACCACGTAGAATG TGG |
| | 1 SPN-comp-2 | 37 | GCTTACCACATCGTGCAATGCCCGAAACATACCACGTA GATAAGC |
| | 28 Ribo-SPN | 38 | TAATACGACTCACTATAGGCGTAGCCTGATGAGCTATG CAGTGATGATTAAAGATACCACCACGTGAGCGAAACGT GGTGAAAGCCACGTAGCTGCGCC |
| | 28 SPN | 39 | CTATGCAGTGATGATTAAAGATACCACCACGTGAG |
| | 28 SPN-comp-1 | 40 | CTATGCAGTGATGATTAAAGATACCACCACGTGCATAG |
| | 28 SPN-comp-2 | 41 | GCTTACTATGCAGTGATGATTAAAGATACCACCACGTG ATAAGC |
| Peanut | 2047 Ribo-SPN | 42 | TAATACGACTCACTATAGGCGTAGCCTGATGAGCAAAT AGTTACAAACACCACGTAGCGAAACGTGGTGAAAGCC ACGTAGCTGCGCC |
| | 2047 SPN | 43 | CAAATAGTTACAAACACCACGTAG |
| | 2047 SPN-comp-1 | 44 | CAAATAGTTACAAACACCACGTAGATTTG |
| | 2047 SPN-comp-2 | 45 | GCTTACAAATAGTTACAAACACCACGTAGTAAGC |
| | 1981 Ribo-SPN | 46 | TAATACGACTCACTATAGGCGTAGCCTGATGAGCCCAA CTGTACAGTACACCACGTAGCGAAACGTGGTGAAAGCC ACGTAGCTGCGCC |
| | 1981 SPN | 47 | CCCAACTGTACAGTACACCACGTAG |
| | 1981 SPN-comp-1 | 48 | CCCAACTGTACAGTACACCACGTAGTTGGG |
| | 1981 SPN-comp-2 | 49 | GCTTACCCAACTGTACAGTACACCACGTAGTAAGC |
| | 2108 Ribo-SPN | 50 | TAATACGACTCACTATAGGCGTAGCCTGATGAGCACAC ACACATTCCACCACGTCACGCGAAACGTGGTGAAAGCC ACGTAGCTGCGCC |

TABLE 14-continued

Signal polynucleotides for detecting 8 different food allergens

| Allergen | SPN ID | SEQ ID NO. | Sequence (5'-3') |
| --- | --- | --- | --- |
| | 2108-SPN | 51 | CACACACACATTCCACCACGTCACG |
| | 2108 SPN-comp-1 | 52 | CACACACACATTCCACCACGTCACGTGTGTGTG |
| | 2108 SPN-comp-2 | 53 | GCTTACACACACACATTCCACCACGTCACGTAAGC |
| | 1785 Ribo-SPN | 54 | TAATACGACTCACTATAGGCGTAGCCTGATGAGCACACGTTACCACACCACGTTGACGCGAAACGTGGTGAAAGCCACGTAGCTGCGCC |
| | 1785 SPN | 55 | CACACGTTACCACACCACGTTGACG |
| | 1785 SPN-comp-1 | 56 | CACACGTTACCACACCACGTTGACGAACGTGTG |
| | 1785 SPN-comp-2 | 57 | GCTTACACACGTTACCACACCACGTTGACGTAAGC |
| | 1 Ribo-SPN | 58 | TAATACGACTCACTATAGGCGTAGCCTGATGAGCGTGCCCGAAACACACCACGATGCGAAACGTGGTGAAAGCCACGTAGCTGCGCC |
| | 1 SPN | 59 | CGTGCCCGAAACACACCACGATG |
| | 1 SPN-comp-1 | 60 | CGTGCCCGAAACACACCACGATGGGGCACG |
| | 1 SPN-comp-2 | 61 | GCTTACGTGCCCGAAACACACCACGATGTAAGC |
| | 7 Ribo-SPN | 62 | TAATACGACTCACTATAGGCGTAGCCTGATGAGCTCACCACATACCATGTACCACGTGCGAAACGTGGTGAAAGCCACGTAGCTGCGCC |
| | 7 SPN | 63 | CTCACCACATACCATGTACCACGTG |
| | 7 SPN-comp-1 | 64 | CTCACCACATACCATGTACCACGTGGGTGAG |
| | 7 SPN-comp-2 | 65 | GCTTACTCACCACATACCATGTACCACGTGTAAGC |
| Milk | 35 Ribo-SPN | 66 | TAATACGACTCACTATAGGCGTAGCCTGATGAGTTCACTGGCTGCACCCACCACCGCGTTCCACGAAACGTGGTGAAGCCACGTAGCTGCGCC |
| | 35 SPN | 67 | TTCACTGGCTGCACCCACCACCGCGTTCCA |
| | 35 SPN-comp-1 | 68 | TTCACTGGCTGCACCCACCACCGCGTTCCAGTGAA |
| | 35 SPN-comp-2 | 69 | GCTTATTCACTGGCTGCACCCACCACCGCGTTCCATAAGC |
| | 45 Ribo-SPN | 70 | TAATACGACTCACTATAGGCGTAGCCTGATGAGCATCCACGGTGACGCTAATCCCACGTTCGACGAAACGTGGTGAAGCCACGTAGCTGCGCC |
| | 45 SPN | 71 | CATCCACGGTGACGCTAATCCCACGTTCGA |
| | 45 SPN-comp-1 | 72 | CATCCACGGTGACGCTAATCCCACGTTCGATGGATG |
| | 45 SPN-comp-2 | 73 | TCGAACGCATCCACGGTGACGCTAATCCCACGTTCGA |
| | 74 Ribo-SPN | 74 | TAATACGACTCACTATAGGCGTAGCCTGATGAGACAATGCAGATGCGCCCACCACGGATCACTCGAAACGTGGTGAAGCCACGTAGCTGCGCC |
| | 74 SPN | 75 | ACAATGCAGATGCGCCCACCACGGATCACT |
| | 74 SPN-comp-1 | 76 | ACAATGCAGATGCGCCCACCACGGATCACTCATTGT |
| | 74 SPN-comp-2 | 77 | GCTTAACAATGCAGATGCGCCCACCACGGATCACTTAAGC |
| | 74 SPN-comp-3 | 78 | GCAGTGAACAATGCAGATGCGCCCACCACGGATCACTGC |
| | 16 Ribo-SPN | 79 | TAATACGACTCACTATAGGCGTAGCCTGATGAGCAACCAAGCACGCTGCATCACGTTTCATCGCGAAACGTGGTGAAGCCACGTAGCTGCGCC |
| | 16 SPN | 80 | CAACCAAGCACGCTGCATCACGTTTCATCG |
| | 16 SPN-comp-1 | 81 | CAACCAAGCACGCTGCATCACGTTTCATCGTTGGTTG |
| | 16 SPN-comp-2 | 82 | GCTTACAACCAAGCACGCTGCATCACGTTTCATCGTAAGC |
| | 1 Ribo-SPN | 83 | TAATACGACTCACTATAGGCGTAGCCTGATGAGCTCACAGCCCGAAACACATCGCCACGTTCACGAAACGTGGTGAAGCCACGTAGCTGCGCC |
| | 1 SPN | 84 | CTCACAGCCCGAAACACATCGCCACGTTCA |
| | 1 SPN-comp-1 | 85 | CTCACAGCCCGAAACACATCGCCACGTTCATGTGAG |
| | 1 SPN-comp-2 | 86 | GCTTACTCACAGCCCGAAACACATCGCCACGTTCATAAGC |
| | 1 SPN-comp-3 | 87 | TGAACTCACAGCCCGAAACACATCGCCACGTTCA |

TABLE 14-continued

Signal polynucleotides for detecting 8 different food allergens

| Allergen | SPN ID | SEQ ID NO. | Sequence (5'-3') |
|---|---|---|---|
| Fish | 301 Ribo-SPN | 88 | TAATACGACTCACTATAGGCGTAGCCTGATGAGCTCAATACTACGTCAATTCACAGATGATAGACACCACGGACGAAACGTGGTGAAAGCCACGTAGCTGCGCC |
| | 301 SPN | 89 | CTCAATACTACGTCAATTCACAGATGATAGACACCACGGA |
| | 301 SPN-comp-1 | 90 | CTCAATACTACGTCAATTCACAGATGATAGACACCACGGATTGAG |
| | 301 SPN-comp-2 | 91 | GCTTACTCAATACTACGTCAATTCACAGATGATAGACACCACGGATAAGC |
| | 301 SPN-comp-3 | 92 | TCCGTGGCTCAATACTACGTCAATTCACAGATGATAGACACCACGGA |
| | 333 Ribo-SPN | 93 | TAATACGACTCACTATAGGCGTAGCCTGATGAGTCCAACACCACGTAACGTACACTGCATGTGATTGGTGCAACGAAACGTGGTGAAAGCCACGTAGCTGCGCC |
| | 333 SPN | 94 | TCCAACACCACGTAACGTACACTGCATGTGATTGGTGCAA |
| | 333 SPN-comp-1 | 95 | TCCAACACCACGTAACGTACACTGCATGTGATTGGTGCAATTGGA |
| | 333 SPN-comp-2 | 96 | GCTTATCCAACACCACGTAACGTACACTGCATGTGATTGGTGCAATAAGC |
| | 365 Ribo-SPN | 97 | TAATACGACTCACTATAGGCGTAGCCTGATGAGTGGCGCCCGACTGATCAACTAGACATCACGTTAGCATTCCGCGAAACGTGGTGAAAGCCACGTAGCTGCGCC |
| | 365 SPN | 98 | TGGCGCCGACTGATCAACTAGACATCACGTTAGCATTCCG |
| | 365 SPN-comp-1 | 99 | TGGCGCCGACTGATCAACTAGACATCACGTTAGCATTCCGGGCGCCA |
| | 365 SPN-comp-2 | 100 | GCTTATGGCGCCGACTGATCAACTAGACATCACGTTAGCATTCCGTAAGC |
| | 38 Ribo-SPN | 101 | TAATACGACTCACTATAGGCGTAGCCTGATGAGCCAGCAACCAGGTTACCTCCCATCACGCTTCGTCTCAGGACGAAACGTGGTGAAAGCCACGTAGCTGCGCC |
| | 38 SPN | 102 | CCAGCAACCAGGTTACCTCCCATCACGCTTCGTCTCAGGA |
| | 38 SPN-comp-1 | 103 | CCAGCAACCAGGTTACCTCCCATCACGCTTCGTCTCAGGATTGCTGG |
| | 38 SPN-comp-2 | 104 | TCCTGAGACCAGCAACCAGGTTACCTCCCATCACGCTTCGTCTCAGGA |
| | 1 Ribo-SPN | 105 | TAATACGACTCACTATAGGCGTAGCCTGATGAGCTGACACCACACAAACGATTATGACCACGTTATCGTACATAGCGAAACGTGGTGAAAGCCACGTAGCTGCGCC |
| | 1 SPN | 106 | CTGACACCACAAACGATTATGACCACGTTATCGTACATAG |
| | 1 SPN-comp-1 | 107 | CTGACACCACAAACGATTATGACCACGTTATCGTACATAGGGTGTCAG |
| | 1 SPN-comp-2 | 108 | CTATGTACTGACACCACAAACGATTATGACCACGTTATCGTACATAG |
| | 27 Ribo-SPN | 109 | TAATACGACTCACTATAGGCGTAGCCTGATGAGTAGGTCAAGTGCGCTAAAACACACCGCGTTAGTTCACCAACGAAACGTGGTGAAAGCCACGTAGCTGCGCC |
| | 27 SPN | 110 | TAGGTCAAGTGCGCTAAAACACACCGCGTTAGTTCACCAA |
| | 27 SPN-comp-1 | 111 | TAGGTCAAGTGCGCTAAAACACACCGCGTTAGTTCACCAAGACCTA |
| | 27 SPN-comp-2 | 112 | GCTTGGTGTAGGTCAAGTGCGCTAAAACACACCGCGTTAGTTCACCAAGC |
| Egg | 1013 Ribo-SPN | 113 | TAATACGACTCACTATAGGCGTAGCCTGATGAGGCCACCTCACTGTGTTTTGTTGCACAACATAATATGATGACGTGCCGAAACGTGGTGAAAGCCACGTAGCTGCGCC |
| | 1013 SPN | 114 | GCCACCTCACTGTGTTTTGTTGCACAACATAATATGATGACGTGC |
| | 1013 SPN-comp-1 | 115 | GCCACCTCACTGTGTTTTGTTGCACAACATAATATGATGACGTGCGGTGGC |
| | 1013 SPN-comp-2 | 116 | GCACGCCACCTCACTGTGTTTTGTTGCACAACATAATATGATGACGTGC |
| | 851 Ribo-SPN | 117 | TAATACGACTCACTATAGGCGTAGCCTGATGAGGCGTTCCCCACCGTTGCCCACGCTTAACTGGACAAAGATGGGCCCGAAACGTGGTGAAAGCCACGTAGCTGCGCC |
| | 851 SPN | 118 | GCGTTCCCCACCGTTGCCCACGCTTAACTGGACAAAGATGGGCCC |
| | 851 SPN-comp-1 | 119 | GCGTTCCCCACCGTTGCCCACGCTTAACTGGACAAAGATGGGCCCAACGC |

TABLE 14-continued

Signal polynucleotides for detecting 8 different food allergens

| Allergen | SPN ID | SEQ ID NO. | Sequence (5'-3') |
|---|---|---|---|
| | 851 SPN-comp-2 | 120 | GGGCCCAGCGTTCCCCACCGTTGCCCACGCTTAACTGGACAAAGATGGGGCCC |
| | 505 Ribo-SPN | 121 | TAATACGACTCACTATAGGCGTAGCCTGATGAGTCTGTGCACATCACTCGACCTCTACGGCTGTATTGATCCTGCATACGAAACGTGGTGAAAGCCACGTAGCTGCGCC |
| | 505 SPN | 122 | TCTGTGCACATCACTCGACCTCTACGGCTGTATTGATCCTGCATA |
| | 505 SPN-comp-1 | 123 | TCTGTGCACATCACTCGACCTCTACGGCTGTATTGATCCTGCATAGTGCACAGA |
| | 505 SPN-comp-2 | 124 | CCTATGCTCTGTGCACATCACTCGACCTCTACGGCTGTATTGATCCTGCATAGG |
| | 780 Ribo-SPN | 125 | TAATACGACTCACTATAGGCGTAGCCTGATGAGCGTCCAACGTTCGATCAGAACCGCGTTCAGGCTGATGATTGTACGCGAAACGTGGTGAAAGCCACGTAGCTGCGCC |
| | 780 SPN | 126 | CGTCCAACGTTCGATCAGAACCGCGTTCAGGCTGATGATTGTACG |
| | 780 SPN-comp-1 | 127 | CGTCCAACGTTCGATCAGAACCGCGTTCAGGCTGATGATTGTACGTTCCACG |
| | 780 SPN-comp-2 | 128 | GCTTACGTCCAACGTTCGATCAGAACCGCGTTCAGGCTGATGATTGTACGTAAGC |
| | 1 Ribo-SPN | 129 | TAATACGACTCACTATAGGCGTAGCCTGATGAGCATCAGTGCGTTCTGCCTTTGCAACCACACAACACACCGTATGAGCGAAACGTGGTGAAAGCCACGTAGCTGCGCC |
| | 1 SPN | 130 | CATCAGTGCGTTCTGCCTTTGCAACCACACAACACACCGTATGAG |
| | 1 SPN-comp-1 | 131 | CTCATACATCAGTGCGTTCTGCCTTTGCAACCACACAACACACCGTATGAG |
| | 1 SPN-comp-2 | 132 | GCTTACATCAGTGCGTTCTGCCTTTGCAACCACACAACACACCGTATGAGTAAGC |
| | 17 Ribo-SPN | 133 | TAATACGACTCACTATAGGCGTAGCCTGATGAGCCAACTGTGCACACTGTTCGCTTATCGAGCTGTGTACCTCCATAGCGAAACGTGGTGAAAGCCACGTAGCTGCGCC |
| | 17 SPN | 134 | CCAACTGTGCACACTGTTCGCTTATCGAGCTGTGTACCTCCATAG |
| | 17 SPN-comp-1 | 135 | CCAACTGTGCACACTGTTCGCTTATCGAGCTGTGTACCTCCATAGGTTGG |
| | 17 SPN-comp-2 | 136 | CTATGGCCAACTGTGCACACTGTTCGCTTATCGAGCTGTGTACCTCCATAG |
| Gluten | 457 Ribo-SPN | 137 | TAATACGACTCACTATAGGCGTAGCCTGATGAGCTTGGTCACCTTTCCTGACATTAACACAGGCGAAACGTGGTGAAGCCACGTAGCTGCGCC |
| | 457 SPN | 138 | CTTGGTCACCTTTCCTGACATTAACACAGG |
| | 457 SPN-comp-1 | 139 | CTTGGTCACCTTTCCTGACATTAACACAGGCCAAG |
| | 457 SPN-comp-2 | 140 | CCTGTCTTGGTCACCTTTCCTGACATTAACACAGG |
| | 491 Ribo-SPN | 141 | TAATACGACTCACTATAGGCGTAGCCTGATGAGTTTTCCCGATACGGCTACGAATTGCGACAACGAAACGTGGTGAAGCCACGTAGCTGCGCC |
| | 491 SPN | 142 | TTTTCCCGATACGGCTACGAATTGCGACAA |
| | 491 SPN-comp-1 | 143 | CCTTTTCCCGATACGGCTACGAATTGCGACAAAAGG |
| | 491 SPN-comp-2 | 144 | GCTTATTTTCCCGATACGGCTACGAATTGCGACAATAAGC |
| | 578 Ribo-SPN | 145 | TAATACGACTCACTATAGGCGTAGCCTGATGAGGCACCAATTTTACCGATTTTGGTGGACAGCCGAAACGTGGTGAAGCCACGTAGCTGCGCC |
| | 578 SPN | 146 | GCACCAATTTTACCGATTTTGGTGGACAGC |
| | 578 SPN-comp-1 | 147 | GCTGTCCGCACCAATTTTACCGATTTTGGTGGACAGC |
| | 578 SPN-comp-2 | 148 | GCACCAATTTTACCGATTTTGGTGGACAGCTTGGTGC |
| | 1514 Ribo-SPN | 149 | TAATACGACTCACTATAGGCGTAGCCTGATGAGCGTACAACCCACCACCGTTGTCCACAAATGCGAAACGTGGTGAAGCCACGTAGCTGCGCC |
| | 1514 SPN | 150 | CGTACAACCCACCACCGTTGTCCACAAATG |
| | 1514 SPN-comp-1 | 151 | CATTTGCGTACAACCCACCACCGTTGTCCACAAATG |
| | 1514 SPN-comp-2 | 152 | CGTACAACCCACCACCGTTGTCCACAAATGTTGTACG |
| | 1 Ribo-SPN | 153 | TAATACGACTCACTATAGGCGTAGCCTGATGAGTGCGTCAACGGCCGTCCCGAAACGTGAATACGAAACGTGGTGAAAGCCACGTAGCTGCGCC |

TABLE 14-continued

Signal polynucleotides for detecting 8 different food allergens

| Allergen | SPN ID | SEQ ID NO. | Sequence (5'-3') |
| --- | --- | --- | --- |
| | 1 SPN | 154 | TGCGTCAACGGCCGTCCCGAAACGTGAATA |
| | 1 SPN-comp-1 | 155 | TATTCATGCGTCAACGGCCGTCCCGAAACGTGAATA |
| | 1 SPN-comp-2 | 156 | GCTTATGCGTCAACGGCCGTCCCGAAACGTGAATATAAGC |
| | 35 Ribo-SPN | 157 | TAATACGACTCACTATAGGCGTAGCCTGATGAGGTTACCCCGAAACGGCCCTAACTGCATCAGCGAAACGTGGTGAAAGCCACGTAGCTGCGCC |
| | 35 SPN | 158 | GTTACCCCGAAACGGCCCTAACTGCATCAG |
| | 35 SPN-comp-1 | 159 | CTGATGCGTTACCCCGAAACGGCCCTAACTGCATCAG |
| | 35 SPN-comp-2 | 160 | GTTACCCCGAAACGGCCCTAACTGCATCAGGGGTAAC |
| Soy | 1 Ribo-SPN | 161 | TAATACGACTCACTATAGGCGTAGCCTGATGAGCCGCATCACCACCCAAACCACCGTTCGAAACGTGGTGAAAGCCACGTAGCTGCGCC |
| | 1 SPN | 162 | CCGCATCACCACCCAAACCACCGTT |
| | 1 SPN-comp-1 | 163 | CCGCATCACCACCCAAACCACCGTTATGCGG |
| | 1 SPN-comp-2 | 164 | AACGGTCCGCATCACCACCCAAACCACCGTT |
| | 2 Ribp-SPN | 165 | TAATACGACTCACTATAGGCGTAGCCTGATGAGCCTGCTCCATCCGCGCCAGCCTCACCGAAACGTGGTGAAAGCCACGTAGCTGCGCC |
| | 2 SPN | 166 | CCTGCTCCATCCGCGCCAGCCTCAC |
| | 2 SPN-comp-1 | 167 | CCTGCTCCATCCGCGCCAGCCTCACGCAGG |
| | 2 SPN-comp-2 | 168 | GTGAGGGCCTGCTCCATCCGCGCCAGCCTCAC |
| | 3 Ribo-SPN | 169 | TAATACGACTCACTATAGGCGTAGCCTGATGAGCCAATCTCCTGCCCACGCCGTTCCACGAAACGTGGTGAAAGCCACGTAGCTGCGCC |
| | 3 SPN | 170 | CCAATCTCCTGCCCACGCCGTTCCA |
| | 3 SPN-comp-1 | 171 | CCAATCTCCTGCCCACGCCGTTCCAATTGG |
| | 3 SPN-comp-2 | 172 | CCTGGAACCAATCTCCTGCCCACGCCGTTCCAGG |
| | 4 Ribo-SPN | 173 | TAATACGACTCACTATAGGCGTAGCCTGATGAGCCAATCAAGGACCGCCTTCACCGCTCGAAACGTGGTGAAAGCCACGTAGCTGCGCC |
| | 4 SPN | 174 | CCAATCAAGGACCGCCTTCACCGCT |
| | 4 SPN-comp-1 | 175 | CCAATCAAGGACCGCCTTCACCGCTATTGG |
| | 4 SPN-comp-2 | 176 | CCAGCGGTCCAATCAAGGACCGCCTTCACCGCTGG |
| | 4 SPN-comp-3 | 177 | CCAATCAAGGACCGCCTTCACCGCTGG |
| | 5 Ribo-SPN | 178 | TAATACGACTCACTATAGGCGTAGCCTGATGAGACTCTCGCATCACCAGCCAACTCACCGAAACGTGGTGAAAGCCACGTAGCTGCGCC |
| | 5 SPN | 179 | ACTCTCGCATCACCAGCCAACTCAC |
| | 5 SPN-comp-1 | 180 | GCTTAACTCTCGCATCACCAGCCAACTCACTAAGC |
| | 5 SPN-comp-2 | 181 | ACTCTCGCATCACCAGCCAACTCACGAGAGT |
| Crustacean | 1 Ribo-SPN | 182 | TAATACGACTCACTATAGGCGTAGCCTGATGAGCGGTACTCAGATTACAGAGTGACATCGAAACGTGGTGAAAGCCACGTAGCTGCGCC |
| | 1 SPN | 183 | CGGTACTCAGATTACAGAGTGACAT |
| | 1 SPN-comp-1 | 184 | CGGTACTCAGATTACAGAGTGACATTACCG |
| | 1 SPN-comp-2 | 185 | CCATGTCCGGTACTCAGATTACAGAGTGACATGG |
| | 2 Ribo-SPN | 186 | TAATACGACTCACTATAGGCGTAGCCTGATGAGAGACACCACGGATCCGAACTGGAGCGAAACGTGGTGAAAGCCACGTAGCTGCGCC |
| | 2 SPN | 187 | AGACACCACGGATCCGAACTGGAG |
| | 2 SPN-comp-1 | 188 | AGACACCACGGATCCGAACTGGAGTGTCT |
| | 2 SPN-comp-2 | 189 | CTCCAGAGACACCACGGATCCGAACTGGAG |
| | 3 Ribo-SPN | 190 | TAATACGACTCACTATAGGCGTAGCCTGATGAGCCTCGCAAGATTGCATACGTTAGAACGAAACGTGGTGAAAGCCACGTAGCTGCGCC |

TABLE 14-continued

Signal polynucleotides for detecting 8 different food allergens

| Allergen | SPN ID | SEQ ID NO. | Sequence (5'-3') |
|---|---|---|---|
| | 3 SPN | 191 | CCTCGCAAGATTGCATACGTTAGAA |
| | 3 SPN-comp-1 | 192 | CCTCGCAAGATTGCATACGTTAGAACGAGG |
| | 3 SPN-comp-2 | 193 | CCTTCTCCTCGCAAGATTGCATACGTTAGAAGG |
| | 4 Ribo-SPN | 194 | TAATACGACTCACTATAGGCGTAGCCTGATGAGCACGTAGGAAACGACCTCTACGGAGCGAAACGTGGTGAAAGCCACGTAGCTGCGCC |
| | 4 SPN | 195 | CACGTAGGAAACGACCTCTACGGAG |
| | 4 SPN-comp-1 | 196 | CACGTAGGAAACGACCTCTACGGAGTACGTG |
| | 4 SPN-comp-2 | 197 | CTCCGCACGTAGGAAACGACCTCTACGGAG |
| Aptamers selecte | Aptamers selecte | | Aptamers selecte |
| | 5 SPN | 199 | CCCGAAACCACCACCGTTGTCCAATA |
| | 5 SPN-comp-1 | 200 | CCCGAAACCACCACCGTTGTCCAATATTTCGGG |
| | 5 SPN-comp-2 | 201 | GGTATTCCCGAAACCACCACCGTTGTCCAATACC |

TABLE 15

Thermodynamic data (ΔG) for each sequence

| Allergen | SPN ID | ΔG at 25° C. |
|---|---|---|
| Cashew | 1501 Ribo-SPN | −31 |
| | 1501 SPN | 0.4/0 |
| | 1501 SPN comp-1 | −5.9 |
| | 1501 SPN com-2 | −10.6 |
| | 1494 Ribo-SPN | −31 |
| | 1494 SPN | −2.5/−1.8 |
| | 1494 SPN-comp1 | −9.8/−9.1/−8.8 |
| | 1494 SPN-comp2 | −9.1 |
| | 1065 Ribo-SPN | −31 |
| | 1065 SPN | −2 |
| | 1065 SPN-comp-1 | −12 |
| | 1065 SPN-comp-2 | −10 |
| | 1904 Ribo-SPN | −20 |
| | 1904 SPN | −4 |
| | 1904 SPN-comp-1 | −11 |
| | 1904 SPN-comp-2 | −8.2 |
| | 1 Ribo-SPN | −30 |
| | 1 SPN | −3 |
| | 1 SPN-comp-1 | −9.3 |
| | 1 SPN-comp-2 | −6.8 |
| | 28 Ribo-SPN | −31 |
| | 28 SPN | −2 |
| | 28 SPN-comp-1 | −10.6 |
| | 28 SPN-comp-2 | −7.7 |
| Peanut | 2047 Ribo-SPN | −27 |
| | 2047 SPN | −1 |
| | 2047 SPN-comp-1 | −0.4 |
| | 2047 SPN-comp-2 | −3.5 |
| | 1981 Ribo-SPN | −29 |
| | 1981 SPN | 0 |
| | 1981 SPN-comp-1 | −8 |
| | 1981 SPN-comp-2 | −4 |
| | 2108 Ribo-SPN | −28 |
| | 2108-SPN | −3 |
| | 2108 SPN-comp-1 | −11.8 |
| | 2108 SPN-comp-2 | −4 |
| | 1785 Ribo-SPN | −28 |
| | 1785 SPN | −1 |
| | 1785 SPN-comp-1 | −8 |
| | 1785 SPN-comp-2 | −6 |
| | 1 Ribo-SPN | −28 |
| | 1 SPN | −3 |
| | 1 SPN-comp-1 | −11 |
| | 1 SPN-comp-2 | −6 |

TABLE 15-continued

Thermodynamic data (ΔG) for each sequence

| Allergen | SPN ID | ΔG at 25° C. |
|---|---|---|
| | 7 Ribo-SPN | −28 |
| | 7 SPN | −1 |
| | 7 SPN-comp-1 | −8.7 |
| | 7 SPN-comp-2 | −5 |
| Milk | 35 Ribo-SPN | −29 |
| | 35 SPN | −1 |
| | 35 SPN-comp-1 | −11.5 |
| | 35 SPN-comp-2 | −5 |
| | 45 Ribo-SPN | −30 |
| | 45 SPN | −3 |
| | 45 SPN-comp-1 | −9.5 |
| | 45 SPN-comp-2 | −10.4 |
| | 74 Ribo-SPN | −30 |
| | 74 SPN | −4 |
| | 74 SPN-comp-1 | −7 |
| | 74 SPN-comp-2 | −5 |
| | 74 SPN-comp-3 | 9.5 |
| | 16 Ribo-SPN | −31 |
| | 16 SPN | −1 |
| | 16 SPN-comp-1 | −8 |
| | 16 SPN-comp-2 | −5 |
| | 1 Ribo-SPN | −29 |
| | 1 SPN | 0 |
| | 1 SPN-comp-1 | −5 |
| | 1 SPN-comp-2 | −4 |
| | 1 SPN-comp-3 | −2 |
| Fish | 301 Ribo-SPN | −34 |
| | 301 SPN | −4.5 |
| | 301 SPN-comp-1 | −6 |
| | 301 SPN-comp-2 | −7 |
| | 301 SPN-comp-3 | −13 |
| | 333 Ribo-SPN | −33 |
| | 333 SPN | −6 |
| | 333 SPN-comp-1 | −10 |
| | 333 SPN-comp-2 | −11 |
| | 365 Ribo-SPN | −36 |
| | 365 SPN | −6 |
| | 365 SPN-comp-1 | −13 |
| | 365 SPN-comp-2 | −15 |
| | 38 Ribo-SPN | −37 |
| | 38 SPN | −1 |
| | 38 SPN-comp-1 | −12 |
| | 38 SPN-comp-2 | −17 |
| | 1 Ribo-SPN | −33 |

TABLE 15-continued

Thermodynamic data (ΔG) for each sequence

| Allergen | SPN ID | ΔG at 25° C. |
|---|---|---|
| | 1 SPN | −5 |
| | 1 SPN-comp-1 | −17 |
| | 1 SPN-comp-2 | −17 |
| | 27 Ribo-SPN | −34 |
| | 27 SPN | −7 |
| | 27 SPN-comp-1 | −12 |
| | 27 SPN-comp-2 | −14 |
| Egg | 1013 Ribo-SPN | −40 |
| | 1013 SPN | −11 |
| | 1013 SPN-comp-1 | −19 |
| | 1013 SPN-comp-2 | −13 |
| | 851 Ribo-SPN | −37 |
| | 851 SPN | −9.7 |
| | 851 SPN-comp-1 | −14 |
| | 851 SPN-comp-2 | −18 |
| | 505 Ribo-SPN | −36 |
| | 505 SPN | −8 |
| | 505 SPN-comp-1 | −15 |
| | 505 SPN-comp-2 | −12 |
| | 780 Ribo-SPN | −45 |
| | 780 SPN | −9 |
| | 780 SPN-comp-1 | −14 |
| | 780 SPN-comp-2 | −17 |
| | 1 Ribo-SPN | −34 |
| | 1 SPN | −4 |
| | 1 SPN-comp-1 | −10 |
| | 1 SPN-comp-2 | −11 |
| | 17 Ribo-SPN | −44 |
| | 17 SPN | −12 |
| | 17 SPN-comp-1 | −17 |
| | 17 SPN-comp-2 | −17 |
| Gluten | 457 Ribo-SPN | −30 |
| | 457 SPN | −2 |
| | 457 SPN-comp-1 | −6 |
| | 457 SPN-comp-2 | −7 |
| | 491 Ribo-SPN | −31 |
| | 491 SPN | −4 |
| | 491 SPN-comp-1 | −7 |
| | 491 SPN-comp-2 | −11 |
| | 578 Ribo-SPN | −34 |
| | 578 SPN | −6 |
| | 578 SPN-comp-1 | −15 |
| | 578 SPN-comp-2 | −13 |
| | 1514 Ribo-SPN | −32 |
| | 1514 SPN | −3 |
| | 1514 SPN-comp-1 | −7 |
| | 1514 SPN-comp-2 | −7 |
| | 1 Ribo-SPN | −30 |
| | 1 SPN | −5 |

TABLE 15-continued

Thermodynamic data (ΔG) for each sequence

| Allergen | SPN ID | ΔG at 25° C. |
|---|---|---|
| | 1 SPN-comp-1 | −7 |
| | 1 SPN-comp-2 | −9 |
| | 35 Ribo-SPN | −38 |
| | 35 SPN | −2 |
| | 35 SPN-comp-1 | −13 |
| | 35 SPN-comp-2 | −14 |
| Soy | 1 Ribo-SPN | −28 |
| | 1 SPN | −1.5 |
| | 1 SPN-comp-1 | −6 |
| | 1 SPN-comp-2 | −3 |
| | 2 Ribp-SPN | −31 |
| | 2 SPN | 0.5 |
| | 2 SPN-comp-1 | −7 |
| | 2 SPN-comp-2 | −8 |
| | 3 Ribo-SPN | −27 |
| | 3 SPN | 0.5 |
| | 3 SPN-comp-1 | −1 |
| | 3 SPN-comp-2 | −10 |
| | 4 Ribo-SPN | −35 |
| | 4 SPN | −2 |
| | 4 SPN-comp-1 | −2 |
| | 4 SPN-comp-2 | −14 |
| | 4 SPN-comp-3 | −3 |
| | 5 Ribo-SPN | −31 |
| | 5 SPN | −0.1 |
| | 5 SPN-comp-1 | −2 |
| | 5 SPN-comp-2 | −7 |
| Crustacean | 1 Ribo-SPN | −32 |
| | 1 SPN | −4 |
| | 1 SPN-comp-1 | −5 |
| | 1 SPN-comp-2 | −11 |
| | 2 Ribo-SPN | −30 |
| | 2 SPN | −2 |
| | 2 SPN-comp-1 | −10 |
| | 2 SPN-comp-2 | −6 |
| | 3 Ribo-SPN | −34 |
| | 3 SPN | −2 |
| | 3 SPN-comp-1 | −5 |
| | 3 SPN-comp-2 | −6 |
| | 4 Ribo-SPN | −35 |
| | 4 SPN | −6 |
| | 4 SPN-comp-1 | −8 |
| | 4 SPN-comp-2 | −7 |
| | 5 Ribo-SPN | −27 |
| | 5 SPN | −3 |
| | 5 SPN-comp-1 | −6 |
| | 5 SPN-comp-2 | −3 |

What is claimed is:

1. A method of detecting one or more allergens in a sample comprising, (a) obtaining a sample suspected of containing an allergen by a drill probe and transporting the sample to a collection chamber of a cartridge wherein said drill probe comprises a sample collection needle and a drill bit residing inside the needle, (b) digesting and homogenizing the sample of (a) with one or more buffers in the collection chamber of the cartridge and extracting the sample through one or more extraction membranes in the cartridge, (c) contacting the digested sample with a nucleic acid based detection molecule in a detection chamber that is connected to the cartridge, (d) treating the contacted sample with a light source that provide light of an excitation wavelength to excite the detection molecule, wherein the light source includes light emitting diodes (LEDs), (e) filtering the light emitted from the detection molecule through a light filter, and (f) detecting fluorescent signals using a fluorescence detector that measures the fluorescence emission from the detection molecule and visualizing an interaction of the detection molecule and the allergen through a display window.

2. The method of claim 1 wherein the nucleic acid is an aptamer.

3. The method of claim 2 wherein the aptamer comprises a fluorophore and a quencher which are in sufficient proximity for the quencher to quench fluorescence of the fluorophore.

4. The method of claim 3 wherein the fluorophore and the quencher are linked to opposite ends of the sequence of the aptamer and wherein 5 to 20 nucleobase residues at the 5'-end of the sequence are at least 80% complementary to 5 to 20 nucleobase residues at the 3'-end of the sequence capable of forming a hairpin structure, thereby bringing the quencher in sufficient proximity to the fluorophore for quenching the fluorescence of the fluorophore.

5. The method of claim 2 wherein the detection molecule further comprises a linker sequence 5 to 20 nucleobases in length annealed to the 5'-end of the sequence of the aptamer and having at least 80% complementarity with the 5'-end of the sequence of the aptamer, wherein the aptamer sequence comprises a fluorophore and the linker sequence comprises a quencher, or wherein the aptamer sequence comprises a quencher and the linker sequence comprises a fluorophore.

6. The method of claim 3 wherein binding of the detection molecule to the allergen separates the quencher from the fluorophore, thereby allowing fluorescence detection of the fluorophore.

7. The method of claim 6 wherein the binding of the detection molecule to the allergen causes a change in secondary structure of the detection molecule.

8. The method of claim 2, wherein the collected sample is at least 0.5 g.

9. The method of claim 1, wherein the sample is homogenized using an Archimedes-type screw which is operated by a motor.

10. The method of claim 1, wherein the one or more allergens are food allergens selecting from the group consisting of peanut, tree nuts, egg, milk, soy, wheat, fish and shell-fish.

11. A method of detecting one or more allergens in a sample comprising, (a) obtaining a sample suspected of containing an allergen and transporting the sample to a collection chamber of a cartridge, (b) digesting and homogenizing the sample of (a) in the collection chamber of the cartridge with a T buffer or a K buffer and extracting the sample through one or more extraction membranes in the cartridge, wherein the T buffer comprises Tris (pH8.0), 0.1% SDS, 10 mM $MgCl_2$, 0.1% Gelatin, 1% NP-40, 0.5% Deoxycholate, 100 mM NaCl and 50 mM KCl, and wherein the K buffer comprises 0.1M PBS (pH8.0), 0.1% SDS, 10 mM $MgCl_2$, 0.1% Gelatin, 1% NP-40, 0.5% Deoxycholate, 100 mM NaCl and 50 mM KCl, (c) contacting the digested sample with a nucleic acid based detection molecule in a detection chamber that is connected to the cartridge, (d) treating the contacted sample with a light source that provide light of an excitation wavelength to excite the detection molecule, (e) filtering the light emitted from the detection molecule through a light filter, and (f) detecting fluorescent signals using a fluorescence detector that measures the fluorescence emission from the detection molecule and visualizing an interaction of the detection molecule and the allergen through a display window.

* * * * *

SEQUENCE LISTING

```
<160> NUMBER OF SEQ ID NOS: 201

<210> SEQ ID NO 1
<211> LENGTH: 79
<212> TYPE: DNA
<213> ORGANISM: Artificial Sequence
<220> FEATURE:
<223> OTHER INFORMATION: Core Sequence of Signaling Polynucleotide

<400> SEQUENCE: 1
cgcacattcc gcttctaccg gggggggtcga gctgagtgga tgcgaatctg tgggtgggcc    60
gtaagtccgt gtgtgcgaa                                                  79

<210> SEQ ID NO 2
<211> LENGTH: 80
<212> TYPE: DNA
<213> ORGANISM: Artificial Sequence
```

```
<220> FEATURE:
<223> OTHER INFORMATION: Core Sequence of Signaling Polynucleotide
      (5'-T-modified)

<400> SEQUENCE: 2
tcgcacattc cgcttctacc ggggggggtcg agctgagtgg atgcgaatct gtgggtgggc     60
cgtaagtccg tgtgtgcgaa                                                  80

<210> SEQ ID NO 3
<211> LENGTH: 9
<212> TYPE: DNA
<213> ORGANISM: Artificial Sequence
<220> FEATURE:
<223> OTHER INFORMATION: Signaling Polynucleotide Linker Sequence

<400> SEQUENCE: 3 agcgtgtaa                                                               9

<210> SEQ ID NO 4
<211> LENGTH: 40
<212> TYPE: DNA
<213> ORGANISM: Artificial Sequence
<220> FEATURE:
<223> OTHER INFORMATION: Core Sequence of Signaling Polynucleotide

<400> SEQUENCE: 4
gcagctaagc aggcggctca caaaaccatt cgcatgcggc                             40

<210> SEQ ID NO 5
<211> LENGTH: 41
<212> TYPE: DNA
<213> ORGANISM: Artificial Sequence
<220> FEATURE:
<223> OTHER INFORMATION: Core Sequence of Signaling Polynucleotide
      (5'-T- modified)

<400> SEQUENCE: 5
tgcagctaag caggcggctc acaaaaccat tcgcatgcgg c                           41

<210> SEQ ID NO 6
<211> LENGTH: 10
<212> TYPE: DNA
<213> ORGANISM: Artificial Sequence
<220> FEATURE:
<223> OTHER INFORMATION: Signaling Polynucleotide Linker Sequence

<400> SEQUENCE: 6
acgtcgattc                                                              10

<210> SEQ ID NO 7
<211> LENGTH: 46
<212> TYPE: DNA
<213> ORGANISM: Artificial Sequence
<220> FEATURE:
<223> OTHER INFORMATION: Core sequence of Signaling Polynucleotide

<400> SEQUENCE: 7
tgcagctaag caggcggctc acaaaaccat tcgcatgcgg cgctgc                      46

<210> SEQ ID NO 8
<211> LENGTH: 11
<212> TYPE: DNA
<213> ORGANISM: Artificial Sequence
<220> FEATURE:
<223> OTHER INFORMATION: Core Sequnce of Signal polynucleotide
```

<400> SEQUENCE: 8 ggtggggtg g                                                          11

<210> SEQ ID NO 9
<211> LENGTH: 49
<212> TYPE: DNA
<213> ORGANISM: Artificial Sequence
<220> FEATURE:
<223> OTHER INFORMATION: Core Sequence of Signaling polynucleotide

<400> SEQUENCE: 9
aaactactaa ctaggtaaga tcacgcagca ctaaacgacg tagttgcca               49

<210> SEQ ID NO 10
<211> LENGTH: 15
<212> TYPE: DNA
<213> ORGANISM: Artificial Sequence
<220> FEATURE:
<223> OTHER INFORMATION: Core sequence of signal polynucleotide

<400> SEQUENCE: 10
ggttggtgtg gttgg                                                    15

<210> SEQ ID NO 11
<211> LENGTH: 37
<212> TYPE: DNA
<213> ORGANISM: Artificial Sequence
<220> FEATURE:
<223> OTHER INFORMATION: Core sequence of Signal polynucleotide

<400> SEQUENCE: 11
ggggcacgtt tatccgtccc tcctagtggc gtgcccc                            37

<210> SEQ ID NO 12
<211> LENGTH: 45
<212> TYPE: DNA
<213> ORGANISM: Artificial Sequence
<220> FEATURE:
<223> OTHER INFORMATION: Core sequence of Signal polynucloetide

<400> SEQUENCE: 12
gcgcggggca cgtttatccg tccctcctag tggcgtgccc cgcgc                   45

<210> SEQ ID NO 13
<211> LENGTH: 45
<212> TYPE: DNA
<213> ORGANISM: Artificial Sequence
<220> FEATURE:
<223> OTHER INFORMATION: Core Sequence of Signaling Polynucleotide

<400> SEQUENCE: 13
tgcagctaag caggcggctc acaaaaccat tcgcatgcgg ctgca                   45

<210> SEQ ID NO 14
<211> LENGTH: 46
<212> TYPE: DNA
<213> ORGANISM: Artificial Sequence
<220> FEATURE:
<223> OTHER INFORMATION: Core Sequence of Signaling Polynucleotide

<400> SEQUENCE: 14
tgcagctaag caggcggctc acaaaaccat tcgcatgcgg cctgca                  46

<210> SEQ ID NO 15
<211> LENGTH: 47

```
<212> TYPE: DNA
<213> ORGANISM: Artificial Sequence
<220> FEATURE:
<223> OTHER INFORMATION: Sequence of Signaling Polynucleotide

<400> SEQUENCE: 15
tgcagctaag caggcggctc acaaaaccat tcgcatgcgg cgctgca            47

<210> SEQ ID NO 16
<211> LENGTH: 87
<212> TYPE: DNA
<213> ORGANISM: Artificial Sequence
<220> FEATURE:
<223> OTHER INFORMATION: Sequence of Signaling Polynucleotide

<400> SEQUENCE: 16
tcgcacattc cgcttctacc ggggggtcg agctgagtgg atgcgaatct gtgggtgggc    60
cgtaagtccg tgtgtgcgaa tgtgcga                                      87

<210> SEQ ID NO 17
<211> LENGTH: 89
<212> TYPE: DNA
<213> ORGANISM: Artificial Sequence
<220> FEATURE:
<223> OTHER INFORMATION: Sequence of Signaling Polynucleotide

<400> SEQUENCE: 17
tcgcacattc cgcttctacc ggggggtcg agctgagtgg atgcgaatct gtgggtgggc    60
cgtaagtccg tgtgtgcgaa aatgtgcga                                    89

<210> SEQ ID NO 18
<211> LENGTH: 99
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 18
taatacgact cactataggc gtagcctgat gaggcacacc acgtcaaaaa tcattgtcac    60
cacgaagccg aaacgtggtg aaagccacgt agctgcgcc                         99

<210> SEQ ID NO 19
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 19
gcacaccacg tcaaaaatca ttgtcaccac gaagc                             35

<210> SEQ ID NO 20
<211> LENGTH: 41
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 20
gcagcacacc acgtcaaaaa tcattgtcac cacgaagctg c                      41
```

```
<210> SEQ ID NO 21
<211> LENGTH: 45
<212> TYPE: DNA
<213> ORGANISM: Artificial Sequence
<220> FEATURE:
<223> OTHER INFORMATION: Artificial Sequence: In vitro Synthetic nucleic
      acid

<400> SEQUENCE: 21
atgccgcaca ccacgtcaaa aatcattgtc accacgaagc ggcat              45

<210> SEQ ID NO 22
<211> LENGTH: 99
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 22
taatacgact cactataggc gtagcctgat gagtgcgcaa cataagtctc ttgaaagacc    60
acgttcaacg aaacgtggtg aaagccacgt agctgcgcc                          99

<210> SEQ ID NO 23
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 23
tgcgcaacat aagtctcttg aaagaccacg ttcaa                         35

<210> SEQ ID NO 24
<211> LENGTH: 42
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 24
tgcgcaacat aagtctcttg aaagaccacg ttcaattgcg ca                 42

<210> SEQ ID NO 25
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 25
tgcgcaacat aagtctcttg aaagaccacg ttcaagcgca                    40

<210> SEQ ID NO 26
<211> LENGTH: 99
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 26
taatacgact cactataggc gtagcctgat gagcacccac cataccagaa atgttgacac    60
```
cacgtggacg aaacgtggtg aaagccacgt agctgcgcc								99

<210> SEQ ID NO 27
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 27
cacccaccat accagaaatg ttgacaccac gtgga								35

<210> SEQ ID NO 28
<211> LENGTH: 44
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 28
cgacacccac cataccagaa atgttgacac cacgtggagt gtcg							44

<210> SEQ ID NO 29
<211> LENGTH: 47
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 29
cgacctcacc caccatacca gaaatgttga caccacgtgg aaggtcg						47

<210> SEQ ID NO 30
<211> LENGTH: 99
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 30
taatacgact cactataggc gtagcctgat gagtgcacaa tgtaattatc aaaatacacc				60 acgttggccg aaacgtggtg aaagccacgt agctgcgcc							99

<210> SEQ ID NO 31
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 31
tgcacaatgt aattatcaaa atacaccacg ttggc								35

<210> SEQ ID NO 32
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 32
cgcaatgcac aatgtaatta tcaaaataca ccacgttggc ttgcg            45

<210> SEQ ID NO 33
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 33
gccaatgcac aatgtaatta tcaaaataca ccacgttggc                  40

<210> SEQ ID NO 34
<211> LENGTH: 99
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 34
taatacgact cactataggc gtagcctgat gagccacatc gtgcaatgcc cgaaacatac    60
cacgtagacg aaacgtggtg aaagccacgt agctgcgcc                          99

<210> SEQ ID NO 35
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 35
ccacatcgtg caatgcccga aacataccac gtaga                       35

<210> SEQ ID NO 36
<211> LENGTH: 41
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 36
ccacatcgtg caatgcccga aacataccac gtagaatgtg g                41

<210> SEQ ID NO 37
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 37
gcttaccaca tcgtgcaatg cccgaaacat accacgtaga taagc            45

<210> SEQ ID NO 38
<211> LENGTH: 99
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 38
taatacgact cactataggc gtagcctgat gagctatgca gtgatgatta aagataccac    60
cacgtgagcg aaacgtggtg aaagccacgt agctgcgcc                           99

<210> SEQ ID NO 39
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 39
ctatgcagtg atgattaaag ataccaccac gtgag                               35

<210> SEQ ID NO 40
<211> LENGTH: 38
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 40
ctatgcagtg atgattaaag ataccaccac gtgcatag                            38

<210> SEQ ID NO 41
<211> LENGTH: 44
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 41
gcttactatg cagtgatgat taaagatacc accacgtgat aagc                     44

<210> SEQ ID NO 42
<211> LENGTH: 88
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 42
taatacgact cactataggc gtagcctgat gagcaaatag ttacaaacac cacgtagcga    60
aacgtggtga aagccacgta gctgcgcc                                       88

<210> SEQ ID NO 43
<211> LENGTH: 24
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 43
caaatagtta caaacaccac gtag                                           24

<210> SEQ ID NO 44
<211> LENGTH: 29
<212> TYPE: DNA
<213> ORGANISM: Artificial Sequence
<220> FEATURE:

<223> OTHER INFORMATION: Artificial Sequence: In vitro synthetic nucleic
     acid

<400> SEQUENCE: 44
caaatagtta caaacaccac gtagatttg                                       29

<210> SEQ ID NO 45
<211> LENGTH: 34
<212> TYPE: DNA
<213> ORGANISM: Artificial Sequence
<220> FEATURE:
<223> OTHER INFORMATION: Artificial Sequence: In vitro synthetic nucleic
     acid

<400> SEQUENCE: 45
gcttacaaat agttacaaac accacgtagt aagc                                 34

<210> SEQ ID NO 46
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
     acid

<400> SEQUENCE: 46
taatacgact cactataggc gtagcctgat gagcccaact gtacagtaca ccacgtagcg     60
aaacgtggtg aaagccacgt agctgcgcc                                       89

<210> SEQ ID NO 47
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
     acid

<400> SEQUENCE: 47
cccaactgta cagtacacca cgtag                                           25

<210> SEQ ID NO 48
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
     acid

<400> SEQUENCE: 48
cccaactgta cagtacacca cgtagttggg                                      30

<210> SEQ ID NO 49
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
     acid

<400> SEQUENCE: 49
gcttacccaa ctgtacagta caccacgtag taagc                                35

<210> SEQ ID NO 50
<211> LENGTH: 89
<212> TYPE: DNA
<213> ORGANISM: Artificial Sequence

```
<220> FEATURE:
<223> OTHER INFORMATION: Artificial Sequence: In vitro synthetic nucleic
      acid

<400> SEQUENCE: 50
taatacgact cactataggc gtagcctgat gagcacacac acattccacc acgtcacgcg    60
aaacgtggtg aaagccacgt agctgcgcc                                     89

<210> SEQ ID NO 51
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 51
cacacacaca ttccaccacg tcacg                                         25

<210> SEQ ID NO 52
<211> LENGTH: 33
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 52
cacacacaca ttccaccacg tcacgtgtgt gtg                                33

<210> SEQ ID NO 53
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 53
gcttacacac acacattcca ccacgtcacg taagc                              35

<210> SEQ ID NO 54
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 54
taatacgact cactataggc gtagcctgat gagcacacgt taccacacca cgttgacgcg    60
aaacgtggtg aaagccacgt agctgcgcc                                     89

<210> SEQ ID NO 55
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 55
cacacgttac cacaccacgt tgacg                                         25

<210> SEQ ID NO 56
```

```
<211> LENGTH: 33
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 56
cacacgttac cacaccacgt tgacgaacgt gtg                                33

<210> SEQ ID NO 57
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 57
gcttacacac gttaccacac cacgttgacg taagc                              35

<210> SEQ ID NO 58
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 58
taatacgact cactataggc gtagcctgat gagcgtgccc gaaacacaca ccacgatgcg    60
aaacgtggtg aaagccacgt agctgcgcc                                     89

<210> SEQ ID NO 59
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 59
cgtgcccgaa acacacacca cgatg                                         25

<210> SEQ ID NO 60
<211> LENGTH: 32
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 60
cgtgcccgaa acacacacca cgatggggca cg                                 32

<210> SEQ ID NO 61
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 61
gcttacgtgc ccgaaacaca caccacgatg taagc                              35
```

```
<210> SEQ ID NO 62
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 62
taatacgact cactataggc gtagcctgat gagctcacca cataccatgt accacgtgcg     60
aaacgtggtg aaagccacgt agctgcgcc                                      89

<210> SEQ ID NO 63
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 63
ctcaccacat accatgtacc acgtg                                          25

<210> SEQ ID NO 64
<211> LENGTH: 31
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 64
ctcaccacat accatgtacc acgtgggtga g                                   31

<210> SEQ ID NO 65
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 65
gcttactcac cacataccat gtaccacgtg taagc                               35

<210> SEQ ID NO 66
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 66
taatacgact cactataggc gtagcctgat gagttcactg gctgcaccca ccaccgcgtt     60
ccacgaaacg tggtgaaagc cacgtagctg cgcc                                94

<210> SEQ ID NO 67
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 67
```
ttcactggct gcacccacca ccgcgttcca                30

<210> SEQ ID NO 68
<211> LENGTH: 35
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 68
ttcactggct gcacccacca ccgcgttcca gtgaa          35

<210> SEQ ID NO 69
<211> LENGTH: 40
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 69
gcttattcac tggctgcacc caccaccgcg ttccataagc     40

<210> SEQ ID NO 70
<211> LENGTH: 94
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 70
taatacgact cactataggc gtagcctgat gagcatccac ggtgacgcta atcccacgtt     60
cgacgaaacg tggtgaaagc cacgtagctg cgcc                                94

<210> SEQ ID NO 71
<211> LENGTH: 30
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 71
catccacggt gacgctaatc ccacgttcga               30

<210> SEQ ID NO 72
<211> LENGTH: 36
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 72
catccacggt gacgctaatc ccacgttcga tggatg        36

<210> SEQ ID NO 73
<211> LENGTH: 37
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 73
tcgaacgcat ccacggtgac gctaatccca cgttcga                37

<210> SEQ ID NO 74
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 74
taatacgact cactataggc gtagcctgat gagacaatgc agatgcgccc accacggatc    60
actcgaaacg tggtgaaagc cacgtagctg cgcc                               94

<210> SEQ ID NO 75
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 75
acaatgcaga tgcgcccacc acggatcact                                    30

<210> SEQ ID NO 76
<211> LENGTH: 36
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 76
acaatgcaga tgcgcccacc acggatcact cattgt                             36

<210> SEQ ID NO 77
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 77
gcttaacaat gcagatgcgc ccaccacgga tcacttaagc                         40

<210> SEQ ID NO 78
<211> LENGTH: 39
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 78
gcagtgaaca atgcagatgc gcccaccacg gatcactgc                          39

<210> SEQ ID NO 79
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

```
<400> SEQUENCE: 79
taatacgact cactataggc gtagcctgat gagcaaccaa gcacgctgca tcacgtttca    60
tcgcgaaacg tggtgaaagc cacgtagctg cgcc                               94

<210> SEQ ID NO 80
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 80
caaccaagca cgctgcatca cgtttcatcg                                    30

<210> SEQ ID NO 81
<211> LENGTH: 37
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 81
caaccaagca cgctgcatca cgtttcatcg ttggttg                            37

<210> SEQ ID NO 82
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 82
gcttacaacc aagcacgctg catcacgttt catcgtaagc                         40

<210> SEQ ID NO 83
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 83
taatacgact cactataggc gtagcctgat gagctcacag cccgaaacac atcgccacgt    60
tcacgaaacg tggtgaaagc cacgtagctg cgcc                               94

<210> SEQ ID NO 84
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 84
ctcacagccc gaaacacatc gccacgttca                                    30

<210> SEQ ID NO 85
<211> LENGTH: 36
<212> TYPE: DNA
<213> ORGANISM: Artificial Sequence
<220> FEATURE:
```

<223> OTHER INFORMATION: Artificial Sequence: In vitro synthetic nucleic
      acid

<400> SEQUENCE: 85
ctcacagccc gaaacacatc gccacgttca tgtgag                              36

<210> SEQ ID NO 86
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 86
gcttactcac agcccgaaac acatcgccac gttcataagc                          40

<210> SEQ ID NO 87
<211> LENGTH: 34
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 87
tgaactcaca gcccgaaaca catcgccacg ttca                                34

<210> SEQ ID NO 88
<211> LENGTH: 104
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 88
taatacgact cactataggc gtagcctgat gagctcaata ctacgtcaat tcacagatga    60
tagacaccac ggacgaaacg tggtgaaagc cacgtagctg cgcc                   104

<210> SEQ ID NO 89
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 89
ctcaatacta cgtcaattca cagatgatag acaccacgga                          40

<210> SEQ ID NO 90
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 90
ctcaatacta cgtcaattca cagatgatag acaccacgga ttgag                    45

<210> SEQ ID NO 91
<211> LENGTH: 50
<212> TYPE: DNA
<213> ORGANISM: Artificial Sequence

```
<220> FEATURE:
<223> OTHER INFORMATION: Artificial Sequence: In vitro synthetic nucleic
      acid

<400> SEQUENCE: 91
gcttactcaa tactacgtca attcacagat gatagacacc acggataagc          50

<210> SEQ ID NO 92
<211> LENGTH: 47
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 92
tccgtggctc aatactacgt caattcacag atgatagaca ccacgga              47

<210> SEQ ID NO 93
<211> LENGTH: 104
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 93
taatacgact cactataggc gtagcctgat gagtccaaca ccacgtaacg tacactgcat     60
gtgattggtg caacgaaacg tggtgaaagc cacgtagctg cgcc                    104

<210> SEQ ID NO 94
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 94
tccaacacca cgtaacgtac actgcatgtg attggtgcaa                      40

<210> SEQ ID NO 95
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 95
tccaacacca cgtaacgtac actgcatgtg attggtgcaa ttgga                45

<210> SEQ ID NO 96
<211> LENGTH: 50
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 96
gcttatccaa caccacgtaa cgtacactgc atgtgattgg tgcaataagc            50

<210> SEQ ID NO 97
<211> LENGTH: 104
<212> TYPE: DNA
```

<213> ORGANISM: Artificial Sequence
<220> FEATURE:
<223> OTHER INFORMATION: Artificial Sequence: In vitro synthetic nucleic acid

<400> SEQUENCE: 97
taatacgact cactataggc gtagcctgat gagtggcgcc gactgatcaa ctagacatca    60
cgttagcatt ccgcgaaacg tggtgaaagc cacgtagctg cgcc    104

<210> SEQ ID NO 98
<211> LENGTH: 40
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 98
tggcgccgac tgatcaacta gacatcacgt tagcattccg    40

<210> SEQ ID NO 99
<211> LENGTH: 47
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 99
tggcgccgac tgatcaacta gacatcacgt tagcattccg ggcgcca    47

<210> SEQ ID NO 100
<211> LENGTH: 50
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 100
gcttatggcg ccgactgatc aactagacat cacgttagca ttccgtaagc    50

<210> SEQ ID NO 101
<211> LENGTH: 104
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 101
taatacgact cactataggc gtagcctgat gagccagcaa ccaggttacc tcccatcacg    60
cttcgtctca ggacgaaacg tggtgaaagc cacgtagctg cgcc    104

<210> SEQ ID NO 102
<211> LENGTH: 40
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 102
ccagcaacca ggttacctcc catcacgctt cgtctcagga    40

```
<210> SEQ ID NO 103
<211> LENGTH: 47
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 103
ccagcaacca ggttacctcc catcacgctt cgtctcagga ttgctgg              47

<210> SEQ ID NO 104
<211> LENGTH: 48
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 104
tcctgagacc agcaaccagg ttacctccca tcacgcttcg tctcagga             48

<210> SEQ ID NO 105
<211> LENGTH: 104
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 105
taatacgact cactataggc gtagcctgat gagctgacac cacaaacgat tatgaccacg    60
ttatcgtaca tagcgaaacg tggtgaaagc cacgtagctg cgcc                   104

<210> SEQ ID NO 106
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 106
ctgacaccac aaacgattat gaccacgtta tcgtacatag              40

<210> SEQ ID NO 107
<211> LENGTH: 48
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 107
ctgacaccac aaacgattat gaccacgtta tcgtacatag ggtgtcag             48

<210> SEQ ID NO 108
<211> LENGTH: 47
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 108
ctatgtactg acaccacaaa cgattatgac cacgttatcg tacatag              47
```

<210> SEQ ID NO 109
<211> LENGTH: 104
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 109
taatacgact cactataggc gtagcctgat gagtaggtca agtgcgctaa aacacaccgc    60
gttagttcac caacgaaacg tggtgaaagc cacgtagctg cgcc                   104

<210> SEQ ID NO 110
<211> LENGTH: 40
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 110
taggtcaagt gcgctaaaac acaccgcgtt agttcaccaa                         40

<210> SEQ ID NO 111
<211> LENGTH: 46
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 111
taggtcaagt gcgctaaaac acaccgcgtt agttcaccaa gaccta                  46

<210> SEQ ID NO 112
<211> LENGTH: 50
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 112
gcttggtgta ggtcaagtgc gctaaaacac accgcgttag ttcaccaagc              50

<210> SEQ ID NO 113
<211> LENGTH: 109
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 113
taatacgact cactataggc gtagcctgat gaggccacct cactgtgttt tgttgcacaa    60
cataatatga tgacgtgccg aaacgtggtg aaagccacgt agctgcgcc              109

<210> SEQ ID NO 114
<211> LENGTH: 45
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 114
gccacctcac tgtgttttgt tgcacaacat aatatgatga cgtgc                    45

<210> SEQ ID NO 115
<211> LENGTH: 51
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 115
gccacctcac tgtgttttgt tgcacaacat aatatgatga cgtgcggtgg c              51

<210> SEQ ID NO 116
<211> LENGTH: 49
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 116
gcacgccacc tcactgtgtt ttgttgcaca acataatatg atgacgtgc                 49

<210> SEQ ID NO 117
<211> LENGTH: 109
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 117
taatacgact cactataggc gtagcctgat gaggcgttcc ccaccgttgc ccacgcttaa     60
ctggacaaag atgggccccg aaacgtggtg aaagccacgt agctgcgcc               109

<210> SEQ ID NO 118
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 118
gcgttcccca ccgttgccca cgcttaactg gacaaagatg ggccc                    45

<210> SEQ ID NO 119
<211> LENGTH: 50
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 119
gcgttcccca ccgttgccca cgcttaactg gacaaagatg ggcccaacgc               50

<210> SEQ ID NO 120
<211> LENGTH: 52
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 120
gggcccagcg ttccccaccg ttgcccacgc ttaactggac aaagatgggc cc    52

<210> SEQ ID NO 121
<211> LENGTH: 109
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 121
taatacgact cactataggc gtagcctgat gagtctgtgc acatcactcg acctctacgg    60
ctgtattgat cctgcatacg aaacgtggtg aaagccacgt agctgcgcc    109

<210> SEQ ID NO 122
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 122
tctgtgcaca tcactcgacc tctacggctg tattgatcct gcata    45

<210> SEQ ID NO 123
<211> LENGTH: 54
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 123
tctgtgcaca tcactcgacc tctacggctg tattgatcct gcatagtgca caga    54

<210> SEQ ID NO 124
<211> LENGTH: 54
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 124
cctatgctct gtgcacatca ctcgacctct acggctgtat tgatcctgca tagg    54

<210> SEQ ID NO 125
<211> LENGTH: 109
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 125
taatacgact cactataggc gtagcctgat gagcgtccaa cgttcgatca gaaccgcgtt    60
caggctgatg attgtacgcg aaacgtggtg aaagccacgt agctgcgcc    109

<210> SEQ ID NO 126
<211> LENGTH: 45
<212> TYPE: DNA
<213> ORGANISM: Artificial Sequence
<220> FEATURE:

<223> OTHER INFORMATION: Artificial Sequence: In vitro synthetic nucleic
      acid

<400> SEQUENCE: 126
cgtccaacgt tcgatcagaa ccgcgttcag gctgatgatt gtacg                45

<210> SEQ ID NO 127
<211> LENGTH: 52
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 127
cgtccaacgt tcgatcagaa ccgcgttcag gctgatgatt gtacgttcca cg         52

<210> SEQ ID NO 128
<211> LENGTH: 55
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 128
gcttacgtcc aacgttcgat cagaaccgcg ttcaggctga tgattgtacg taagc      55

<210> SEQ ID NO 129
<211> LENGTH: 109
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 129
taatacgact cactataggc gtagcctgat gagcatcagt gcgttctgcc tttgcaacca    60
cacaacacac cgtatgagcg aaacgtggtg aaagccacgt agctgcgcc            109

<210> SEQ ID NO 130
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 130
catcagtgcg ttctgccttt gcaaccacac aacacaccgt atgag                45

<210> SEQ ID NO 131
<211> LENGTH: 51
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 131
ctcatacatc agtgcgttct gcctttgcaa ccacacaaca caccgtatga g            51

<210> SEQ ID NO 132
<211> LENGTH: 55
<212> TYPE: DNA
<213> ORGANISM: Artificial Sequence

```
<220> FEATURE:
<223> OTHER INFORMATION: Artificial Sequence: In vitro synthetic nucleic
      acid

<400> SEQUENCE: 132
gcttacatca gtgcgttctg cctttgcaac cacacaacac accgtatgag taagc         55

<210> SEQ ID NO 133
<211> LENGTH: 109
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 133
taatacgact cactataggc gtagcctgat gagccaactg tgcacactgt tcgcttatcg    60
agctgtgtac ctccatagcg aaacgtggtg aaagccacgt agctgcgcc              109

<210> SEQ ID NO 134
<211> LENGTH: 45
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 134
ccaactgtgc acactgttcg cttatcgagc tgtgtacctc catag                   45

<210> SEQ ID NO 135
<211> LENGTH: 50
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 135
ccaactgtgc acactgttcg cttatcgagc tgtgtacctc cataggttgg              50

<210> SEQ ID NO 136
<211> LENGTH: 51
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 136
ctatggccaa ctgtgcacac tgttcgctta tcgagctgtg tacctccata g            51

<210> SEQ ID NO 137
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 137
taatacgact cactataggc gtagcctgat gagcttggtc acctttcctg acattaacac    60
aggcgaaacg tggtgaaagc cacgtagctg cgcc                               94

<210> SEQ ID NO 138
```

```
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 138
cttggtcacc tttcctgaca ttaacacagg                                      30

<210> SEQ ID NO 139
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 139
cttggtcacc tttcctgaca ttaacacagg ccaag                                35

<210> SEQ ID NO 140
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 140
cctgtcttgg tcacctttcc tgacattaac acagg                                35

<210> SEQ ID NO 141
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 141
taatacgact cactataggc gtagcctgat gagttttccc gatacggcta cgaattgcga     60
caacgaaacg tggtgaaagc cacgtagctg cgcc                                 94

<210> SEQ ID NO 142
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 142
ttttcccgat acggctacga attgcgacaa                                      30

<210> SEQ ID NO 143
<211> LENGTH: 36
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 143
cctttccccg atacggctac gaattgcgac aaaagg                               36
```

<210> SEQ ID NO 144
<211> LENGTH: 40
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 144
gcttattttc ccgatacggc tacgaattgc gacaataagc                                    40

<210> SEQ ID NO 145
<211> LENGTH: 94
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 145
taatacgact cactataggc gtagcctgat gaggcaccaa ttttaccgat tttggtggac              60
agccgaaacg tggtgaaagc cacgtagctg cgcc                                          94

<210> SEQ ID NO 146
<211> LENGTH: 30
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 146
gcaccaattt taccgatttt ggtggacagc                                               30

<210> SEQ ID NO 147
<211> LENGTH: 37
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 147
gctgtccgca ccaattttac cgattttggt ggacagc                                       37

<210> SEQ ID NO 148
<211> LENGTH: 37
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 148
gcaccaattt taccgatttt ggtggacagc ttggtgc                                       37

<210> SEQ ID NO 149
<211> LENGTH: 94
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 149
taatacgact cactataggc gtagcctgat gagcgtacaa cccaccaccg ttgtccacaa              60

```
atgcgaaacg tggtgaaagc cacgtagctg cgcc                                  94
```

<210> SEQ ID NO 150
<211> LENGTH: 30
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 150

```
cgtacaaccc accaccgttg tccacaaatg                                       30
```

<210> SEQ ID NO 151
<211> LENGTH: 36
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 151

```
catttgcgta caacccacca ccgttgtcca caaatg                                36
```

<210> SEQ ID NO 152
<211> LENGTH: 37
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 152

```
cgtacaaccc accaccgttg tccacaaatg ttgtacg                               37
```

<210> SEQ ID NO 153
<211> LENGTH: 94
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 153

```
taatacgact cactataggc gtagcctgat gagtgcgtca acggccgtcc cgaaacgtga      60
atacgaaacg tggtgaaagc cacgtagctg cgcc                                  94
```

<210> SEQ ID NO 154
<211> LENGTH: 30
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 154

```
tgcgtcaacg gccgtcccga aacgtgaata                                       30
```

<210> SEQ ID NO 155
<211> LENGTH: 36
<212> TYPE: DNA
<213> ORGANISM: Artificial Sequence
<220> FEATURE:
<223> OTHER INFORMATION: Artificial Sequence: In vitro synthetic nucleic acid

<400> SEQUENCE: 155
tattcatgcg tcaacggccg tcccgaaacg tgaata					36

<210> SEQ ID NO 156
<211> LENGTH: 40
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 156
gcttatgcgt caacggccgt cccgaaacgt gaatataagc					40

<210> SEQ ID NO 157
<211> LENGTH: 94
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 157
taatacgact cactataggc gtagcctgat gaggttaccc cgaaacggcc ctaactgcat					60 cagcgaaacg tggtgaaagc cacgtagctg cgcc					94

<210> SEQ ID NO 158
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 158
gttaccccga aacggcccta actgcatcag					30

<210> SEQ ID NO 159
<211> LENGTH: 37
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 159
ctgatgcgtt accccgaaac ggccctaact gcatcag					37

<210> SEQ ID NO 160
<211> LENGTH: 37
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 160
gttaccccga aacggcccta actgcatcag gggtaac					37

<210> SEQ ID NO 161
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

```
<400> SEQUENCE: 161
taatacgact cactataggc gtagcctgat gagccgcatc accacccaaa ccaccgttcg    60
aaacgtggtg aaagccacgt agctgcgcc                                     89

<210> SEQ ID NO 162
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 162
ccgcatcacc acccaaacca ccgtt                                         25

<210> SEQ ID NO 163
<211> LENGTH: 31
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 163
ccgcatcacc acccaaacca ccgttatgcg g                                  31

<210> SEQ ID NO 164
<211> LENGTH: 31
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 164
aacggtccgc atcaccaccc aaaccaccgt t                                  31

<210> SEQ ID NO 165
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 165
taatacgact cactataggc gtagcctgat gagcctgctc catccgcgcc agcctcaccg    60
aaacgtggtg aaagccacgt agctgcgcc                                     89

<210> SEQ ID NO 166
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 166
cctgctccat ccgcgccagc ctcac                                         25

<210> SEQ ID NO 167
<211> LENGTH: 30
<212> TYPE: DNA
<213> ORGANISM: Artificial Sequence
<220> FEATURE:
```

<223> OTHER INFORMATION: Artificial Sequence: In vitro synthetic nucleic
      acid

<400> SEQUENCE: 167
cctgctccat ccgcgccagc ctcacgcagg                                       30

<210> SEQ ID NO 168
<211> LENGTH: 32
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 168
gtgagggcct gctccatccg cgccagcctc ac                                    32

<210> SEQ ID NO 169
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 169
taatacgact cactataggc gtagcctgat gagccaatct cctgcccacg ccgttccacg      60
aaacgtggtg aaagccacgt agctgcgcc                                       89

<210> SEQ ID NO 170
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 170
ccaatctcct gcccacgccg ttcca                                            25

<210> SEQ ID NO 171
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 171
ccaatctcct gcccacgccg ttccaattgg                                       30

<210> SEQ ID NO 172
<211> LENGTH: 34
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 172
cctggaacca atctcctgcc cacgccgttc cagg                                  34

<210> SEQ ID NO 173
<211> LENGTH: 89
<212> TYPE: DNA
<213> ORGANISM: Artificial Sequence

```
<220> FEATURE:
<223> OTHER INFORMATION: Artificial Sequence: In vitro synthetic nucleic
      acid

<400> SEQUENCE: 173
taatacgact cactataggc gtagcctgat gagccaatca aggaccgcct tcaccgctcg    60
aaacgtggtg aaagccacgt agctgcgcc                                     89

<210> SEQ ID NO 174
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 174
ccaatcaagg accgccttca ccgct                                         25

<210> SEQ ID NO 175
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 175
ccaatcaagg accgccttca ccgctattgg                                    30

<210> SEQ ID NO 176
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 176
ccagcggtcc aatcaaggac cgccttcacc gctgg                              35

<210> SEQ ID NO 177
<211> LENGTH: 27
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 177
ccaatcaagg accgccttca ccgctgg                                       27

<210> SEQ ID NO 178
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 178
taatacgact cactataggc gtagcctgat gagactctcg catcaccagc caactcaccg    60
aaacgtggtg aaagccacgt agctgcgcc                                     89

<210> SEQ ID NO 179
```

```
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 179
actctcgcat caccagccaa ctcac                                          25

<210> SEQ ID NO 180
<211> LENGTH: 35
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 180
gcttaactct cgcatcacca gccaactcac taagc                               35

<210> SEQ ID NO 181
<211> LENGTH: 31
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 181
actctcgcat caccagccaa ctcacgagag t                                   31

<210> SEQ ID NO 182
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 182
taatacgact cactataggc gtagcctgat gagcggtact cagattacag agtgacatcg    60
aaacgtggtg aaagccacgt agctgcgcc                                      89

<210> SEQ ID NO 183
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 183
cggtactcag attacagagt gacat                                          25

<210> SEQ ID NO 184
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 184
cggtactcag attacagagt gacattaccg                                     30
```

-continued

<210> SEQ ID NO 185
<211> LENGTH: 34
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 185
ccatgtccgg tactcagatt acagagtgac atgg                               34

<210> SEQ ID NO 186
<211> LENGTH: 88
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 186
taatacgact cactataggc gtagcctgat gagagacacc acggatccga actggagcga    60
aacgtggtga aagccacgta gctgcgcc                                      88

<210> SEQ ID NO 187
<211> LENGTH: 24
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 187
agacaccacg gatccgaact ggag                                          24

<210> SEQ ID NO 188
<211> LENGTH: 29
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 188
agacaccacg gatccgaact ggagtgtct                                     29

<210> SEQ ID NO 189
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 189
ctccagagac accacggatc cgaactggag                                    30

<210> SEQ ID NO 190
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 190
taatacgact cactataggc gtagcctgat gagcctcgca agattgcata cgttagaacg    60
aaacgtggtg aaagccacgt agctgcgcc                                            89

<210> SEQ ID NO 191
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 191
cctcgcaaga ttgcatacgt tagaa                                                25

<210> SEQ ID NO 192
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 192
cctcgcaaga ttgcatacgt tagaacgagg                                           30

<210> SEQ ID NO 193
<211> LENGTH: 33
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 193
ccttctcctc gcaagattgc atacgttaga agg                                       33

<210> SEQ ID NO 194
<211> LENGTH: 89
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 194
taatacgact cactataggc gtagcctgat gagcacgtag gaaacgacct ctacggagcg          60
aaacgtggtg aaagccacgt agctgcgcc                                            89

<210> SEQ ID NO 195
<211> LENGTH: 25
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 195
cacgtaggaa acgacctcta cggag                                                25

<210> SEQ ID NO 196
<211> LENGTH: 31
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 196

```
cacgtaggaa acgacctcta cggagtacgt g                              31

<210> SEQ ID NO 197
<211> LENGTH: 30
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 197
ctccgcacgt aggaaacgac ctctacggag                                30

<210> SEQ ID NO 198
<211> LENGTH: 90
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 198
taatacgact cactataggc gtagcctgat gagcccgaaa ccaccaccgt tgtccaatac    60
gaaacgtggt gaaagccacg tagctgcgcc                                    90

<210> SEQ ID NO 199
<211> LENGTH: 26
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 199
cccgaaacca ccaccgttgt ccaata                                    26

<210> SEQ ID NO 200
<211> LENGTH: 33
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 200
cccgaaacca ccaccgttgt ccaatatttc ggg                            33

<210> SEQ ID NO 201
<211> LENGTH: 34
<212> TYPE: DNA
<213> ORGANISM: Artificial Sequence
<220> FEATURE:
<223> OTHER INFORMATION: Artificial Sequence: In vitro synthetic nucleic
      acid

<400> SEQUENCE: 201
ggtattcccg aaaccaccac cgttgtccaa tacc                           34
```